US011166476B2

(12) United States Patent
Sherlock et al.

(10) Patent No.: US 11,166,476 B2
(45) Date of Patent: *Nov. 9, 2021

(54) METHODS AND SYSTEMS FOR EXTRACTING PROTEIN AND CARBOHYDRATE RICH PRODUCTS FROM A MICROCROP AND COMPOSITIONS THEREOF

(71) Applicant: PARABEL NUTRITION, INC., Vero Beach, FL (US)

(72) Inventors: Peter Sherlock, Rockledge, FL (US); Harvey Weaver, Fellsmere, FL (US); Ebenezer Ifeduba, Palm Bay, FL (US); Paul Antelik, Gilbert, AZ (US)

(73) Assignee: Parabel Nutrition, Inc., Vero Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/799,540

(22) Filed: Feb. 24, 2020

(65) Prior Publication Data

US 2020/0214317 A1 Jul. 9, 2020

Related U.S. Application Data

(63) Continuation of application No. 15/179,963, filed on Jun. 10, 2016, now Pat. No. 10,568,343.

(51) Int. Cl.
*A01G 31/00* (2018.01)
*A23L 33/125* (2016.01)
(Continued)

(52) U.S. Cl.
CPC .............. *A23J 1/006* (2013.01); *A01G 31/00* (2013.01); *A23J 3/14* (2013.01); *A23L 33/125* (2016.08);
(Continued)

(58) Field of Classification Search
CPC ........... A23J 1/006; A23J 3/14; A23L 33/185; B01D 61/022; B01D 61/142; B01D 61/145; B01D 61/58; C07K 1/36
See application file for complete search history.

(56) References Cited

U.S. PATENT DOCUMENTS

| 296,200 A | 4/1884 | McCarty |
| 2,522,513 A | 9/1950 | Hemmeter |

(Continued)

FOREIGN PATENT DOCUMENTS

| CN | 101116986 | 2/2008 |
| CN | 101595943 | 12/2009 |

(Continued)

OTHER PUBLICATIONS

Office Action dated Jul. 3, 2020 in Chinese Application No. 201680047237.2.

(Continued)

*Primary Examiner* — Bradley R Spies
(74) *Attorney, Agent, or Firm* — Baker & McKenzie LLP

(57) ABSTRACT

The present disclosure relates, according to some embodiments, to systems for purifying proteins and carbohydrate rich products from photosynthetic aquatic species and compositions thereof. In some embodiments, a system for recovering a highly soluble protein product from a biomass comprising a microcrop (e.g., *Lemna*) may comprise (a) a lysing unit to lyse a first portion of the biomass to form a first portion of lysed biomass, (b) a first separating unit to separate the first portion of lysed biomass to generate a first portion of a juice fraction and a first portion of a solid fraction, (c) a second separating unit to separate the first portion of the juice fraction to generate a first portion of a first juice and a first portion of a first cake, (d) a first filtration unit to filter the first portion of the first juice to generate a first portion of a soluble protein and a first reject stream, (e)

(Continued)

a second filtration unit to filter the first portion of the soluble protein to generate a first portion of a second soluble protein and a second reject stream, (f) a dewatering unit to concentrate the first portion of the second soluble protein to generate a first portion of a concentrated soluble protein, and (g) a drying unit to dry the first portion of the concentrated soluble protein to generate a first portion of a dry protein concentrate.

24 Claims, 6 Drawing Sheets

(51) Int. Cl.
| | | |
|---|---|---|
| A23L 33/185 | (2016.01) | |
| B01D 61/02 | (2006.01) | |
| B01D 61/08 | (2006.01) | |
| B01D 61/14 | (2006.01) | |
| B01D 61/18 | (2006.01) | |
| B01D 61/58 | (2006.01) | |
| C07K 1/14 | (2006.01) | |
| C07K 1/34 | (2006.01) | |
| C07K 1/36 | (2006.01) | |
| A23J 1/00 | (2006.01) | |
| A23J 3/14 | (2006.01) | |
| B01D 61/04 | (2006.01) | |
| B01D 61/16 | (2006.01) | |
| B01D 1/16 | (2006.01) | |

(52) U.S. Cl.
CPC ............ *A23L 33/185* (2016.08); *B01D 61/04* (2013.01); *B01D 61/08* (2013.01); *B01D 61/142* (2013.01); *B01D 61/145* (2013.01); *B01D 61/16* (2013.01); *B01D 61/18* (2013.01); *B01D 61/58* (2013.01); *C07K 1/145* (2013.01); *C07K 1/34* (2013.01); *C07K 1/36* (2013.01); *A01G 2031/006* (2013.01); *A23V 2002/00* (2013.01); *B01D 61/022* (2013.01); *B01D 2311/02* (2013.01); *B01D 2311/04* (2013.01); *B01D 2311/08* (2013.01); *B01D 2311/2688* (2013.01)

(56) References Cited

U.S. PATENT DOCUMENTS

| | | |
|---|---|---|
| 2,692,200 A | 10/1954 | Olson |
| 2,827,454 A | 3/1958 | Nord |
| 2,867,945 A | 1/1959 | Gotaas et al. |
| 3,468,057 A | 9/1969 | Buisson et al. |
| 3,499,687 A | 3/1970 | Ellis |
| 3,674,501 A | 7/1972 | Betz et al. |
| 3,704,041 A | 11/1972 | Loveland et al. |
| 3,768,200 A | 10/1973 | Kiock |
| 3,839,198 A | 10/1974 | Shelef |
| 3,930,450 A | 1/1976 | Symons |
| 3,955,318 A | 5/1976 | Hulls |
| 4,005,546 A | 2/1977 | Oswald |
| 4,041,640 A | 8/1977 | Itanami et al. |
| 4,042,367 A | 8/1977 | Wilson |
| 4,066,633 A | 1/1978 | Gastineau et al. |
| 4,077,158 A | 3/1978 | England |
| 4,137,868 A | 2/1979 | Pryor |
| 4,253,271 A | 3/1981 | Raymond |
| 4,429,867 A | 2/1984 | Barber |
| 4,516,528 A | 3/1985 | Jones |
| 4,557,937 A | 12/1985 | Bournier |
| 4,560,032 A | 12/1985 | Imanaka |
| 4,604,948 A | 8/1986 | Goldhahn |
| 4,840,253 A | 6/1989 | DiMaggio et al. |
| 4,910,912 A | 3/1990 | Lowrey, III |
| 5,047,332 A | 9/1991 | Chahal |
| 5,121,708 A | 6/1992 | Nuttle |
| 5,171,592 A | 12/1992 | Holtzapple et al. |
| 5,269,819 A | 12/1993 | Porath |
| 5,527,456 A | 6/1996 | Jensen |
| 5,659,977 A | 8/1997 | Jensen et al. |
| 5,667,445 A | 9/1997 | Lochtefeld |
| 5,704,733 A | 1/1998 | de Greef |
| 5,941,165 A | 8/1999 | Butte |
| 6,077,548 A | 6/2000 | Lasseur et al. |
| 6,096,546 A | 8/2000 | Raskin |
| 6,251,643 B1 | 6/2001 | Hansen et al. |
| 6,348,347 B1 | 2/2002 | Hirabayashi et al. |
| 7,058,197 B1 | 6/2006 | McGuire et al. |
| 7,215,420 B2 | 5/2007 | Gellerman et al. |
| 7,674,077 B2 | 3/2010 | Opatril |
| 8,245,440 B2 | 8/2012 | Ryan et al. |
| 8,287,740 B2 | 10/2012 | Newman et al. |
| 8,722,878 B2 | 5/2014 | Raines et al. |
| 9,675,054 B2 | 6/2017 | Grajcar et al. |
| 2004/0030516 A1 | 2/2004 | Dunhill et al. |
| 2004/0144025 A1 | 7/2004 | Rutzke |
| 2006/0024689 A1 | 2/2006 | Bleuart et al. |
| 2007/0048859 A1 | 3/2007 | Sears |
| 2007/0151522 A1 | 7/2007 | Brauman |
| 2008/0032349 A1 | 2/2008 | Visckov et al. |
| 2008/0096267 A1 | 4/2008 | Howard et al. |
| 2008/0155890 A1 | 7/2008 | Oyler |
| 2009/0088757 A1 | 4/2009 | Tulkis |
| 2009/0151240 A1 | 6/2009 | Kayama et al. |
| 2009/0285642 A1 | 11/2009 | De Greef |
| 2010/0028505 A1 | 2/2010 | Katzke et al. |
| 2010/0041095 A1 | 2/2010 | Zeikus |
| 2010/0116986 A1 | 5/2010 | Obuki et al. |
| 2010/0151558 A1 | 6/2010 | Alianell et al. |
| 2010/0162620 A1 | 7/2010 | McCaffrey et al. |
| 2010/0281836 A1 | 11/2010 | Vanhoute et al. |
| 2010/0325948 A1 | 12/2010 | Parsheh et al. |
| 2011/0016773 A1 | 1/2011 | Nichols et al. |
| 2011/0092726 A1 | 4/2011 | Clarke |
| 2011/0172102 A1 | 7/2011 | Jacob et al. |
| 2012/0009660 A1 | 1/2012 | Pottathil et al. |
| 2012/0110901 A1 | 5/2012 | Olivier et al. |
| 2012/0117869 A1 | 5/2012 | Javan et al. |
| 2012/0171753 A1 | 7/2012 | Ivry |
| 2012/0288917 A1 | 11/2012 | Krenbrink et al. |
| 2012/0308989 A1 | 12/2012 | Barclay et al. |
| 2013/0023044 A1 | 1/2013 | Gleason |
| 2013/0183705 A1 | 7/2013 | Barclay et al. |
| 2013/0192130 A1 | 8/2013 | Eckelberry |
| 2013/0244309 A1 | 9/2013 | Singh et al. |
| 2014/0023675 A1 | 1/2014 | Lina et al. |
| 2014/0212955 A1 | 7/2014 | Ploechinger |
| 2014/0221630 A1 | 8/2014 | Olivier et al. |
| 2014/0338261 A1 | 11/2014 | Sykes |
| 2014/0356496 A1 | 12/2014 | Mulnyczuk |
| 2015/0072400 A1 | 3/2015 | Clarke |
| 2015/0275161 A1 | 10/2015 | Gressel et al. |
| 2016/0030350 A1 | 2/2016 | Muller |
| 2016/0288001 A1 | 10/2016 | Johnson |
| 2016/0360715 A1 | 12/2016 | Sherlock et al. |
| 2017/0223935 A1 | 8/2017 | Behrens |
| 2018/0014486 A1 | 1/2018 | Creechley et al. |
| 2018/0118595 A1 | 5/2018 | Curry |

FOREIGN PATENT DOCUMENTS

| | | |
|---|---|---|
| CN | 102448286 | 5/2012 |
| CN | 103002752 A | 3/2013 |
| CN | 202960947 | 6/2013 |
| CN | 202960947 U | 6/2013 |
| CN | 204092345 | 1/2015 |
| CN | 104413257 | 3/2015 |
| CN | 104585067 A | 5/2015 |
| DE | 4133920 | 11/1993 |
| EP | 0285195 | 10/1988 |
| EP | 0765599 | 4/1997 |
| FR | 2522479 | 9/1983 |
| GN | 104126494 | 11/2014 |

(56) References Cited

FOREIGN PATENT DOCUMENTS

| | | |
|---|---|---|
| GN | 104413257 | 3/2015 |
| JP | S52151199 | 12/1977 |
| JP | 54-73148 | 6/1979 |
| JP | S54147650 | 11/1979 |
| JP | S56-031425 | 3/1981 |
| JP | S59-183635 A | 10/1984 |
| JP | 2001502918 | 3/2001 |
| JP | 2001-346544 | 12/2001 |
| JP | 2002-306147 A | 10/2002 |
| JP | 2002-532112 A | 10/2002 |
| JP | 2004097021 | 4/2004 |
| JP | 2005007837 | 1/2005 |
| JP | 2005065626 A | 3/2005 |
| JP | 2008-043207 A | 2/2008 |
| JP | 2010-214278 A | 9/2010 |
| JP | 2011-019508 A | 2/2011 |
| JP | 2011254724 A | 12/2011 |
| JP | 2013521808 A | 6/2013 |
| KR | 20000018164 | 10/2000 |
| KR | 101153379 | 6/2012 |
| MX | 2011010995 | 1/2012 |
| NL | 20111038645 | 9/2012 |
| WO | 9105849 | 5/1991 |
| WO | 9818344 | 5/1998 |
| WO | 0145523 | 6/2001 |
| WO | 2002034755 | 5/2002 |
| WO | 03028432 | 4/2003 |
| WO | 2007109066 | 9/2007 |
| WO | 2007111677 | 10/2007 |
| WO | 2008020457 | 2/2008 |
| WO | 2008033573 | 3/2008 |
| WO | 2010123943 | 10/2010 |
| WO | 2010144877 | 12/2010 |
| WO | 2011044194 | 4/2011 |
| WO | 2011116252 | 9/2011 |
| WO | WO2011116252 | 9/2011 |
| WO | 2011-156662 A2 | 12/2011 |
| WO | 2011156662 | 12/2011 |
| WO | 2014046543 | 3/2014 |

OTHER PUBLICATIONS

Office Action dated Jul. 9, 2020 in Japanese Application No. 2018-516402.
Office Action dated Aug. 4, 2020 in Japanese Application No. 2018-506982.
Office Action dated Jun. 24, 2020 in European Application No. 16845295.1.
Office Action dated Jun. 23, 2020 in Japanese Application No. 2018-532531.
Annual Review of Plant Biology, 2005, vol. 56, p. 41-71.
Sogbesan et al, "Utilization of Treated Duckweed Meal (*Lemna pausicostata*) as Plant Protein Supplement in African Mud Catfish (*Clarias gariepinus*) Juvenile Diets", Fisheries and Aquaculture Journal, vol. 06, No. 04, Jul. 12, 2015, p. 1-5, XP055535965.
Examination Report dated Dec. 7, 2020 in European Patent Application No. 16845285.2.
Stuart L. Cantor: "New Plant Protein Powerhouses Prepared Foods", Sep. 11, 2015, XP055755579.
Titi Mutiara Kirana et al. "Effect of Blanching Treatments Against Protein Content and Amino Acid Drumstrick Leaves (*Moringa oleifera*)", Journal of Food Research, vol. 2, No. 1, Jan. 1, 2013, pp. 101-108, XP055367771.
Examination Report dated Dec. 17, 2020 in Australian Patent Application No. 2016321414.
International Search Report and Written Opinion of the International Searching Authority for PCT application No. PCT/US2016/037046, dated Oct. 27, 2016.
International Search Report and Written Opinion of the International Searching Authority (Korean Intellectual Patent Office) for International Application No. PCT/US2016/041156, dated Oct. 18, 2016.
Freidig et al., Variation in Oxalic Acid Content among Commercial Table Beet Cultivars and Related Crops. Journal of the American Society for Horticultural Science, vol. 136, No. 1, p. 54-60, 2011.
Extended Search Report in European Patent Application No. 16835862.0, dated Nov. 9, 2018.
Mazen, Ahmed M.A., "Calcium oxalate formation in Lemna minor: physiological and ultrastructural aspects of high capacity calcium sequestration" New Phytologist vol. 161, pp. 435-448, 2003.
International Preliminary Report on Patentability by the International Preliminary Examination Authority (Korean Intellectual Patent Office) for international Application No. PCT/US2016/051366, dated Mar. 22, 2018.
International Preliminary Report on Patentability by the International Preliminary Examination Authority (Korean Intellectual Patent Office) for International Application No. PCT/US2016/051380, dated Mar. 13, 2018.
Titi Mutiara K. et al., 'Effect of blanching treatments against protein content and amino acid drumstick leaves (*Moringa oleifera*)', Journal of Food Research, vol. 2, No. 1, pp. 101-108, 2013.
Gert Jan Schaafsma, 'Advantages and limitations of the protein digestibility-corrected amino acid score (PDCAAS)as a method for evaluating protein quality in human diets', British Journal of Nutrition, vol. 108, pp S333-S336, 2012.
Extended Search Report in European Patent Application No. 16845285.2, dated Jan. 15, 2019.
Watson, Elaine, "Ultra-fast-growing aquatic plant promises year-round supply of sustainable vegetable protein", Jul. 24, 2015, p. 1-4, XP055537613, www.bakeryandsnacks.com, Retrieved from Internet URL: www.bakeryandsnacks.com/Article/201 5/07 /06/ Aquatic-plant-promises-year-round-supply-of-sustainable-plant-protein. [Retrieved from Internet on Dec. 21, 2018].
Extended Search Report in European Patent Application No. 16808454.9, dated Feb. 6, 2019.
Kwag, J.H. et al. "Conditions for artificial culture of Lemna Paucicostata and potentiality as an alternative biomass source"; J Lives.House & Env. 16 (2) pp. 143-152, 2010.
International search report and written opinion of the international searching authority for co-pending PCT application No. PCT/US2016/037099, dated Oct. 5, 2016.
Sherlock et al., U.S. Appl. No. 15/179,963, 2217 pages.
Office Action dated Jan. 1, 2019 in connection with U.S. Appl. No. 15/179,963, 13 pages.
Boye, J.I., et al . . . Ch 2, "Thermal Denaturation and Coagulation of Proteins" of Food Proteins and their Applications (Damodaran et al.), 1997. ISBN 0-8247-9820-1.
Lentein, "Clean. Green. Protein", Retrieved from: https://web archive.org/web/20150901074209/https://lentein.com, web accessed on Jul. 17, 2020.
Lentein, "Green Protein Powder", Retrieved from: https://web.archive.org/web/20150822012645/https://lentein.com/lentein-plus-powder, web accessed on Jul. 17, 2020.
Office Action, mailed in Japanese Patent Application No. 2018-516396, dated Jun. 2, 2020.
Office Action, mailed in Japanese Patent Application No. 2018-516401, dated Jun. 2, 2020.
Office Action, mailed in Japanese Patent Application No. 2018-532528, dated Jun. 23, 2020.
Supplementary European Search Report in European Patent Application No. 16808482,0, dated Feb. 21, 2019.
First Examination Report in Australian Patent Application No. 2016276974, dated Apr. 9, 2019.
Office Action, mailed in Chinese Patent Application No. 201610789415.0 dated Apr. 26, 2019.
Examination Report, mailed in related Chinese Patent Application No. 201080023569.X, dated Sep. 20, 2012.
Office Action, mailed in Brazilian Patent Application No. PI1015000-5, notification published Jan. 23, 2018.
Office Action mailed in Brazilian Patent Application No. PI1015000-5, dated Dec. 20, 2017.
International Search Report and Written Opinion of the International Searching Authority (US) in related International Application No. PCT/US2010/031811, dated Jun. 18, 2010.

(56) References Cited

OTHER PUBLICATIONS

International Preliminary Report on Patentability of the International Preliminary Examination Authority (US) in related International Application No. PCT/US2010/031811, dated Oct. 11, 2011.
Office Action received in Brazilian Patent Application No. PI1015000-5, notification published May 10, 2018.
Office Action, mailed in Chinese Patent Application No. 201610789415.0 dated Nov. 5, 2018.
International Search Report and Written Opinion of the International Searching Authority (US) in PCT International Application No. PCT/US2011/028911, dated Nov. 30, 2011.
Office Action in Mexican Patent Application No. MX/a/2014/010053, dated Feb. 13, 2017.
Office Action mailed in Malaysian Patent Application No. PI 2011005000 dated Jun. 30, 2015.
Extended Search Report in European Patent Application No. 11757038.2, dated Mar. 9, 2017.
Office Action in European Patent Application No. 11757038.2, dated Jul. 16, 2018.
Office Action in Australian Patent Application No. 2015255285, dated Mar. 3, 2017.
Preliminary Examination Report in Peruvian Patent Application No. 1563-2012, dated Apr. 17, 2017.
International Preliminary Report on Patentability of the International Preliminary Examination Authority in PCT International Application No. PCT/US2011/028911, dated Sep. 18, 2012.
Office Action in Canadian Patent Application No. 2793512, dated Mar. 28. 2018.
Office Action in Canadian Patent Application No. 2793512, dated Aug. 7, 2017.
Office Action in Indonesian Patent Application No. W00201204170, dated Sep. 29, 2017.
Office Action in Japanese Patent Application No. 2015-020932 dated Jan. 27, 2017.
Office Action in Japanese Patent Application No. 2015-020932 dated Dec. 5, 2017.
Office Action in Indian Patent Application No. 8902/DELNP/2012 dated Aug. 3, 2018.
Office Action in European Patent Application No. 11757038.2, dated Jan. 3, 2019.
International Preliminary Report on Patentability by the International Preliminary Examination Authority for International Application No. PCT/US2016/037097, dated Dec. 22, 2017.
Cheng et al., "Growing Duckweed to Recover Nutrients from Wastewaters and for Production of Fuel Ethanol and Animal Feed", Clean, vol. 37, No. 1, pp. 17-26 (2009).
International Preliminary Report on Patentability by the International Preliminary Examination Authority (Korean Intellectual Patent Office) for international Application No. PCT/US2016/037099, dated Dec. 12, 2017.
Extended Search Report in European Patent Application No. 16808483.8, dated Dec. 21, 2018.
International Preliminary Report on Patentability by the International Preliminary Examination Authority (Korean Intellectual Patent Office) for international Application No. PCT/US2016/037046, dated Dec. 12, 2017.
International Preliminary Report on Patentability by the International Preliminary Examination Authority (Korean Intellectual Patent Office) for international Application No. PCT/US2016/041156, dated Jan. 18, 2018.
International Search Report and Written Opinion of ttle international Searching Authority (Korean Intellectual PatentOffice) for corresponding PCT application No. PCT/US2016/046422, dated Nov. 10, 2016.
International Preliminary Report on Patentability by the International Preliminary Examination Authority (Korean Intellectual Patent Office) for International Application No. PCT/US2016/046422, dated Feb. 22, 2018.
International Search Report and Written Opinion of the International Searching Authority for PCT Application No. PCT/US2016/051366, dated Dec. 22, 2016.
International Search Report and Written Opinion of the International Searching Authority for PCT application No. PCT/US2016/051380, dated Dec. 26, 2016.
Sogbesan, OA; "Utilization of Treated Duckweed Meal (*Lemna pausicostata*) as Plant Protein Supplement in African Mud Catfish (*Clarias gariepinus*) Juvenile Diets" Fisheries and Aquaculture Journal, vol. 6, issue 4, ISSN: 2150-3508 FAJ, 2015.
Extended Search Report of European Patent Office in European Patent Application No. 16845295.1, dated Jan. 15, 2019.
Office Action, mailed in Indian Patent Application No. 8948/DELNP/2011 dated Apr. 11, 2018.
Office Action, mailed in Brazilian Patent Application No. PI1015000-5, dated Sep. 26, 2018.
Pedroni et al., A Proposal to Establish International Network on Biofixation of $CO_2$ and Greenhouse Gas Abatement with Microalgae, Journal of Energy and Environmental Research, vol. 1, No. 1, Nov. 2001.
http://www.aquaponics.net.au, Murray Hallam, Practical Aquaponics for Everyone, Wayback Machine Dec. 2008, 3 pages.
Https://jeremybiggs.wordpress.com/2008/10/28/duck-attack/, The Garden Pond Blog, Oct. 2008, 2 pages.
http://collections.infocollections.org/ukedu/en/d/Jii23we/9.1.html, Workshop to produce an Information Kit on Farmer-proven integrated agriculture-aquaculture technologies, IIRR; 1992, 10 pages.
Fasakin, E.A. "Nutrient quality of leaf protein concentrates produced from water fern {*Azolla africanna Oesv*) and Duckweed {*Spirodela polyrrhiza* L. *Schleiden*)", Bioresource Technology., vol. 69, No. 2, Aug. 1, 1999 {Aug. 1, 1999), pp. 185-187.
Fowden, L. "The Composition of the Bulk Proteins of Chlorella" [online] Published Jun. 20, 1951. Retrieved fromInternet Jun. 1, 2017: <URL:https://www.ncbi.nlm.nih.gov/pmc/articles/PMC1197660/pdf/biochemj00910-0079.pdf>.
Bolenz, S. et al. Treatments of Water Hyacinth Tissue to Obtain Useful Products'\Biological Wastes, Amsterdam, NL, vol. 33, No. 4, Jan. 1, 1990 {Jan. 1, 1990), pp. 263-27 4.
Kindel, Paul K. et al., "Solubilization of pectic polysaccharides from the cell walls of Lemna minor and Apium graveolens". Phytochemistry, vol. 41, No. 3, Feb. 1, 1996 {Feb. 1, 1996), GB, pp. 719-723.
Byers, M. "The Amino Acid Composition of Some Leaf Protein Preparations" in IBP Handbook No. 20, Leaf Protein Its agronomy, Preparation, Quality and Use. 1971, International Biological Programme pp. 95-115.
Kennedy, David "Leaf Concentrate: A Field Guide for Small Scale Programs". Leaf for Life, 1993.
Office Action dated Aug. 21, 2020 in Chinese Application No. 201680065224.8.
Office Action dated Nov. 12, 2020 in European Patent Application No. 16808482.0.
Office Action dated Dec. 14, 2020 in Chinese Application No. 201680058494.6.
Office Action dated Sep. 2, 2020 in Chinese Application No. 201680047105.x.
Office Action dated Dec. 3, 2020 in Chinese Application No. 201680047175.5.
Kammerer, Dietmar Rolf, Chapter 11—Resin Adsorption and Ion Exchange to Recover and Fractionate Polyphenols Polyphenols in Plants, 219-230.
Office Action dated Nov. 17, 2020 in Brazilian Patent Application No. BR112018004808-9 (agent's reporting letter).
Mazen, Ahmed M. A., et al. Calcium oxalate formation in Lemna minor physiological and ultrastructural aspects of high capacity calcium sequestration. New Phytologist (2003), 435-448.
Extended European Search Report dated Feb. 26, 2021 in European Patent Application No. 20197495.3.
Office Action dated May 28, 2021 in Australian Patent Application No. 2016276972.
Notice of Acceptance dated May 12, 2021 in Australian Patent Application No. 2016321425.

(56) References Cited

OTHER PUBLICATIONS

Office Action dated May 24, 2021 in Australian Patent Application No. 2020201808.
Office Action dated Jun. 18, 2021 in Chinese Patent Application No. 201680065224.8.
Office Action dated Apr. 27, 2021 in Japanese Patent Application No. 2018-532528.

METHODS AND SYSTEMS FOR EXTRACTING PROTEIN AND CARBOHYDRATE RICH PRODUCTS FROM A MICROCROP AND COMPOSITIONS THEREOF

CROSS-REFERENCE TO RELATED APPLICATIONS

This application is a continuation of U.S. application Ser. No. 15/179,963 filed on Jun. 10, 2016, which claims priority to U.S. Provisional Application No. 62/173,643 filed on Jun. 10, 2015, all of which are hereby incorporated by reference herein for all purposes.

FIELD OF THE DISCLOSURE

The present disclosure relates, in some embodiments, to methods and systems for extracting proteins and carbohydrate rich products from a microcrop (e.g., photosynthetic aquatic species, *Lemna*) and compositions thereof. More specifically, the present disclosure relates, in some embodiments, to methods and systems for extracting proteins and carbohydrate rich products from *Lemna*. In some embodiment, the present disclosure relates to compositions of a microcrop protein product isolated from a microcrop.

BACKGROUND OF THE DISCLOSURE

An ever-increasing global population continues to fuel a plethora of sustainability concerns including sufficient and affordable access to protein sources for both feed animals and human consumption, particularly in developing nations. Additionally, concerns relating to climate change and fossil fuel consumption continue to drive innovators to develop and improve both biofuel sources and efficiency.

While marine protein sources are often utilized in feeds due to their desirable nutritional profile and enhanced palatability, high production costs lead to an increased demand for alternatives. However, many plant species are unsuitable alternatives due to their inferior amino acid profile and/or high fiber content. Furthermore, many practices for extracting protein from alternative protein sources yield products with protein integrity, solubility, and/or dispersibility characteristics that are unsuitable for many plant and animal feed applications. Additionally, water conservation concerns—particularly in equatorial and arid regions—are a driving factor in identifying suitable alternative species for the production of protein concentrates and/or fuel feed stocks.

SUMMARY

A system for recovering a highly soluble protein product from a biomass including a microcrop (e.g., *Lemna*) may, according to some embodiments, include one or more of: a lysing unit to lyse a first portion of the biomass to form a first portion of lysed biomass; a separating unit to separate the first portion of lysed biomass into a first portion of a juice fraction and a first portion of a solid fraction; a separating unit to separate the first portion of the juice fraction into a first portion of a first juice and a first portion of a first cake; a filtration unit (e.g., a microfiltration module) to filter the first portion of the first juice into a first portion of a soluble protein and a first reject stream (e.g., a retentate); a filtration unit (e.g., an ultrafiltration module, a diafiltration module, a nanofiltration module) to filter the first portion of the soluble protein and generate a first portion of a second soluble protein and a second reject stream; a dewatering unit (e.g., a reverse osmosis filtration module, a nanofiltration module) to concentrate the first portion of the second soluble protein; and a drying unit to dry the first portion of the concentrated soluble protein and generate a first portion of a dry protein concentrate having one or more of: (a) a protein concentration of at least about 50% by weight, (b) a solubility value (% water soluble nitrogen) of at least 50%, and (c) a dispersibility value (water dispersible protein/total protein) of at least 50%.

In some embodiments a system may include one or more of: a separating unit to separate the first portion of the solid fraction to generate a first portion of a first solid and a first portion of a second juice; a separating unit to separate at least one of: (a) the first portion of the first cake and (b) the first portion of the second juice, into a first portion of a second cake and a first portion of a third juice; a lysing unit to lyse a second portion of the biomass to form a second portion of a lysed biomass; a separating unit to separate the second portion of lysed biomass into a second portion of the juice fraction and a second portion of the solid fraction; a separating unit to separate the second portion of the juice fraction into a second portion of the first juice and a second portion of the first cake (the first portion of the third juice and the second portion of the juice fraction being combined prior to separating the second portion of the juice fraction); a combining unit to combine at least one of: (a) the first portion of the first solid, (b) the first portion of the first cake, and (c) the first portion of the second cake; and a processing unit to process one or more of: (a) the first portion of the solid mixture, and (b) the first portion of the first solid, into a carbohydrate-rich product comprising at least one of a dry biocrude and a carbohydrate-rich meal. A system may include one or more of: a filtering unit (e.g., a microfiltration module) to filter the second portion of the first juice and generate a second portion of the first soluble protein and the first reject stream; and a filtration unit to filter the second portion of the first soluble protein to generate a second portion of the second soluble protein and the second reject stream (the first portion of the third juice and the second portion of the juice fraction being combined prior to filtering the second portion of the juice fraction).

One or more washing units, drying units, reducing units, chilling units, and directing units may be included in a system. Washing units may be configured to wash biomass portions with one or more wash solutions (e.g., a reject stream, water, an ozonated solution) and/or at least one solvent (e.g., methanol, ethanol). A drying unit may be configured to dry a portion of the concentrated soluble protein to generate a first portion of a dry protein concentrate. Reducing units may be configured to subject protein products to a polyphenol reduction process to generate a product having reduced polyphenol concentrations (e.g., at least one polyphenol). Chilling units may be configured to chill at least one of: a first portion of lysed biomass, a first portion of the juice fraction, a first portion of the first juice, a first portion of the first soluble protein, a first reject stream, the first portion of the second soluble protein fraction, the second reject stream, and the permeate, to form a chilled stream. A directing unit may be configured to perform one or more of the functions of: (a) directing the chilled stream to flow in proximity to a donor stream having thermal energy such that the chilled stream absorbs at least some of the donor stream thermal energy; and (b) directing a thermal energy from at least one of: (i) the drying the concentrated protein, and (ii) the chilling the flow in proximity to a recipient stream, such that the recipient stream absorbs at least some of the thermal energy to form a heated stream. A donor stream may include at least one of: the first portion of the lysed biomass, the first portion of the juice fraction, and the first portion of the first juice. A recipient stream may include at least one of: the first portion of the lysed biomass, the first portion of the juice fraction, the first portion of the first juice, the first portion of the first soluble protein fraction, the first reject stream, the first portion of the second soluble protein fraction, the second reject stream, and the permeate.

Filtering units of a system may include one or more of ultrafiltration modules, diafiltration modules, microfiltration modules, and nanofiltration modules. Filtering units may have one or more filters having associated filter sizes (e.g., 0.5 μm) and/or molecular cut off weights (e.g., 10 kDa, 3 kDa).

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Some embodiments of the disclosure may be understood by referring, in part, to the present disclosure and the accompanying drawings, wherein.

DETAILED DESCRIPTION

Figure 1:
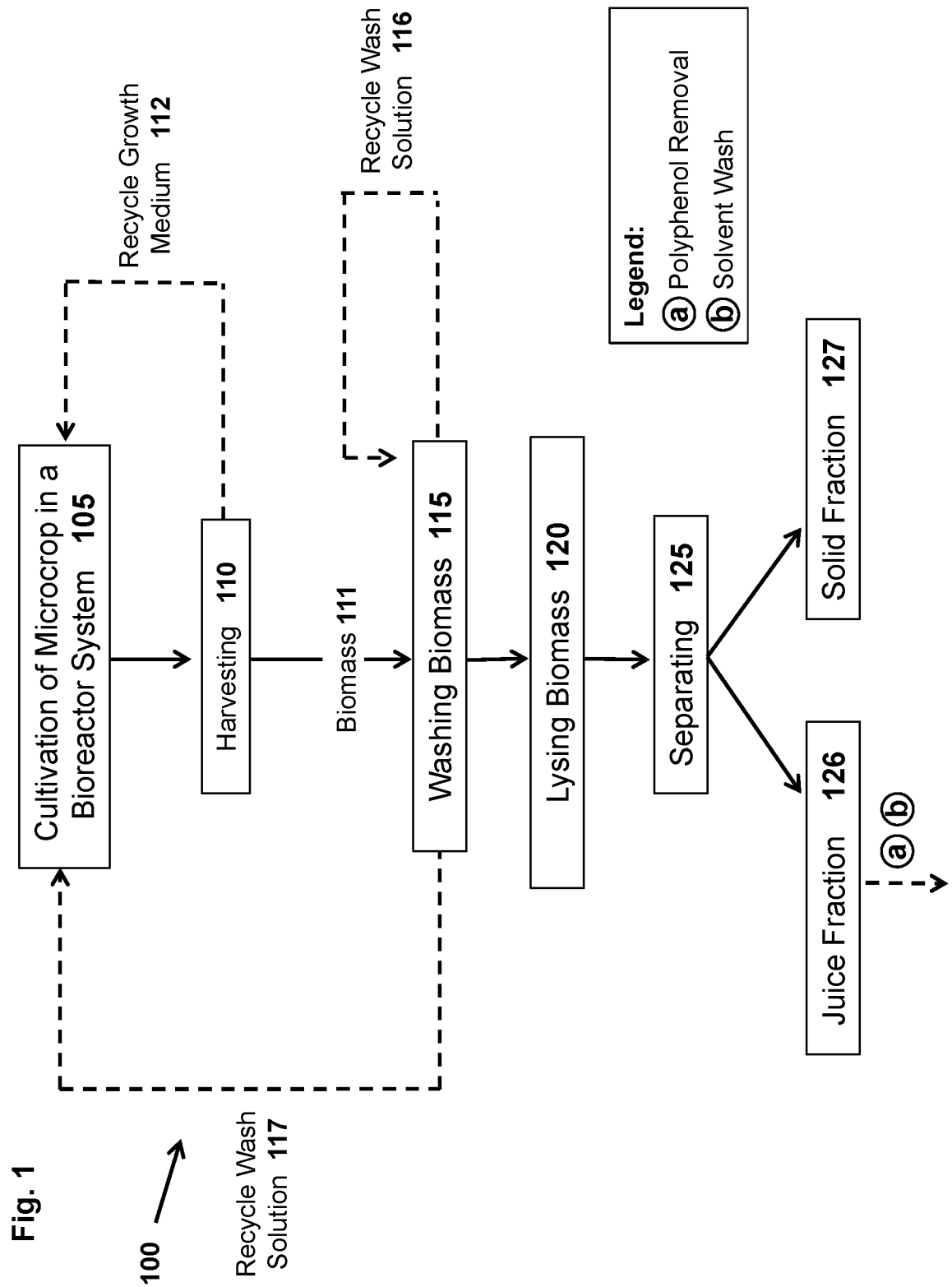
FIG. 1 is a flow diagram illustrating a system for cultivating, harvesting, and processing a microcrop for the production of protein concentrate and/or carbohydrate rich products according to a specific example embodiment of the disclosure.

The present disclosure relates to compositions, systems, and methods for producing a protein concentrate (e.g., soluble protein, dry protein concentrate) and/or a carbohydrate rich product from a microcrop (e.g., photosynthetic aquatic species, aquatic plant species, *Lemna*, *algal* species). For example, a method may comprise growing, harvesting, and/or separating a microcrop (e.g., aquatic plant species, *Lemna*, *algal* species) for the production of a protein concentrate (e.g., soluble protein, dry protein concentrate) and/or a carbohydrate rich products according to specific example embodiments of the disclosure. A method may be performed, in some embodiments, in a series of steps, one or more of which may be repeated. For example, a method may comprise a single cycle (e.g., no step is repeated) resulting in the production of a protein concentrate (e.g., soluble protein, dry protein concentrate) and/or a carbohydrate rich product. In some embodiments, a method may comprise multiple cycles (e.g., first portion, second portion) or a continuous process for the production of a protein concentrate (e.g., soluble protein, dry protein concentrate) and/or a carbohydrate rich product such that products, intermediates and/or byproducts of an earlier cycle of the process may be recycled into one or more subsequent cycles of the process.

Microcrop

In some embodiments, a microcrop may comprise a single photosynthetic aquatic species (e.g., *Lemna* species, *Salvinia* species). A microcrop may include species of *Lemna* (e.g., duckweed), *Spirodela*, *Landoltia*, *Wolfiella*, *Salvinia* (e.g., floating fern), *Wolffia* (e.g., watermeal), *Azolla* (e.g., mosquito fern), *Pistia* (e.g., water lettuce), or any combination thereof. According to some embodiments, a microcrop may be a species of *Lemna*, for example, *Lemna minor*, *Lemna obscura*, *Lemna minuta*, *Lemna gibba*, *Lemna valdiviana*, or *Lemna aequinoctialis*. In some embodiments a microcrop may include one ore more species of algae. A microcrop may comprise, according to some embodiments, a combination of two or more photosynthetic aquatic species. In some embodiments, a microcrop may be selected from a local photosynthetic aquatic species based on identified compositional and growth characteristics that have developed within one or more conditions of a local environment. Local species may out-compete other species in open ponds or bioreactors based on their adaptation to one or more conditions of a local environment. A microcrop, in some embodiments, may be adjusted in response to seasonal variations in temperature and light availability.

A microcrop may have characteristics that are advantageous in comparison to other photosynthetic aquatic species (e.g., rapid growth rate; reduced nutritional requirements; ease of harvesting and/or processing; enhanced amino acid profile; enhanced palatability; reduced evapotranspiration rate; increased protein composition).

For example, *Lemna* is a genus of free-floating aquatic plants from the Lemnaceae family (e.g., duckweed) that grow rapidly. *Lemna* protein has an essential amino acid profile that more closely resembles animal protein than most other plant proteins. Table 1 shows a typical essential amino acid compositional profile of *Lemna* protein. Additionally, *Lemna* provides high protein yields, with freshly harvested *Lemna* containing up to about 43% protein by dry weight. Furthermore, compared with most other plants, *Lemna* leaves have a low fiber content (e.g., about 5%—about 15% in dry matter) and are highly digestible, even for monogastric animals. This contrasts with compositions of many crop species (e.g., soy beans, rice, maize) which have fiber contents of approximately 50% and low digestibility.

TABLE 1

Essential Amino Acid Profile of Lemna Protein Concentration

| Essential Amino Acid | Protein (g/100 g) |
| --- | --- |
| Lysine | 5.9 |
| Leucine | 9.7 |
| Isoleucine | 5.1 |
| Methionine | 2.4 |
| Phenylalanine | 6.3 |
| Threonine | 4.4 |
| Tryptophan | 2.0 |
| Valine | 6.3 |

TABLE 1-continued

Essential Amino Acid Profile of Lemna Protein Concentration

| Essential Amino Acid | Protein (g/100 g) |
|---|---|
| Histidine | 2.7 |
| Arginine* | 6.8 |

*Conditionally non-essential amino acid.

Cultivation of a Microcrop

In some embodiments a microcrop may be asexually propagated (e.g., cultivated) by contacting a microcrop with an aqueous nutrient composition under conditions that permit expansion. A microcrop may be cultivated in a bioreactor system, according to some embodiments. A bioreactor system may contain a growth medium. In some embodiments a growth medium may comprise water and/or a nutrient composition. A growth medium (e.g., water) may be provided in and/or added to a bioreactor (e.g., a pond) and may be maintained at a desired set-point level (e.g., specific volume), according to some embodiments. A bioreactor system, in some embodiments, may be configured to collect rainfall and/or to intake water from a source of ground, surface, or recycled water (e.g., storm water, recycled water) or any other suitable water source. According to some embodiments, a bioreactor system may further comprise an additional storage container (e.g., container or pond) for excess growth medium. A bioreactor system may be configured to insert additional nutrients (e.g., nitrogen, phosphorus, potassium) or gases (e.g., oxygen; carbon dioxide) at specified time indicators or in response to sensor readings. In some embodiments, one or more smaller bioreactors (e.g., pond) may be designed and sized to adequately serve as "feeder" bioreactors to a larger bioreactor. Smaller bioreactors, in some embodiments, may be first inoculated and grown to high density at which point they may optimally seed a larger bioreactor in a manner that supports faster growth.

In some embodiments, a bioreactor system may comprise a monitoring system. A monitoring system may be configured to display and/or provide one or more user alerts regarding bioreactor condition(s) (e.g., nutrient concentrations, pH, dissolved oxygen levels, growth medium levels, microcrop distribution, flow rate, temperature) and/or adjust operating conditions (e.g., growth medium flow rate and/or timing and/or quantity of nutrient addition; "feeder" microcrop addition, oxygen or carbon dioxide addition), in some embodiments. Adjustments may be made continuously, semi-continuously, periodically, intermittently, as needed, at set or variable times, or any other interval. In some embodiments, adjustments may be selected to optimize growth rates and/or yield of a photosynthetic aquatic species. For example, a microcrop species may be grown in large-scale, open bioreactors with monitoring systems configured to adjust an introduction of materials (e.g., fresh or recycled water, fresh or recycled growth media) based on, for example, exposure to light, which may thereby regulate nutrient consumption rates.

A bioreactor system may comprise, in some embodiments, a single container in which a microcrop may be cultivated. In some embodiments, a bioreactor system may comprise multiple cultivation containers that may be connected, partially connected, or disconnected. A bioreactor (e.g., a pond), in some embodiments, may be an earthen basin with at least one embankment (e.g., made of compacted dirt removed from an interior bottom of the bioreactor). According to some embodiments a bioreactor may be an artificial container (e.g., metal, plastic, resin). A bioreactor system may comprise an open bioreactor, a closed bioreactor, a semi-open bioreactor, or any combination thereof. In some embodiments, a bioreactor system may be configured to divide the container(s) into channels or cells. A bioreactor system may be configured to permit a flow of growth medium, in some embodiments. A bioreactor system, in some embodiments, may include a propulsion system (e.g., paddle wheels, bubbling, submerged or surface water jets, submerged mixers) and/or a recirculation system. In some embodiments, a bioreactor system may be configured to adjust a flow rate of a growth medium (e.g., to redistribute nutrient concentrations or microcrop growth patterns).

In some embodiments a bioreactor system may be open (e.g., in a horizontal plane relative to the ground) of a bioreactor container (e.g., serpentine raceway) such that a growth medium contained within the bioreactor container and/or a microcrop growing on a top surface of the growth medium may be exposed to a wind initiating from an exterior of the bioreactor container. A bioreactor system, according to some embodiments, may be partially open (e.g., in a horizontal plane relative to the ground) with at least 90% or at least 80%, or at least 70%, or at least 60%, or at least 50%, or at least 40%, or at least 30%, or at least 20%, or at least 10% of the top surface of the contained culture media being open. A top surface may be open, according to some embodiments, where the surface is substantially free (e.g., free) of any covering or other barrier, where the surface is directly exposed to ambient weather conditions, where there is substantially no membrane, glass, cover or other barrier (whether or not such barrier has pores or apertures) between the surface and the atmosphere, and/or where ambient atmosphere is the only occupant of the space immediately and directly above the surface for a distance of at least about 1 meter above the surface.

A bioreactor system, in some embodiments, may monitor and adjust a thickness and distribution of a microcrop mat. For example, when a microcrop reaches a specified thickness or distribution a bioreactor system may initiate harvest procedures. In some embodiments, a minimum thickness of a microcrop may be maintained such that a desired evapotranspiration rate of a growth medium within a bioreactor system may be maintained. A minimum thickness of a microcrop may be maintained, in some embodiments, such that less sunlight is capable of penetrating a surface of a growth medium (i.e., reducing a growth potential of submerged photosynthetic aquatic species such as algae).

Harvesting of a Microcrop

A microcrop may be harvested in whole or in part at any desired time(s). For example, a microcrop may be harvested at one or more specific times, at regular or irregular intervals and/or continuously. Selection of harvest time(s) and/or intervals may be based on environmental conditions (e.g., precipitation, relative humidity, temperature range, average, low or high threshold and/or light intensity, wavelength range, duration of exposure) and/or the microcrop exhibiting one or more desired characteristics (e.g., mat thickness, mat distribution, maturation). Harvesting a microcrop may be manual or automated. In some embodiments, an automated skimmer system may collect a microcrop from a bioreactor system and transfer a harvested microcrop (e.g., via a pumping system) onto an inclined vibrating screen to separate a biomass from growth medium and debris. A microcrop, in some embodiments, may be harvested by vacuum skimming the microcrop from a bioreactor system through a stationary or mobile screen filter. According to some embodiments, a biomass slurry, including a harvested microcrop (e.g., *Lemna*) and a growth medium (e.g., water), may be conveyed to an inclined vibrating screen where a biomass (e.g., microcrop) may be separated from the growth medium.

During harvesting, a separated growth medium may be recycled back into a bioreactor system or to an additional storage container (e.g., container or pond), according to some embodiments. In some embodiments, at least about 40%, or at least about 50%, or at least about 60%, or at least about 70%, or at least about 80%, or at least about 90%, or at least about 95% of a growth medium (e.g., water) separated from a biomass may be recycled for further use in cultivating, harvesting, and/or processing a microcrop.

Washing a Biomass

In some embodiments, processing a microcrop or biomass (e.g., first portion, second portion) may include a wash procedure to remove excess growth medium, debris, contaminants, microorganisms, and/or toxins. Washing a biomass may increase protein purity and/or yield. A wash procedure may disinfect and/or disinfest a biomass, reducing or removing bacteria, fungi, viruses, insects, and any combination thereof which are on or around at least one surface of the biomass. In some embodiments a wash procedure may be performed by exposing (e.g., submerging, spraying) at least one surface of a biomass to a wash solution (e.g., water, growth medium, antimicrobial solution). A wash solution, in some embodiments, may be combined with a biomass (e.g., first portion, second portion) to form a slurry.

Figure 4:
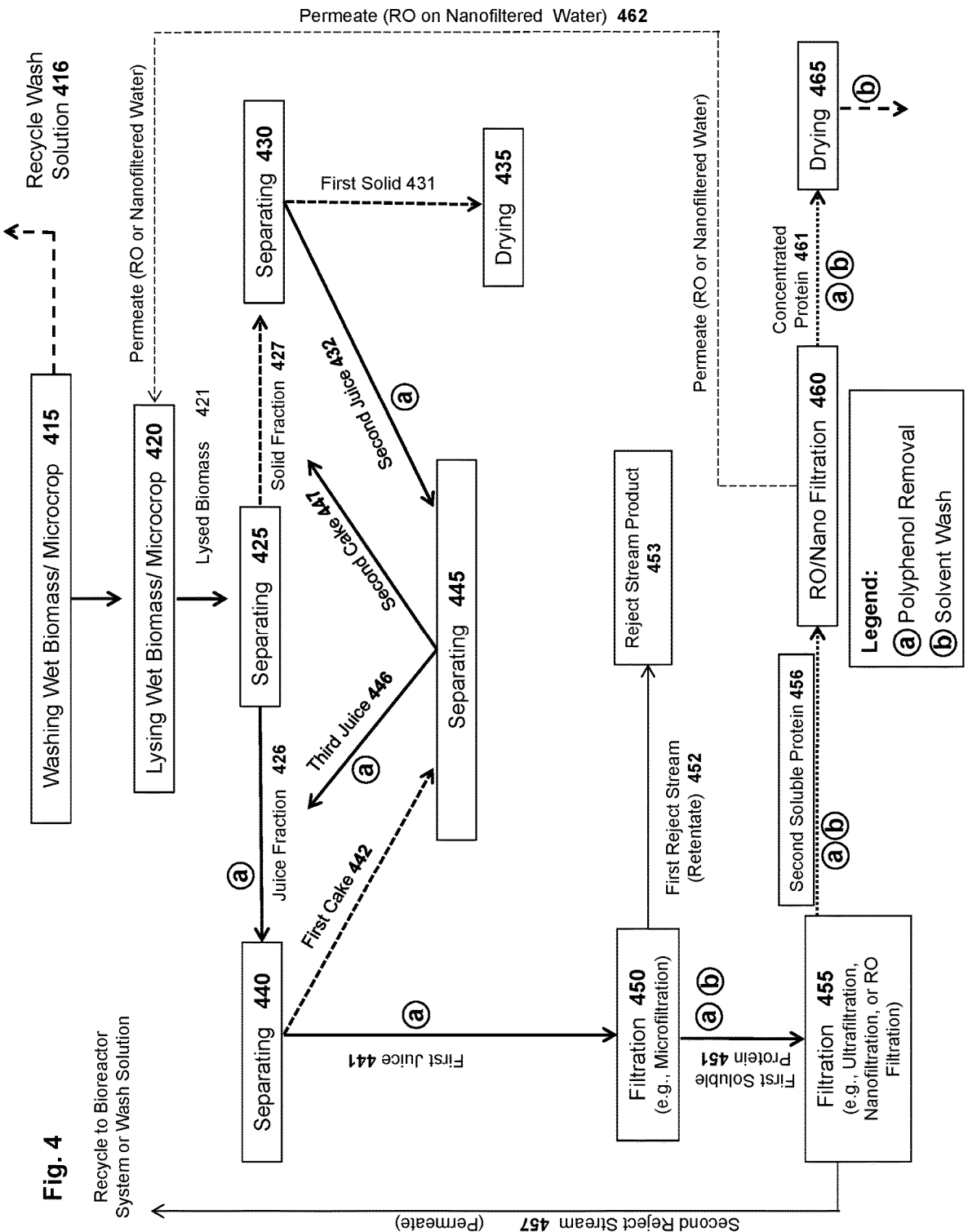
FIG. 4 is a flow diagram illustrating a process for continuously producing a protein concentrate and/or a carbohydrate rich product from a biomass according to a specific example embodiment of the disclosure.

In some embodiments, a wash solution may comprise any desired portion of recycled fluid. For example, a wash solution may comprise at least about 10% (v/v), at least about 20% (v/v), at least about 30% (v/v), at least about 40% (v/v), at least about 50% (v/v), at least about 60% (v/v), at least about 70% (v/v), at least about 80% (v/v), or at least about 90% (v/v) fluid recycled from another stage of the process (e.g., a recycled wash solution FIG. 1, 116, a reject stream from filtration (e.g., FIG. 2A, 252; FIG. 4, 452, 457)). In some embodiments a wash solution may be an aqueous solution or solvent. A wash solution may contain one or more antimicrobials, de-infestation compounds, fatty acids, alcohols, chlorine, oxidizing compounds, and any combination thereof (e.g., ozonated water).

According to some embodiments a wash solution may be applied at an elevated temperature and/or high pressure. A wash solution, in some embodiments, may remain in contact with a biomass for at least about 1 second, or for at least about 5 seconds, or for at least about 10 seconds, or for at least about 20 seconds, or for at least about 30 seconds, or for at least about 1 minute, or for at least about 5 minutes. In some embodiments, a second wash solution (e.g., water, ozonated water, a recycled wash solution (FIG. 1, 116) may be applied to a biomass. A third wash solution (e.g., water, ozonated water, recycled wash solution) may be applied to a biomass, in some embodiments. A composition of a first wash solution, a second wash solution, and a third wash solution may be the same or different from one another. In some embodiments a first wash solution may be or may comprise a reject stream from a filtration process (e.g., FIG. 2A, 252; FIG. 4, 452, 457), a second wash solution may be water, and a third wash solution may be ozonated water. Some or all of a wash solution (e.g., a first, second, and/or third wash solution), in some embodiments, may be separated from a biomass (e.g., using an inclined screen or vibratory screen).

In some embodiments, some or all of a wash solution, second wash solution, and/or third wash solution may be collected and reused/recycled (e.g., FIG. 1, 116/117). At least about 40%, or at least about 50%, or at least about 60%, or at least about 70%, or at least about 80%, or at least about 90%, or at least about 95% of a wash solution, second wash solution, and/or third wash solution (e.g., water) separated from a biomass may be recycled for future use (e.g., recycled wash solution (FIG. 1, 116), used as growth medium in a bioreactor system (FIG. 1, 117)), according to some embodiments.

A wash solution (e.g., a first, second, and/or third wash solution) may have a temperature below room temperature (e.g., about 12° C.) at a time of use. Cooling a wash solution, and thereby a microcrop, may improve protein recovery efficiency and/or decrease proteolytic activity. In some embodiments, a wash solution (e.g., a first, second, and/or third wash solution) may have a temperature below about 30° C., or below about 20° C., or below about 15° C., or below about 10° C., or below about 5° C., or below about 2° C., or below about 1° C., or below about 0° C. at a time of use. A wash solution (e.g., a first, second, and/or third wash solution) may have a temperature between about 0° C. and about 10° C., or between about 5° C. and about 15° C., or between about 10° C. and about 20° C., or 15° C. and about 25° C., or between about 20° C. and about 30° C. at a time of use, in some embodiments.

In some embodiments, a wash solution (e.g., a first, second, and/or third wash solution) may have a temperature above room temperature (e.g., about 50° C.) at a time of use. Heating a wash solution, and thereby a microcrop, may improve protein recovery efficiency, decrease proteolytic activity (e.g., denature proteolytic enzymes), and/or decrease microbial contamination (e.g., pasteurization). In some embodiments, a wash solution (e.g., a first, second, and/or third wash solution) may have a temperature above about 20° C., or above about 25° C., or above about 30° C., or above about 35° C., or above about 40° C., or above about 45° C., or above about 50° C., or above about 55° C., or above about 60° C., or above about 65° C., or above about 70° C., or above about 75° C., or above about 80° C., or above about 85° C., or above about 90° C., or above about 95° C., or above about 100° C. at a time of use. A wash solution (e.g., a first, second, and/or third wash solution) may have a temperature between about 40° C. and about 50° C., or between about 45° C. and about 55° C., or between about 50° C. and about 60° C. at a time of use, in some embodiments. According to some embodiments, a wash solution (e.g., a first, second, and/or third wash solution) may have a temperature between about 75° C. and about 80° C., or between about 80° C. and about 85° C., or between about 85° C. and about 90° C., or between about 90° C. and about 95° C., or between about 95° C. and about 100° C. at a time of use. In some embodiments, a wash solution (e.g., a first, second, and/or third wash solution) may have a temperature between about 50° C. and about 80° C., or between about 55° C. and about 85° C., or between about 60° C. and about 90° C., or between about 65° C. and about 95° C., or between about 70° C. and about 100° C. at a time of use.

Lysing a Biomass

According to some embodiments a biomass (e.g., washed or un-washed) may be lysed to form a lysed biomass (e.g., first portion, second portion). As used herein, lysing may include mechanical, chemical, and/or ultrasonic (e.g., sonication) procedures that disturb the organization of an organism on a level of individual cells or multicellular structures. Lysing may include, in some embodiments, rendering carbohydrates, proteins, and micronutrients present in a microcrop more available for downstream processing to purified protein, carbohydrate-containing materials, and/or micronutrient-containing fluids. According to some embodiments, lysing may be achieved using individually or a combination of mechanical, chemical, and/or ultrasonic (e.g., sonication) methods.

In some embodiments, lysing may be performed at temperatures below room temperature. Lysing a microcrop at a lower temperature may improve yields, for example, by limiting or decreasing undesired enzymatic activity (e.g., proteolytic activity). Lysing may be performed, in some embodiments, at a temperature below about 30° C., or below about 20° C., or below about 15° C., or below about 10° C., or below about 15° C., or below about 10° C., or below about 5° C., or below about 2° C., or below about 1° C., or below about 0° C. A lying fluid (e.g., water, recycled water, reverse osmosis water) may be added to a biomass, washed or unwashed, before or during lysing according to some embodiments. For example, at least about 10%, at least about 20%, at least about 30%, at least about 40%, at least about 50%, at least about 60%, at least about 70%, at least about 80%, or at least about 90% of lysing fluid may be water generated as a result of reverse osmosis/nanofiltration of a filtration product (e.g., FIG. 3, 362; FIG. 4, 462). In some embodiments a lysing fluid may be at a temperature below about 30° C., or below about 20° C., or below about 15° C., or below about 10° C., or below about 5° C., or below about 2° C., or below about 1° C., or below about 0° C. A lysing fluid, in some embodiments, may include buffers, protease inhibitors, anti-microbial agents, chelators (e.g., EDTA), reducing agents, or any combination thereof.

According to some embodiments, lysing may be performed at temperatures above room temperature (e.g., about 40° C.), for example, to enhance cellulosic breakdown and/or denature undesired enzymes (e.g., proteolytic enzymes). Lysing may be performed at a temperature above about 30° C., or above about 35° C., or above about 37° C., or above about 40° C., in some embodiments.

Lysing may include, for example, chopping, shredding, smashing, pressing, tearing, ultrasonic treatment (e.g., sonication), lysis by osmotic pressure, chemical treatments that degrade biological structures, or any combination thereof. In some embodiments, lysing is achieved in a mechanical way (also referred to as milling), for example, by milling, grinding, or shredding a biomass to generate a lysed biomass. A lysing process may be achieved using, for example, a shear mill, a ball mill, a colloid mill, a knife mill, a hammer mill, a grinding mill, a puree machine, a filter press, a mechanical press or any combination thereof.

In some embodiments, entry into or exit from a lysing (e.g., milling) process may be metered at any desired volume, mass, or other rate or interval (e.g., a constant rate, a variable rate, continuously, semi-continuously, periodically, intermittently). A feed rate and/or mode may be determined based on considerations including, for example: a target production rate; apparatus(es) employed in a process; properties of a feedstock, or any combination thereof. A feed rate, in some embodiments, may be at least about 10 kg/hour, or at least about 50 kg/hour, or at least about 100 kg/hour, or at least about 200 kg/hour, or at least about 300 kg/hour, or at least about 400 kg/hour, or at least about 500 kg/hour, or at least about 600 kg/hour, or at least about 700 kg/hour, or at least about 800 kg/hour, or at least about 900 kg/hour, or at least about 1000 kg/hour, or at least about 1200 kg/hour, or at least about 1400 kg/hour, or at least about 1600 kg/hour, or at least about 1800 kg/hour, or at least about 2000 kg/hour, or at least about 2200 kg/hour. In some embodiments, a feeding rate may be from about 10 kg/hour to about 200 kg/hour, or from about 200 kg/hour to about 400 kg/hour, or from about 400 kg/hour to about 600 kg/hour, or from about 600 kg/hour to about 800 kg/hour, or from about 800 kg/hour to about 1000 kg/hour, or from about 1000 kg/hour to about 1200 kg/hour, or from about 1200 kg/hour to about 1400 kg/hour, or from about 1400 kg/hour to about 1600 kg/hour, or from about 1600 kg/hour to about 1800 kg/hour, or from about 1800 kg/hour to about 2000 kg/hour, or from about 2000 kg/hour to about 2200 kg/hour.

Chemical methods may be employed, in some embodiments, (e.g., alone or in combination with mechanical methods) to lyse a biomass or a washed biomass. According to some embodiments, an amphiphilic compound may be employed to lyse a biomass or a washed biomass. In some embodiments, an amphiphilic chemical compound may comprise lecithin. Enzymes (e.g., cellulase) may be used, in some embodiments to breakdown or assist in breakdown of cellular structures. In some embodiments lysing may be performed, for example, by changing a pH value of a biomass (e.g., harvested microcrop). A pH value, in some embodiments, may be raised to higher than about 7.0, or higher than about 7.5, or higher than about 8.0, or higher than about 8.5, or higher than about 9.0, or higher than about 9.5, or higher than about 10.0. According to some embodiments, a pH value of a biomass may be maintained from about 7.0 to about 7.5, or from about 7.5 to about 8.0, or from about 8.0 to about 8.5, or from about 8.5 to about 9.0, or from about 9.0 to about 9.5, or from about 9.5 to about 10.0. A pH value of a biomass may be maintained from about 7.0 to about 14.0, or from about 7.0 to about 13.0, or from about 7.0 to about 12.0, or from about 7.0 to about 11.0, or from about 7.0 to about 10.0, or from about 7.0 to about 10.5, or from about 7.0 to about 9.5, or from about 7.0 to about 9.0, or from about 7.0 to about 8.5, or from about 7.0 to about 8.0, or from about 7.0 to about 7.5, in some embodiments. In some embodiments a pH value may be lowered to below about 7.0, or below about 6.5, or below about 6.0, or below about 5.5, or below about 5.0, or below about 4.5, or below about 4.0, or below about 3.5, or below about 3.0. A pH value of a biomass, in some embodiments, may be maintained from about 3.0 to about 3.5, or from about 3.5 to about 4.0, or from about 4.0 to about 4.5, or from about 4.5 to about 5.0, or from about 5.0 to about 5.5, or from about 5.5 to about 6.0, or from about 6.0 to about 6.5, or from about 6.5 to about 7.0. A pH value of a biomass may be maintained from about 3.0 to about 7.0, or from about 3.5 to about 7.0, or from about 4.0 to about 7.0, or from about 4.5 to about 7.0, or from about 5.0 to about 7.0, or from about 5.5 to about 7.0, or from about 6.0 to about 7.0, or from about 6.5 to about 7.0, according to some embodiments.

In some embodiments, a lysed biomass (e.g., a mechanically lysed biomass) may pass to a next step or procedure for isolating protein and/or other product(s) with or without neutralization. For example, a lysed biomass may be fed directly to a next procedure or it may be first pH-adjusted (e.g., neutralized). Precipitating agents (e.g., salts) may be added, in some embodiments, to a lysed microcrop to precipitate dissolved compounds.

A lysed biomass (e.g., first portion, second portion) may be at a temperature below room temperature (e.g., about 12° C.), in some embodiments. Cooling a lysed biomass may improve protein recovery efficiency and/or decrease proteolytic activity. A lysed biomass, in some embodiments, may have a temperature below about 30° C., or below about 20° C., or below about 15° C., or below about 10° C., or below about 15° C., or below about 10° C., or below about 5° C., or below about 2° C., or below about 1° C., or below about 0° C. at a time of use. According to some embodiments, a lysed biomass may have a temperature between about 0° C. and about 10° C., or between about 5° C. and about 15° C., or between about 10° C. and about 20° C., or between about 15° C. and about 25° C., or between about 20° C. and about 30° C. at a time of use.

In some embodiments, a lysed biomass (e.g., first portion, second portion) may have a temperature above room temperature (e.g., about 50° C.) at a time of use. Heating a lysed biomass may improve protein recovery efficiency, decrease proteolytic activity (e.g., denature proteolytic enzymes), and/or decrease microbial contamination (e.g., pasteurization). In some embodiments, a lysed biomass may have a temperature above about 20° C., or above about 25° C., or above about 30° C., or above about 35° C., or above about 40° C., or above about 45° C., or above about 50° C., or above about 55° C., or above about 60° C., or above about 65° C., or above about 70° C., or above about 75° C., or above about 80° C., or above about 85° C., or above about 90° C. at a time of use. A lysed biomass may have a temperature between about 40° C. and about 50° C., or between about 45° C. and about 55° C., or between about 50° C. and about 60° C. at a time of use, in some embodiments. According to some embodiments, a lysed biomass may have a temperature between about 75° C. and about 80° C., or between about 80° C. and about 85° C. at a time of use.

Separating a Biomass

A biomass (e.g., *Lemna*), washed biomass, lysed biomass, or any combination thereof may be separated to generate a juice fraction and a solid fraction. A juice fraction (e.g., first portion, second portion) may include a protein-rich liquid and/or at least about some solid particles (e.g., carbohydrates, fiber). In some embodiments a biomass (e.g., washed, lysed) may be diluted with a dilution fluid (e.g., water, recycled water, reverse osmosis water) prior to separation.

A dilution fluid may be at a temperature below room temperature (e.g., about 12° C.), in some embodiments. Cooling a dilution fluid may improve protein recovery efficiency and/or decrease proteolytic activity. A dilution fluid, in some embodiments, may have a temperature below about 30° C., or below about 20° C., or below about 15° C., or below about 10° C., or below about 5° C., or below about 2° C., or below about 1° C., or below about 0° C. at a time of use. According to some embodiments, a dilution fluid may have a temperature between about 0° C. and about 10° C., or between about 5° C. and about 15° C., or between about 10° C. and about 20° C., or between about 15° C. and about 25° C., or between about 20° C. and about 30° C. at a time of use.

In some embodiments, a dilution fluid may have a temperature above room temperature (e.g., about 50° C.) at a time of use. Heating a dilution fluid may improve protein recovery efficiency, decrease proteolytic activity (e.g., denature proteolytic enzymes), and/or decrease microbial contamination (e.g., pasteurization). In some embodiments, a dilution fluid may have a temperature above about 20° C., or above about 25° C., or above about 30° C., or above about 35° C., or above about 40° C., or above about 45° C., or above about 50° C., or above about 55° C., or above about 60° C., or above about 65° C., or above about 70° C., or above about 75° C., or above about 80° C., or above about 85° C., or above about 90° C. at a time of use. A dilution fluid may have a temperature between about 40° C. and about 50° C., or between about 45° C. and about 55° C., or between about 50° C. and about 60° C., or between about 75° C. and about 80° C., or between about 80° C. and about 85° C. at a time of use, in some embodiments.

A dilution fluid, in some embodiments, may include buffers, protease inhibitors, anti-microbial agents, chelators (e.g., EDTA), reducing agents, or any combination thereof. In some embodiments a lysed biomass or diluted lysed biomass may be sonicated prior to separation. Sonication may increase protein yield.

Separating a biomass (e.g., washed, lysed) to form a juice fraction and a solid fraction may involve pressing (e.g., belt press, filter press), centrifugation, filtration, pressurized filtration, or any combination thereof. Interchangeable unit operations for separating a biomass (e.g., harvested microcrop), washed biomass, and/or lysed biomass include, for example, a decanter centrifuge, a belt press, a fan press, a rotary press, a screw press, a filter press, a finisher press, or any combination thereof.

In some embodiments, a biomass (e.g., harvested microcrop), a washed biomass, a lysed biomass, or any combination thereof may be metered to a separating mechanism at any desired volume, mass, or other rate or interval (e.g., a constant rate, a variable rate, continuously, semi-continuously, periodically, intermittently). A feed rate and/or mode may be determined based on considerations including, for example: a target production rate; apparatus(es) employed in a process; properties of a feedstock; or any combination thereof. A feeding rate, in some embodiments, may be at least about 10 kg/hour, or at least about 50 kg/hour, or at least about 100 kg/hour, or at least about 200 kg/hour, or at least about 300 kg/hour, or at least about 400 kg/hour, or at least about 500 kg/hour, or at least about 600 kg/hour, or at least about 700 kg/hour, or at least about 800 kg/hour, or at least about 900 kg/hour, or at least about 1000 kg/hour, or higher than about 1000 kg/hour. According to some embodiments, a feeding rate may be from about 10 kg/hour to about 200 kg/hour, or from about 200 kg/hour to about 400 kg/hour, or from about 400 kg/hour to about 600 kg/hour, or from about 600 kg/hour to about 800 kg/hour, or from about 800 kg/hour to about 1000 kg/hour, or from about 1000 kg/hour to about 1200 kg/hour, or from about 1200 kg/hour to about 1400 kg/hour, or from about 1400 kg/hour to about 1600 kg/hour, or from about 1600 kg/hour to about 1800 kg/hour, or from about 1800 kg/hour to about 2000 kg/hour, or from about 2000 kg/hour to about 2200 kg/hour.

Separating a biomass may be performed at any desired temperature. Separating may be performed at temperatures below room temperature, for example, to decrease proteolytic activity. In some embodiments, separating may be performed at a temperature below about 40° C., below about 30° C., or below about 20° C., or below about 15° C., or below about 10° C., or below about 5° C., or below about 2° C., or below about 1° C., or below about 0° C. Separating may be performed, for example, at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C.

Separating a Solid Fraction

In some embodiments, a solid fraction may be further separated to extract additional juice (e.g., a second juice (FIG. 3A, 332)). Separation of a solid fraction (e.g., first portion, second portion) may form a second juice (e.g., FIG. 3A, 332) and a first solid (e.g., FIG. 3A, 331). A second juice (e.g., first portion, second portion) may include a protein-rich liquid and/or at least some solid particles (e.g., carbohydrates, fiber).

Separating a solid fraction to form a second juice and a first solid may involve pressing (e.g., screw press), centrifugation, filtration, pressurized filtration, or any combination thereof. Interchangeable unit operations for separating a solid fraction include, for example, a decanter centrifuge, a belt press, a fan press, a rotary press, a screw press, a filter press, a finisher press, or any combination thereof.

In some embodiments, a solid fraction may be metered to a separating mechanism at any desired volume, mass, or other rate or interval (e.g., a constant rate, a variable rate, continuously, semi-continuously, periodically, intermittently). A feed rate and/or mode may be determined based on considerations including, for example: a target production rate; apparatus(es) employed in a process; properties of a feedstock; or any combination thereof. A feeding rate, in some embodiments, may be at least about 10 kg/hour, or at least about 50 kg/hour, or at least about 100 kg/hour, or at least about 200 kg/hour, or at least about 300 kg/hour, or at least about 400 kg/hour, or at least about 500 kg/hour, or at least about 600 kg/hour, or at least about 700 kg/hour, or at least about 800 kg/hour, or at least about 900 kg/hour, or at least about 1000 kg/hour, or higher than about 1000 kg/hour. According to some embodiments, a feeding rate may be from about 10 kg/hour to about 200 kg/hour, or from about 200 kg/hour to about 400 kg/hour, or from about 400 kg/hour to about 600 kg/hour, or from about 600 kg/hour to about 800 kg/hour, or from about 800 kg/hour to about 1000 kg/hour, or higher than about 1000 kg/hour, or from about 1000 kg/hour to about 1200 kg/hour, or from about 1200 kg/hour to about 1400 kg/hour, or from about 1400 kg/hour to about 1600 kg/hour, or from about 1600 kg/hour to about 1800 kg/hour, or from about 1800 kg/hour to about 2000 kg/hour, or from about 2000 kg/hour to about 2200 kg/hour.

Separating a solid fraction may be performed at any desired temperature. Separating may be performed at temperatures below room temperature, for example, to decrease proteolytic activity and/or microbial growth. In some embodiments, separating may be performed at a temperature below about 40° C., below about 30° C., or below about 20° C., or below about 15° C., or below about 10° C., or below about 5° C., or below about 2° C., or below about 1° C., or below about 0° C. Separating may be performed, for example, at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C.

In some embodiments, a separation apparatus (e.g., screw press) selected to separate a solid fraction may be the same apparatus used to separate a biomass (e.g., lysed) to form a juice fraction and a solid fraction. A separation apparatus (e.g., screw press) selected to separate a solid fraction may be a different apparatus than that used to separate (e.g., decanter centrifuge) a biomass (e.g., lysed) to form a juice fraction and a solid fraction, in some embodiments. In some embodiments, a separation apparatus (e.g., screw press) may be used multiple times to extract additional second juice from a solid fraction.

According to some embodiments, a process for growing, harvesting, and separating a microcrop (e.g., photosynthetic aquatic species, aquatic plant species, *Lemna*, algal species) may be single cycle, and at least one of a first cake (e.g., FIG. 3, 342) and a second cake (e.g., FIG. 3, 347) which are collected at other stages in a cycle (e.g., separation of a juice fraction yields a first cake) may be combined with a first solid to form a solid mixture, and the solid mixture may be further processed (e.g., FIG. 2A, FIG. 2B, FIG. 3A, FIG. 3B).

In some embodiments a process for growing, harvesting, and separating a microcrop (e.g., aquatic plant species, *Lemna*, algal species) may be multiple cycles or a continuous process such that one or more of a first cake (e.g., FIG. 4, 442) and a second cake (e.g., FIG. 4, 447) that are collected in an earlier cycle may be combined with a solid fraction from a subsequent cycle prior to separation (e.g., FIG. 4, 430) of the solid fraction.

Increasing an extraction of a second juice from a solid fraction may decrease an overall moisture content of a first solid and may thereby lower an energy expenditure required to further process the first solid (e.g., energy required to dry). Additionally, increasing an extraction of juice from a solid fraction and/or solid mixture may improve a yield of a protein-rich product.

In some embodiments, a moisture content of a solid fraction and/or solid mixture is less than about 90%, or less than about 80%, or less than about 70%, or less than about 60%, or less than about 50%, or less than about 40%, or less than about 30%, or less than about 20%, or less than about 10% by weight.

Separating a Juice Fraction

A juice fraction (e.g., first portion, second portion) may be separated to generate a first juice and a first cake, according to some embodiments. A first juice (e.g., first portion, second portion) may include a dissolved protein. In some embodiments, buffers, protease inhibitors, anti-microbial agents, chelators (e.g., EDTA), reducing agents, or any combination thereof may be added to a juice fraction and/or a first juice. Separating a juice fraction, in some embodiments, may include centrifugation, filtration, pressurized filtration, or any combination thereof. Two or more unit operations (e.g., interchangeable unit operations) may be used to separate a juice fraction including, for example, a high-speed disc stack centrifuge, a circular vibratory separator, a linear/inclined motion shaker, a decanter centrifuge, a filter press, pressurized filtration mechanisms, microfiltration, vacuum filtration, or any combination thereof.

Microfiltration may be used, in some embodiments, to separate a juice fraction into a first juice and a first cake. In some embodiments, suitable filter sizes may include ≤about 10 µm, or ≤about 5 µm, or ≤about 3 µm, or ≤about 2 µm, or ≤about 1 µm, or ≤about 0.5 µm, or ≤about 0.4 µm, or ≤about 0.3 µm, or ≤about 0.2 µm, or ≤about 0.1 µm. A filter may have a filter size of not less than about 0.1 µm, in some embodiments. Microfiltration may reduce a concentration of suspended solids (e.g., fats, fiber), microbial contamination (e.g., *Escherichia coli*), and/or fungal contamination (e.g., yeast) in a first juice, according to some embodiments.

In some embodiments, a vacuum may be implemented during at least some of a separating process.

Separating may be performed, according to some embodiments, at temperatures below room temperature, for example, to decrease proteolytic activity. In some embodiments separating may be performed at a temperature below about 40° C., or below about 30° C., or below about 20° C., or below about 15° C., or below about 10° C., or below about 5° C., or below about 2° C., or below about 1° C., or below about 0° C. Separating may be performed at a temperature between about 0° C. and about 10° C., or between about 5° C. and about 15° C., or between about 10° C. and about 20° C., or between about 15° C. and about 25°

C., or between about 20° C. and about 30° C., or between about 25° C. and about 35° C., or between about 30° C. and about 40° C., in some embodiments.

A first juice may be pumped into a storage tank, for example, a chilled storage tank, until further processing. In some embodiments a chilled storage tank may be maintained at a temperature below room temperature (e.g., 12° C.). Storage of a first juice at a low temperate may reduce proteolytic activity and thereby improve protein recovery efficiency. A chilled storage tank, in some embodiments, may be maintained at a temperature below about 30° C., or below about 20° C., or below about 15° C., or below about 10° C., or below about 5° C., or below about 2° C., or below about 1° C., or below about 0° C. According to some embodiments, a chilled storage tank may be maintained at a temperature of about 5° C., about 6° C., about 7° C., about 8° C., about 9° C., about 10° C., about 11° C., about 12° C., about 13° C., about 14° C., or about 15° C. In some embodiments, a first juice may be fed directly to further processing without being stored in a storage tank.

Any one or more liquid phases (e.g., a juice fraction, a first juice, a second juice, a third juice) or solid phases (e.g., a solid fraction, a first cake, a second cake) generated in one procedure may be stored in a storage tank before being fed to one or more downstream procedures or apparatuses. In some embodiments a homogeneous liquid phase or solid phase may be generated for a downstream procedure(s) or apparatus(es). This may accommodate different operation schedules or modes including, for example, continuous mode, batch mode, or multiple feeding streams to one or more downstream procedure(s) and/or apparatus(es). A liquid phase or solid phase may be maintained in a storage tank at a desirable temperature (e.g., below room temperature, such as 12° C.) to reduce degradation and maintain high quality until further processing.

Separating a First Cake and/or a Second Juice

In some embodiments, further processing of a first cake (e.g., first portion, second portion) and a second juice (e.g., first portion, second portion) may be performed. Such additional processing may increase product yield and/or quality. In some embodiments, a first cake and a second juice may be combined and further separated to form a third juice and a second cake. A first cake and a second juice may be independently subjected to further separation, according to some embodiments.

Separating a first cake, a second juice, or any combination thereof may involve vibratory separation, centrifugation, filtration, pressurized filtration, or any combination thereof. Several different interchangeable unit operations may be used to separate including, for example, a high-speed disc stack centrifuge, a circular vibratory separator, a linear/inclined motion shaker, a decanter centrifuge, a filter press, pressurized filtration mechanisms, microfiltration, vacuum filtration, or any combination thereof.

In some embodiments, filtration (e.g., a vibratory separator) may be used to separate a first cake, a second juice, or any combination thereof to form a third juice and a second cake. Suitable filter sizes may include, in some embodiments, ≤about 800 µm, or ≤about 600 µm, or ≤about 500 µm, or ≤about 400 µm, or ≤about 300 µm, or ≤about 200 µm, or ≤about 180 µm, or ≤about 150 µm, or ≤about 120 µm, or ≤about 100 µm, or ≤about 90 µm, or ≤about 80 µm, or ≤about 70 µm, or ≤about 60 µm, or ≤about 50 µm, or ≤about 40 µm, or ≤about 30 µm, or ≤25 µm, or ≤about 20 µm, or ≤about 15 µm, or ≤about 10 µm, or ≤about 5 µm, or ≤about 1 µm. A filter may have a filter size of not more than about 800 µm, in some embodiments. Pore size of a filter may be selected larger or smaller as desired. For example, a larger pore size may be desirable where removal of contaminant material is of interest. A smaller pore size may be desirable where limiting a number of cycles of a process and/or protein yield is of interest. In some embodiments, a pore size of a filter may be selected based on lysing conditions, for example, an average particle size of a lysed biomass. A pore size of a filter may be selected based on one or more characteristics of a microcrop (e.g. cell wall composition, protein composition), according to some embodiments.

Microfiltration may be used, in some embodiments, to separate a first cake, a second juice, or any combination thereof to form a third juice and a second cake. In some embodiments, suitable filter sizes may include ≤about 10 µm, or ≤about 5 µm, or ≤about 3 µm, or ≤about 2 µm, or ≤about 1 µm, or ≤about 0.5 µm, or ≤about 0.4 µm, or ≤about 0.3 µm, or ≤about 0.2 µm, or ≤about 0.1 µm. A microfilter may have a filter size of not less than about 0.1 µm, in some embodiments.

In some embodiments, a vacuum may be implemented during at least some of separating process.

Separating may be performed, according to some embodiments, at temperatures below room temperature, for example, to decrease proteolytic activity. In some embodiments separating may be performed at a temperature below about 40° C., or below about 30° C., or below about 20° C., or below about 15° C., or below about 10° C., or below about 5° C., or below about 2° C., or below about 1° C., or below about 0° C. Separating may be performed at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C., in some embodiments.

According to some embodiments, a process for growing, harvesting, and separating a microcrop (e.g., aquatic plant species, *Lemna, algal* species) may comprise a single cycle. In a single cycle process, in some embodiments, at least one of a first cake (e.g., FIG. 3, 342) and a second cake (e.g., FIG. 3, 347) may be combined with a first solid to form a solid mixture, and the solid mixture may be further processed (e.g., FIG. 2A, FIG. 2B, FIG. 3A, FIG. 3B). In some embodiments of a single cycle process, a third juice may be combined with a first juice prior to further processing.

In some embodiments a process for growing, harvesting, and separating a microcrop (e.g., aquatic plant species, *Lemna, algal* species) may comprise multiple cycles (e.g., a continuous process). In a multiple cycle or continuous process, according to some embodiments, one or more of a first cake (e.g., FIG. 4, 442) and a second cake (e.g., FIG. 4, 447) that are collected in an earlier cycle may be combined with a solid fraction from a subsequent cycle prior to separation (e.g., FIG. 4, 430) of the solid fraction. In some embodiments of a multiple cycle or continuous process a third juice collected in an earlier cycle may be combined with a juice fraction from a subsequent cycle prior to further processing.

Filtering a First Juice, a Third Juice, or any Combination Thereof

A first juice (e.g., first portion, second portion), a third juice (e.g., first portion, second portion), or any combination thereof may be filtered one or more times to generate a soluble protein product (e.g., a soluble protein (e.g., FIG. 2, 251), a first soluble protein (e.g., FIG. 3, 351), a second soluble protein (e.g., FIG. 3, 356)). Filtration may involve microfiltration, ultrafiltration, nanofiltration, or reverse osmosis filtration either individually or in combination.

Microfiltration may reduce a concentration of suspended solids (e.g., fats, fiber), microbial contamination (e.g., *Escherichia coli*), and/or fungal contamination (e.g., yeast) in a first juice, a third juice, or any combination thereof, according to some embodiments. Suitable filter sizes for microfiltration may include, in some embodiments, ≤about 10 μm, or ≤about 5 μm, or ≤about 3 μm, or ≤about 2 μm, or ≤about 1 μm, or ≤about 0.5 μm, or ≤about 0.4 μm, or ≤about 0.3 μm, or ≤about 0.2 μm, or ≤about 0.1 μm. In some embodiments, a first juice, a third juice, or any combination thereof may be filtered using microfiltration to generate a soluble protein in a permeate.

Ultrafiltration may involve membrane filtration using pressure, concentration gradients, or a combination thereof. Suitable nominal molecular weight cut-offs (NMWCO) for ultrafiltration may be, in some embodiments, at most about 100 kDa, or at most about 90 kDa, or at most about 80 kDa, or at most about 70 kDa, or at most about 60 kDa, or at most about 55 kDa, or at most about 50 kDa, or at most about 45 kDa, or at most about 40 kDa, or at most about 30 kDa, or at most about 20 kDa, or at most about 15 kDa, or at most about 14 kDa, or at most about 13 kDa, or at most about 12 kDa, or at most about 11 kDa, or at most about 10 kDa, or at most about 9 kDa, or at most about 8 kDa, or at most about 7 kDa, or at most about 6 kDa, or at most about 5 kDa, or at most about 4 kDa, or at most about 3 kDa, or at most about 2 kDa, or at most about 1 kDa. In some embodiments, suitable NMWCO cut-offs for ultrafiltration may be in a range of at most about 1 kDa to at most about 10 kDa, at most about 2 kDa to at most about 10 kDa, at most about 3 kDa to at most about 10 kDa, at most about 3 kDa to at most about 15 kDa, or at most about 3 kDa to at most about 20 kDa, or at most about 3 kDa to at most about 60 kDa, or at most about 3 kDa to at most about 55 kDa, or at most about 10 kDa to at most about 55 kDa. In some embodiments a NMWCO for ultrafiltration may be at least 1 kDa, or at least 3 kDa, or at least 5 kDa, or at least 10 kDa, or at least 15 kDa, or at least 20 kDa, or at least 25 kDa, or at least 30 kDa, or at least 35 kDa, or at least 40 kDa, or at least 45 kDa, or at least 50 kDa, or at least 55 kDa. A suitable NMWCO for ultrafiltration may vary depending on a manufacturing specification of an ultrafilter. In some embodiments a suitable NMWCO for ultrafiltration may vary depending on a rate of hydrolysis.

In some embodiments, suitable filter sizes for nanofiltration may include ≤about 0.01 μm, or ≤about 0.009 μm, or ≤about 0.008 μm, or ≤about 0.007 μm, or ≤about 0.006 μm, or ≤about 0.005 μm, or ≤about 0.004 μm, or ≤about 0.003 μm, or ≤about 0.002 μm, or ≤about 0.001 μm. A nanofiltration filter may have a filter size of not more than about 0.01 μm, in some embodiments.

According to some embodiments, suitable filter sizes for reverse osmosis filtration may include ≤about 0.001 μm, ≤about 0.0009 μm, ≤about 0.0008 μm, ≤about 0.0007 μm, ≤about 0.0006 μm, ≤about 0.0005≤about 0.0004 μm, ≤about 0.0003 μm, ≤about 0.0002 μm, or ≤about 0.0001 μm. A reverse osmosis filter may have a filter size of not more than about 0.001 μm, in some embodiments.

Buffers, protease inhibitors, anti-microbial agents, chelators (e.g., EDTA), reducing agents, or any combination thereof may be added, in some embodiments, to a soluble protein product. A soluble protein product may be chilled and/or stored at a temperature below about 30° C., or below about 25° C., or below about 20° C., or below about 15° C., or below about 10° C., or below about 5° C., or below about 2° C., or below about 1° C., or below about 0° C., or below about −2° C., or below about −5° C., or below about −10° C., in some embodiments. Chilling and/or storing a soluble protein product at reduced temperatures may reduce degradation and/or improve protein recovery efficiency.

Polyphenol Reduction

Figure 2A:
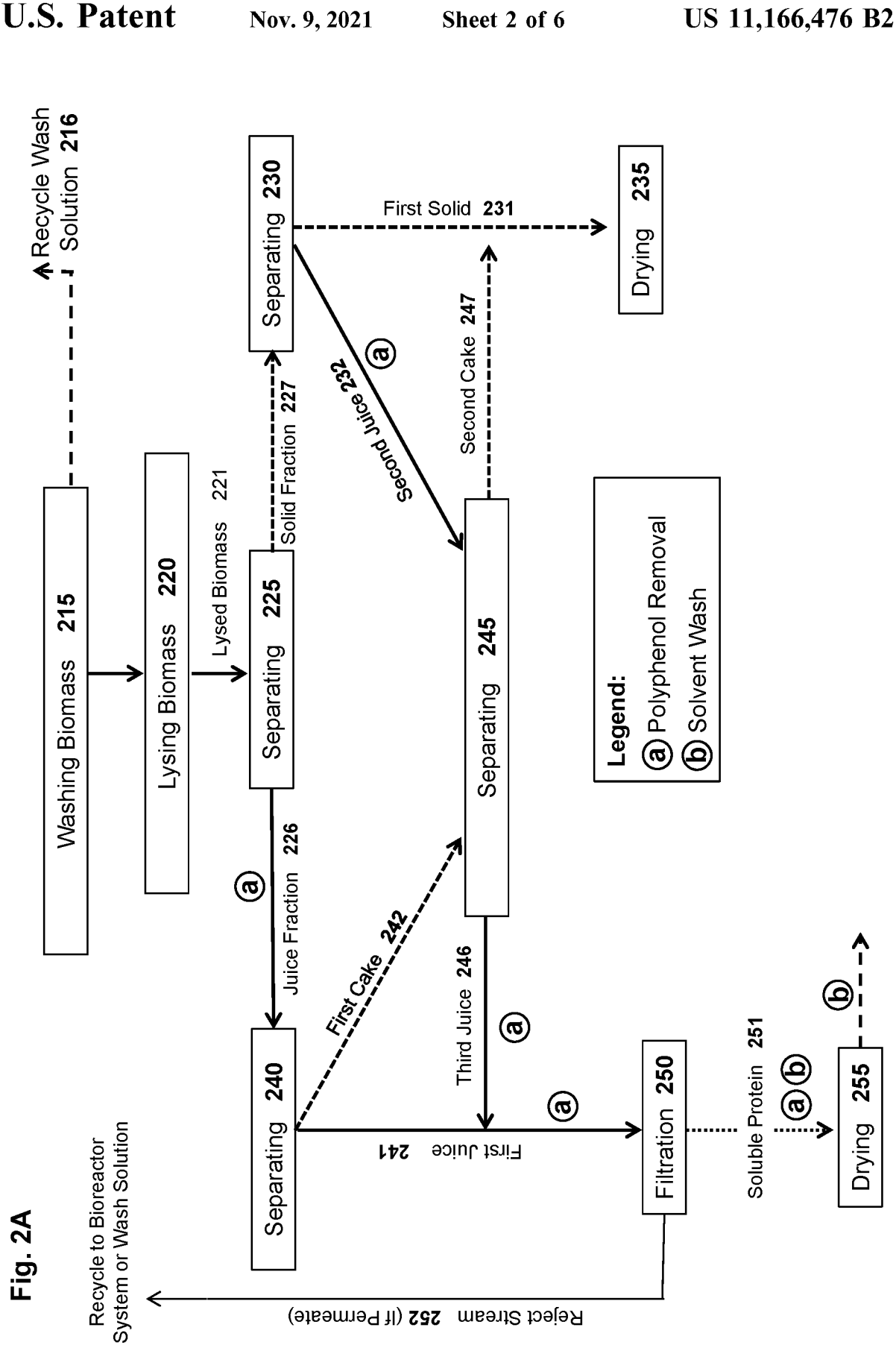
FIG. 2A is a flow diagram illustrating a process for producing a protein concentrate and/or a carbohydrate rich product from a biomass according to a specific example embodiment of the disclosure.
Figure 2B:
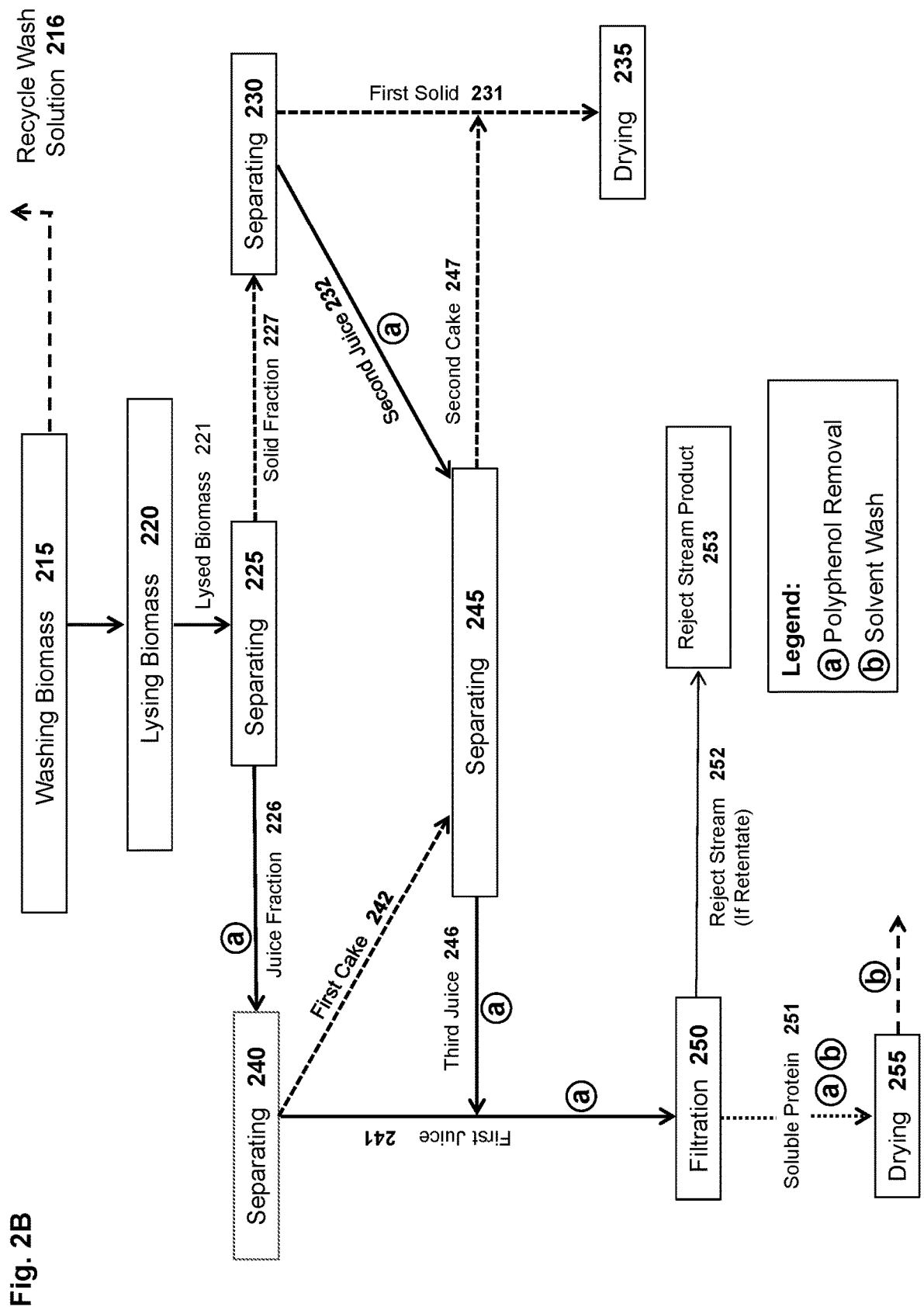
FIG. 2B is a flow diagram illustrating a process for producing a protein concentrate and/or a carbohydrate rich product from a biomass according to a specific example embodiment of the disclosure.
Figure 3A:
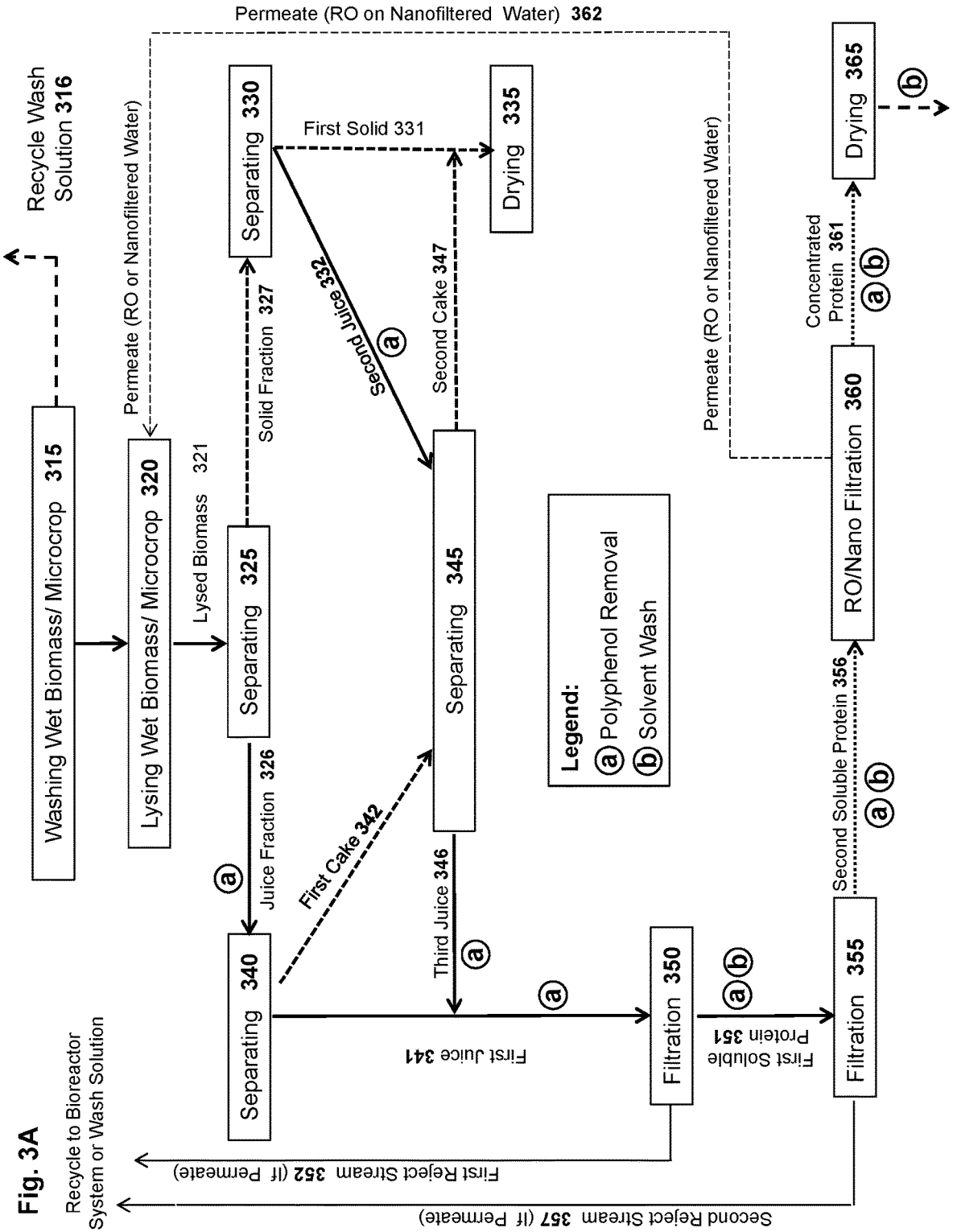
FIG. 3A is a flow diagram illustrating a process for producing a protein concentrate and/or a carbohydrate rich product from a biomass according to a specific example embodiment of the disclosure.
Figure 3B:
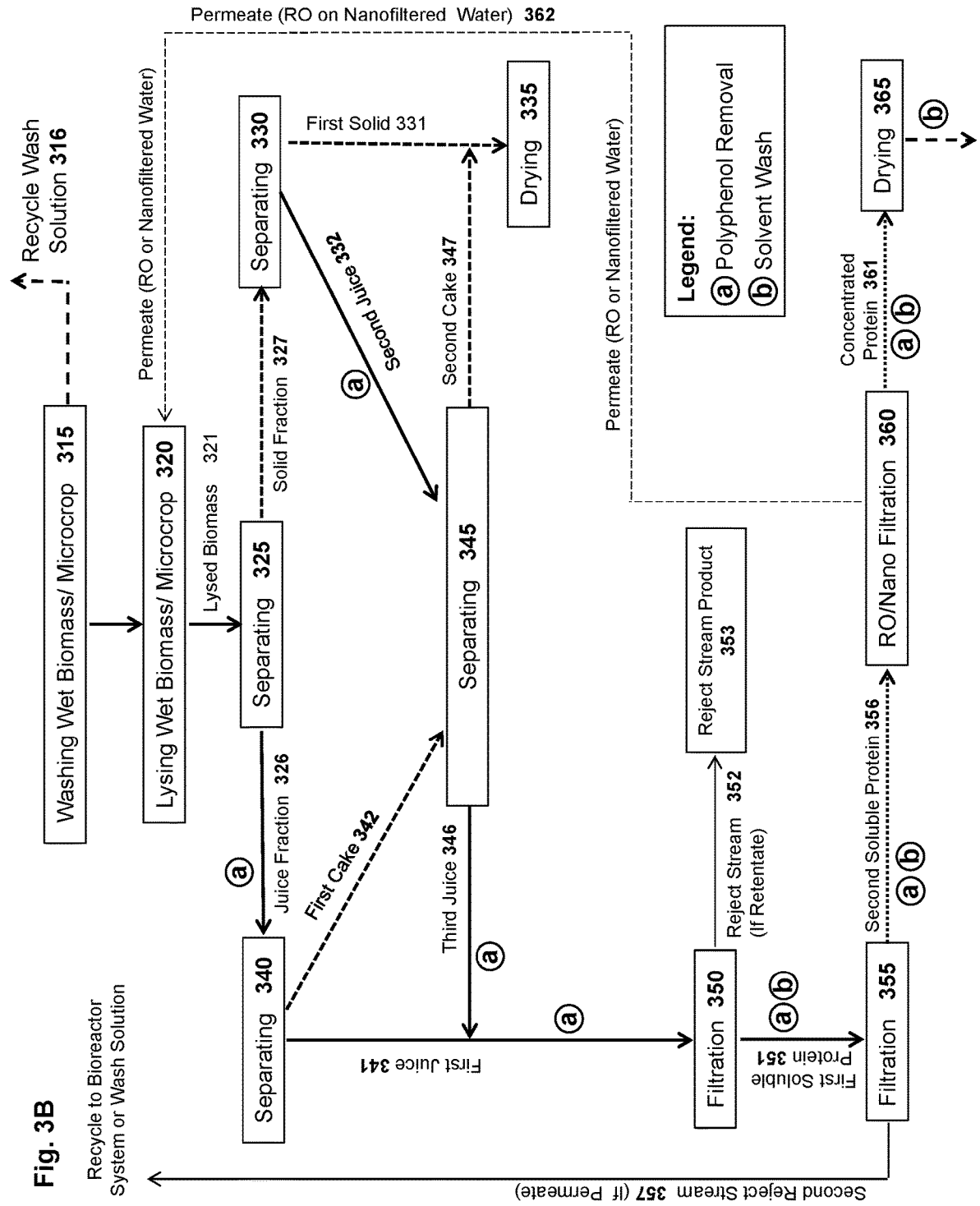
FIG. 3B is a flow diagram illustrating a process for producing a protein concentrate and/or a carbohydrate rich product from a biomass according to a specific example embodiment of the disclosure.

In some embodiments, a polyphenol-rich product may be subjected to a polyphenol reduction process to generate a product having a reduced concentration of at least one polyphenol (e.g., a tannin). A polyphenol-rich product may include, according to some embodiments, a juice fraction (e.g., FIG. 1, 126), a soluble protein (e.g., FIG. 2A, 251; FIG. 2B, 251), a first soluble protein (e.g., FIG. 3A, 351; FIG. 3B, 351, FIG. 4, 451), a second soluble protein (e.g., FIG. 3A, 356; FIG. 3B, 356; FIG. 4, 456) FIG. 3B, 375, FIG. 4, 475), a concentrated protein (e.g., FIG. 3A, 361; FIG. 3B, 361; FIG. 4, 461), a first juice (e.g., FIG. 2A, 241; FIG. 2B, 241; FIG. 3A, 341; FIG. 3B, 341, FIG. 4, 441), a second juice (e.g., FIG. 2A, 232; FIG. 2B, 232; FIG. 3A, 332; FIG. 3B, 332, FIG. 4, 432), a third juice (e.g., FIG. 2A, 246; FIG. 2B, 246; FIG. 3A, 346; FIG. 3B, 346, FIG. 4, 446), a juice fraction (e.g., FIG. 1, 126; FIG. 2A, 226; FIG. 2B, 226; FIG. 3A, 326; FIG. 3B, 326, FIG. 4, 426), or any combination thereof. A polyphenol reduction process may be configured to reduce a concentration of at least one polyphenol (e.g., at least one tannin), according to some embodiments. A polyphenol reduction process may be configured, in some embodiments, to minimize a reduction in yield or quality of a downstream soluble protein product.

According to some embodiments a polyphenol reduction process may comprise passing a polyphenol-rich product through an ion exchange resin. In some embodiments, a polyphenol reduction process may comprise passing a polyphenol-rich product through a series (e.g., at least two, at least three) of ion exchange resins. Each ion exchange resin in a series may be the same or different than the other ion exchange resins in the series. In some embodiments an ion exchange resin may be a strongly acidic resin, a strongly basic resin (e.g., DIAION PA308), a weakly acidic resin (e.g., Relite JA800), a weakly basic resin, a weak anion exchange resin (e.g., Relite RAM2), a strong anion exchange resin, a weak cation exchange resin, a strong cation exchange resin, or any combination thereof. According to some embodiments a polyphenol reduction process may comprise passing a polyphenol-rich product through an ion exchange column selected from a weakly acidic resin (e.g., Relite JA800), an anion exchange resin (e.g., Relite RAM2), a strongly basic resin (e.g., DIAION PA308), or a combination thereof. A polyphenol reduction process, in some embodiments, may comprise: first passing a polyphenol-rich product: through an ion exchange column selected from a weak anion exchange and a strong anion exchange resin, and second passing the polyphenol-rich product through an ion exchange column selected from a weak anion exchange resin and a strong anion exchange resin. Ion exchange resins may be used in a batch mode or arranged in a continuous process, whereby resins may be cycled through polyphenol extraction and regeneration processes. In some embodiments a polyphenol reduction process may further comprise adjusting a pH of a polyphenol-rich product or a product yielded from an ion exchange column. A polyphenol reduction process may be performed alone or in combination with other purification processes and/or steps.

In some embodiments a polyphenol reduction process may reduce a polyphenol (e.g., a tannin) content of a polyphenol-rich product by at least 5%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%. A polyphenol reduction process, according to some embodiments, may reduce a polyphenol content of a polyphenol-rich product from about 5% to about 10%, from about 15% to about 20%, from about 20% to about 30%, from about 30% to about 40%, from about 35% to about 45%, from about 40% to about 50%, from about 45% to about 55%, from about 50% to about 60%, from about 55% to about 65%, or from about 60% to about 70%.

In some embodiments, a soluble protein product (e.g., a soluble protein, a first soluble protein, a second soluble protein), may comprise polyphenol (e.g., total polyphenol) at a concentration of about 0.05 g/100 g of soluble protein product, about 0.1 g/100 g of soluble protein product, about 0.5 g/100 g of soluble protein product, about 1 g/100 g of soluble protein product, about 5 g/100 g of soluble protein product, about 10 g/100 g of soluble protein product, and about 20 g/100 g of protein concentrate. According to some embodiments, based on analysis of a pasteurized product, a 100 g of a final product may contain about 65 g of protein and about 1.092 g polyphenols (expressed as gallic acid equivalents).

Reducing a Moisture Content of Soluble Protein Products

In some embodiments a process may be used to reduce a moisture content of a soluble protein (e.g., FIG. 2, 251), a first soluble protein (e.g., FIG. 3, 351), a second soluble protein (e.g., FIG. 3, 356), or any combination thereof (collectively "a soluble protein product"). Reducing a moisture content of a soluble protein product may reduce capital and operational expenditures, for example, by reducing an energy needed to dry an end protein product (e.g., concentrated soluble protein).

In some embodiments an evaporation process may be used to reduce a moisture content of a soluble protein product. Evaporation may be performed by, for example, a thermal (evaporative) means such as: a rising film evaporator, a falling film evaporator, a natural circulation evaporator (vertical or horizontal), an agitated-film evaporator, a multiple-effect evaporator, by vacuum evaporation, or any combination thereof. Heat may be supplied directly into an evaporator, or indirectly through a heat jacket. Heat may either come from a raw source (e.g., combustion of natural gas, steam from a boiler) or from a waste heat stream (e.g., dryer exhaust) or from heat transferred by cooling an input stream.

A moisture content of a soluble protein product (e.g., a soluble protein, a second soluble protein) may be reduced, in some embodiments, by nanofiltration or reverse osmosis filtration. In some embodiments, suitable filter sizes for nanofiltration may include ≤about 0.01 μm, or ≤about 0.009 μm, or ≤about 0.008 μm, or ≤about 0.007 μm, or ≤about 0.006 μm, or ≤about 0.005 μm, or ≤about 0.004 μm, or ≤about 0.003 μm, or ≤about 0.002 μm, or ≤about 0.001 μm. A moisture content of a soluble protein product (e.g., a soluble protein, a second soluble protein) may be reduced, in some embodiments, using nanofiltration with a soluble protein product (e.g., a soluble protein, a second soluble protein) in a retentate. According to some embodiments, suitable filter sizes for reverse osmosis filtration may include ≤about 0.001 μm, ≤about 0.0009 μm, ≤about 0.0008 μm, ≤about 0.0007 μm, ≤about 0.0006 μm, ≤about 0.0005≤about 0.0004 μm, ≤about 0.0003 μm, ≤about 0.0002 μm, or ≤about 0.0001 μm. A moisture content of a soluble protein product (e.g., a soluble protein, a second soluble protein), in some embodiments, may be reduced using reverse osmosis filtration with a soluble protein product in a retentate. A permeate of nanofiltration or reverse osmosis filtration may be recycled (e.g., dilution fluid for lysis; wash solution), according to some embodiments.

In some embodiments an antioxidant (e.g., rosemary extract) may be mixed with a soluble protein product (e.g., a soluble protein, a second soluble protein) prior to drying to improve shelf life of product when packaged.

Drying a Soluble Protein Product

A soluble protein product (e.g., a soluble protein, a first soluble protein, a second soluble protein) may be dried to generate a dry protein concentrate (e.g., first portion, second portion), according to some embodiments. A drying procedure, in some embodiments, may reduce a moisture content of a soluble protein product to a desired level (e.g., higher or lower moisture content, a desired moisture content). A moisture content of a dry protein concentrate may be, for example, below 90%, or below about 80%, or below about 70%, or below about 60%, or below about 50%, or below about 40%, or below about 30%, or below about 20%, or below about 10%, or below about 5%, or below about 1% by weight of the dry protein concentrate, in some embodiments. According to some embodiments, a protein concentration of a dry protein concentrate may be from about 30% to about 95%, or from about 40% to about 90%, or from about 50% to about 85%, or from about 60% to about 80%, or from about 70% to about 75% by weight of the dry protein concentrate. A drying procedure may be performed using a mechanism including, for example, a spray dryer, double drum dryer, flash dryer, an evaporator, or any combination thereof.

In some embodiments, an inlet temperature of a dryer mechanism (a temperature at an entrance to a dryer) may be above 25° C., or above 50° C., or above 75° C., or above 100° C., or above 125° C., or above 150° C., or above 175° C., or above 200° C., or above 225° C., or above 250° C., or above 275° C., or above 300° C., or above 325° C., or above 350° C., or above 375° C., or above 400° C., or above 425° C., or above 450° C., or above 475° C., or above 500° C. An inlet temperature, in some embodiments, may be from about 25° C. to about 50° C., or from about 50° C. to about 75° C., or from about 75° C. to about 100° C., or from about 100° C. to about 125° C., or from about 125° C. to about 150° C., or from about 150° C. to about 175° C., or from about 175° C. to about 200° C., or from about 200° C. to about 225° C., or from about 225° C. to about 250° C., or from about 250° C. to about 275° C., or from about 275° C. to about 300° C., or from about 300° C. to about 325° C., or from about 325° C. to about 350° C., or from about 350° C. to about 375° C., or from about 375° C. to about 400° C., or from about 400° C. to about 425° C., or from about 425° C. to about 450° C., or from about 450° C. to about 475° C., or from about 475° C. to about 500° C., or above 500° C. An inlet temperature may be from about 50° C. to about 100° C., or from about 100° C. to about 150° C., or from about 150° C. to about 200° C., or from about 200° C. to about 250° C., or from about 250° C. to about 300° C., or from about 300° C. to about 350° C., or from about 350° C. to about 400° C., or from about 400° C. to about 450° C., or from about 450° C. to about 500° C., or above 500° C., in some embodiments. According to some embodiments, an inlet temperature of a dryer mechanism may be about 225° C.

According to some embodiments, an outlet temperature of a dryer mechanism (a temperature at an exit from a dryer) may be below about 300° C., or below about 275° C., or below about 250° C., or below about 225° C., or below about 200° C., or below about 175° C., or below about 150° C., or below about 125° C., or below about 100° C., or below about 75° C., or below about 50° C., or below about 25° C. An outlet temperature may be from about 300° C. to about 275° C., or from about 275° C. to about 250° C., or from about 250° C. to about 225° C., or from about 225° C. to about 200° C., or from about 200° C. to about 175° C., or from about 175° C. to about 150° C., or from about 150° C. to about 125° C., or from about 125° C. to about 100° C., or from about 100° C. to about 75° C., or from about 75° C. to about 50° C., or from about 50° C. to about 25° C., or below about 25° C., in some embodiments. An outlet temperature, in some embodiments, may be from about 300° C. to about 250° C., or from about 250° C. to about 200° C., or from about 200° C. to about 150° C., or from about 150° C. to about 100° C., from about 100° C. to about 50° C., or from about 50° C. to about 25° C., or below about 25° C. According to some embodiments, an outlet temperature of a dryer mechanism may be about 75° C.

In some embodiments, a volume of a soluble protein product (e.g., a soluble protein, a first soluble protein, a second soluble protein) may be mixed with a volume of a dry protein concentrate prior to drying. This process, known as back-mixing, may be employed when, for example, a moisture content of a soluble protein exceeds a level that a dryer mechanism is capable of accepting. By back-mixing a dry protein concentrate with a soluble protein product, a total moisture content may be kept within the specifications of a dryer mechanism, thereby reducing operational costs (e.g., wear and tear on equipment).

An antioxidant (e.g., rosemary extract) may be mixed with a dry protein concentrate before packaging, according to some embodiments.

Solvent Washing a Soluble Protein Product or a Dry Protein Concentrate

A soluble protein product (e.g., a soluble protein, a first soluble protein, a second soluble protein) and/or a dry protein concentrate (e.g., first portion, second portion) may be washed with at least one solvent (e.g., ethanol, methanol) to generate a washed protein product, according to some embodiments e.g., FIG. 2A, 260; FIG. 2B, 260; FIG. 3A, 370, FIG. 3B, 370, FIG. 4, 470).

A washed protein product, in some embodiments, may have a reduced fat content (e.g., about 2% of a dry protein concentrate or less by weight) and/or a reduced chlorophyll content (e.g., visually perceivable reduction in green coloration) compared to unwashed counterparts. In some embodiments, a washed protein product may appear colorless, white, substantially white, or have reduced green coloration. A washed protein product, in some embodiments, may exhibit improved taste, color, shelf life (e.g., reduced oxidation of fats), protein density, malleability, and combinations thereof. In some embodiments, a washed protein product may be extruded to form a texturized protein product.

According to some embodiments, a solvent may comprise methanol, ethanol, acetone, hexane, dichloromethane, ethyl acetate, propanol, isopropanol, glycerol, or combinations thereof.

In some embodiments, a washed protein product may have a fat content comprising lower than about 50%, or lower than about 40%, or lower than about 30%, or lower than about 25%, or lower than about 20%, or lower than about 15%, or lower than about 10%, or lower than about 5%, or lower than about 4%, or lower than about 3%, or lower than about 2%, or lower than about 1% by weight of the washed protein product. According to some embodiments, a washed protein product may have a fat content comprising from about 1% to about 10%, or from about 10% to about 20%, or from about 20% to about 30%, or from about 30% to about 40%, or from about 40% to about 50% by weight of the protein concentrate in some embodiments.

In some embodiments, a washed protein product may have a fat content comprising about 15% of a dry protein concentrate or less by weight, about 10% of a dry protein concentrate or less by weight, about 8% of a dry protein concentrate or less by weight, about 6% of a dry protein concentrate or less by weight, about 4% of a dry protein concentrate or less by weight, about 2% of a dry protein concentrate or less by weight, about 1% of a dry protein concentrate or less by weight, about 0.5% of a dry protein concentrate or less by weight, about 0.2% of a dry protein concentrate or less by weight, or about 0.1% of a dry protein concentrate or less by weight. In some embodiments, a washed protein product may have a fat content comprising from about 0.1 to about 0.2% by weight of a dry protein concentrate.

Protein Concentrate

Some embodiments relate to a process for production of a soluble protein product (e.g., a soluble protein, a first soluble protein, a second soluble protein) and/or a dry protein concentrate (collectively "a protein concentrate") from a biomass of a harvested microcrop (e.g., aquatic plant species, *Lemna, algal* species). A process may be configured or performed to achieve any desired protein yield (e.g., maximal yield, a selected yield). In some embodiments, a protein concentration of a protein concentrate is higher than about 30%, or higher than about 40%, or higher than about 50%, or higher than 55%, or higher than about 60%, or higher than 65%, or higher than about 70%, or higher than about 75%, or higher than about 80% by weight of the protein concentrate. A remainder of a protein concentrate may include carbohydrates, fiber, fats, minerals, or any combination thereof. A protein concentrate is suitable for animal feed and/or human consumption. For example, a protein concentrate may serve as an effective replacement for protein isolates (e.g., soy, pea, whey) which are presently used in a large number of human food products either individually or as ingredients and additives. According to some embodiments, a protein composition of a protein concentrate may be in native or near native form. For example, a protein composition of a protein concentrate may include <2% denatured protein, or <4% denatured protein, <6% denatured protein, or <8% denatured protein, or <10% denatured protein, or <12% denatured protein, or <14% denatured protein, or <16% denatured protein, or <18% denatured protein, or <20% denatured protein, or <22% denatured protein, or <24% denatured protein, or <26% denatured protein, or <28% denatured protein, or <30% denatured protein.

In some embodiments, a protein concentrate may comprise one or more essential amino acids. For example, a protein concentrate may include one or more amino acids selected from leucine, isoleucine, lysine, methionine, phenylalanine, threonine, tryptophan, valine, histidine, arginine, aspartic acid, serine, glutamic acid, proline, glycine, alanine, tyrosine and cysteine. A concentration of an essential amino acid may be at least about 1 g/100 g of protein concentrate, or at least about 1.5 g/100 g of protein concentrate, or at least about 2 g/100 g of protein concentrate, or at least about 2.5 g/100 g of protein concentrate, or at least about 3 g/100 g of protein concentrate, or at least about 4 g/100 g of dry at least about 2.5 g/100 g of protein concentrate, or at least about 3 g/100 g of protein concentrate, or at least about 4 g/100 g of protein concentrate, or at least about 5 g/100 g of protein concentrate, or at least about 6 g/100 g of protein concentrate, or at least about 7 g/100 g of protein concentrate, or at least about 8 g/100 g of protein concentrate, or at least about 9 g/100 g of protein concentrate, or at least about 10 g/100 g of protein concentrate in some embodiments.

A concentration of an amino acid (e.g., an essential amino acid), in some embodiments, may be expressed as a weight fraction of a protein recovered from a protein concentrate, and is at least about 1 g/100 g of protein, or at least about 1.5 g/100 g of protein, or at least about 2 g/100 g of protein, or at least about 2.5 g/100 g of protein, or at least about 3 g/100 g of protein, or at least about 4 g/100 g of protein, or at least about 5 g/100 g of protein, or at least about 6 g/100 g of protein, or at least about 7 g/100 g of protein, or at least about 8 g/100 g of protein, or at least about 9 g/100 g of protein, or at least about 10 g/100 g of protein.

In some embodiments, a protein concentrate may comprise one or more branched-chain amino acids (BCAAs). For example, a protein concentrate may include one or more amino acids selected from leucine, isoleucine, valine, and combinations thereof. A concentration of a BCAA may be at least about 1 g/100 g of protein concentrate, or at least about 1.5 g/100 g of protein concentrate, or at least about 2 g/100 g of protein concentrate, or at least about 2.5 g/100 g of protein concentrate, or at least about 3 g/100 g of protein concentrate, or at least about 4 g/100 g of dry at least about 2.5 g/100 g of protein concentrate, or at least about 3 g/100 g of protein concentrate, or at least about 4 g/100 g of protein concentrate, or at least about 5 g/100 g of protein concentrate, or at least about 6 g/100 g of protein concentrate, or at least about 7 g/100 g of protein concentrate, or at least about 8 g/100 g of protein concentrate, or at least about 9 g/100 g of protein concentrate, at least about 10 g/100 g of protein concentrate, at least about 11 g/100 g of protein concentrate, at least about 12 g/100 g of protein concentrate, at least about 13 g/100 g of protein concentrate, at least about 14 g/100 g of protein concentrate, or at least about 15 g/100 g of protein concentrate in some embodiments. In some embodiments, a BCAA protein content of a protein concentrate is higher than about 10%, or higher than about 11%, higher than about 12%, higher than about 13%, higher than about 14%, higher than about 15%, or higher than about 20%, or higher than about 25%, or higher than about 30%, or higher than about 35%, or higher than about 40%, or higher than about 45%, or higher than about 50%, or higher than about 55%, or higher than about 60% of total amino acids of a protein concentrate. In some embodiments, it has been found that the typical BCAA content of the subject protein rich products is 20-21% of total amino acids about 11% higher than the BCAA content of alternative protein products derived from pea and soy beans which contain about 18-19% (e.g., an increase from 18% to 20% is an 11% increase). The test method is ion exchange chromatography of amino acid profile based on AOAC Official Method 994.12.

In some embodiments, a protein concentrate may have a fat content lower than about 50%, or lower than about 40%, or lower than about 30%, or lower than about 25%, or lower than about 20%, or lower than about 15%, or lower than about 10%, or lower than about 5%, or lower than about 4%, or lower than about 3%, or lower than about 2%, or lower than about 1% by weight of the protein concentrate. A protein concentrate may have a fat content from about 1% to about 10%, or from about 10% to about 20%, or from about 20% to about 30%, or from about 30% to about 40%, or from about 40% to about 50% by weight of the protein concentrate in some embodiments. A protein concentrate, in some embodiments, may have a fat content from about 1% to about 50%, or from about 2% to about 40%, or from about 5% to about 30%, or from about 8% to about 20%, or from about 10% to about 15% by weight of the protein concentrate. A protein concentrate may be further processed to meet a desired fat content (e.g., higher or lower concentration, a desired fat composition).

According to some embodiments, a protein concentrate may include an ash content consisting of a residue containing inorganic mineral elements. An ash content in some embodiments may be determined by combusting a protein concentrate at a high temperature (e.g., ≥500° C.) to remove organic matter. A protein concentrate may have an ash content lower than about 50%, or lower than about 40%, or lower than about 30%, or lower than about 25%, or lower than about 20%, or lower than about 15%, or lower than about 10%, or lower than about 5%, or lower than about 4%, or lower than about 3%, or lower than about 2%, or lower than about 1% by weight of the protein concentrate in some embodiments. In some embodiments, a protein concentrate may have an ash content from about 1% to about 10%, or from about 10% to about 20%, or from about 20% to about 30%, or from about 30% to about 40%, or from about 40% to about 50% by weight of the protein concentrate. A protein concentrate, in some embodiments, may have an ash content from about 1% to about 50%, or from about 2% to about 40%, or from about 3% to about 30%, or from about 3% to about 20%, or from about 3% to about 15%, or from about 3% to about 10%, or from about 5% to about 10%, or from about 5% to about 15% by weight of the protein concentrate. A protein concentrate may be further processed to meet a desired ash content (e.g., higher or lower concentration, a desired ash composition).

According to some embodiments, a protein concentrate may have a carbohydrate content lower than about 50%, or lower than about 40%, or lower than about 30%, or lower than about 25%, or lower than about 20%, or lower than about 15%, or lower than about 10%, or lower than about 5%, or lower than about 4%, or lower than about 3%, or lower than about 2%, or lower than about 1% by weight of the protein concentrate. A protein concentrate, in some embodiments, may have a carbohydrate content from about 1% to about 10%, or from about 10% to about 20%, or from about 20% to about 30%, or from about 30% to about 40%, or from about 40% to about 50% by weight of the protein concentrate. In some embodiments, a protein concentrate may have a carbohydrate content from about 1% to about 50%, or from about 2% to about 40%, or from about 5% to about 30%, or from about 8% to about 20%, or from about 10% to about 15% by weight of the protein concentrate. A protein concentrate may be further processed to meet a desired carbohydrate content (e.g., higher or lower concentration, a desired carbohydrate composition).

In some embodiments, a protein concentrate may have a fiber content lower than about 20%, or lower than about 15%, or lower than about 10%, or lower than about 8%, or lower than about 5%, or lower than about 4%, or lower than about 3%, or lower than about 2%, or lower than about 1% by weight of the protein concentrate. A protein concentrate may be further processed to meet a desired fiber content (e.g., higher or lower concentration, a desired fiber composition).

For example, a dry protein concentrate produced by the processes described herein may include the contents summarized in Table 2.

TABLE 2

Example Contents of Dry Protein Concentrate Product

| Wt. Percent | Product 1 | Product 2 | Product 3 |
| --- | --- | --- | --- |
| Solids | ≥~90 | ≥~88-~90 | ≥~95 |
| Moisture | ≤~10 | ≤~12-~10 | ≤~5 |
| Protein | ≥~50 | from ~60 to ~80 | ≥~65-~75 |
| Fat | ≤~20 | from ~5 to ~20 | ≤~5-~15 |
| Ash | ≤~15 | from ~1 to ~10 | ≤~2-~10 |
| Carbohydrate | ≤~20 | from ~5 to ~20 | ≤~10-~15 |
| Fiber | ≤~10 | ≤~5 | ≤~5 |
| Other | ~10 | ~5-~20 | ~10-~15 |

A product and/or process, in some embodiments, may be configured or performed so other characteristics of a protein concentrate, (e.g., particle size, bacterial specification) meet desired criteria and/or may be suitable for an intended purpose.

According to some embodiments a protein concentrate may have a mesh size (e.g., most or all gross particles of the protein concentrate will pass through a mesh having an average pore size) of about 30 µm, or about 40 µm, or about 50 µm, or about 60 µm, or about 70 µm, or about 80 µm, or about 90 µm, or about 100 µm, or about 110 µm, or about 120 µm, or about 130 µm, or about 140 µm, or about 150 µm, or about 160 µm, or about 170 µm, or about 180 µm, or about 190 µm, or about 200 µm, or about 225 µm, or about 250 µm, or about 275 µm, or about 300 µm, or about 325 µm, or about 350 µm, or about 375 µm, or about 400 µm, or about 425 µm, or about 450 µm, or about 475 µm, or about 500 µm. A protein concentrate may have mesh size range of, in some embodiments, about 30 µm to about 500 µm, or about 30 µm to about 300 µm, or about 50 µm to about 300 µm, or about 70 µm to about 300 µm, or about 100 µm to about 300 µm, or about 30 µm to about 200 µm, or about 50 µm to about 200 µm, or about 70 µm to about 200 µm, or about 100 µm to about 200 µm, or about 30 µm to about 190 µm, or about 50 µm to about 190 µm, or about 70 µm or about 190 µm, or about 100 µm to about 190 µm, or about 30 µm to about 180 µm, or about 50 µm to about 180 µm, or about 70 µm to about 180 µm, or about 100 µm to about 180 µm, or about 30 µm to about 170 µm, or about 50 µm to about 170 µm, or about 70 µm to about 170 µm, or about 100 µm to about 170 µm.

A protein concentrate, according to some embodiments may have a density of about 400 kg/m³, or about 405 kg/m³, or about 410 kg/m³, or about 415 kg/m³, or about 420 kg/m³, or about 425 kg/m³, or about 430 kg/m³, or about 435 kg/m³, or about 440 kg/m³, or about 445 kg/m³, or about 450 kg/m³.

In some embodiments a protein concentrate may have a solubility value (% water soluble nitrogen) of at least 35%, or at least 40%, or at least 45%, or at least 50%, or at least 55%, or at least 60%, or at least 65%, or at least 70%, or at least 75%. A solubility value may be determined using the Nitrogen Solubility Index (NSI) method as described in F. Vojdani, *Methods of Testing Protein Functionality* 11-60 (G. M. Hall, ed., 1996).

According to some embodiments, a protein concentrate may have a dispersibility value (% water dispersible protein/% total protein) of at least 35%, or at least 40%, or at least 45%, or at least 50%, or at least 55%, or at least 60%, or at least 65%, or at least 70%, or at least 75%. A dispersibility value may be determined using the Protein Dispersibility Index (PDI) as described in F. Vojdani, *Methods of Testing Protein Functionality* 11-60 (G. M. Hall, ed., 1996).

In some embodiments, a standard plate count of bacteria may be lower than about 100,000 cfu/g, or lower than about 80,000 cfu/g, or lower than about 60,000 cfu/g, or lower than about 50,000 cfu/g, or lower than about 40,000 cfu/g, or lower than about 30,000 cfu/g, or lower than about 25,000 cfu/g, or lower than about 20,000 cfu/g, or lower than about 15,000 cfu/g, or lower than about 10,000 cfu/g, or lower than about 5,000 cfu/g, or lower than about 1000 cfu/g, or lower than about 500 cfu/g. If a protein concentrate comprises any *Escherichia coli*, the bacteria may be present at such low levels as to be undetectable and/or noninfectious. If a protein concentrate comprises any *Salmonella* spp., the bacteria may be present at such low levels as to be undetectable and/or noninfectious. If a protein concentrate comprises any yeast/mold, the microorganism count may be lower than about 500/g, or lower than about 400/g, or lower than about 300/g, or lower than about 250/g, or lower than about 200/g, or lower than about 150/g, or lower than about 100/g, or lower than about 50/g.

In some embodiments, a protein concentrate may be packed and/or sealed in either an industry standard bag or drum of varying sizes. A sealing method of industry-standard grade may be used to ensure proper shelf-life and shipping conditions. A bag or drum may include printed instructions or specifications regarding, for example, its intended use, shelf-life, suggested storage conditions, shipping conditions, compositions, or the like, or a combination thereof. An antioxidant (e.g., rosemary extract) may be mixed with a protein concentrate before packaging, according to some embodiments.

Processing a First Solid and/or Solid Mixture

A first solid (e.g., first portion, second portion) and/or solid mixture (e.g., first portion, second portion) may be processed to generate one or more carbohydrate-rich products. As described previously, a solid mixture may include one or more of a first solid (e.g., FIG. 2, 231), a first cake (e.g., 242), a second cake (e.g., FIG. 2, 247), or any combination thereof that remain after one or more separation processes (e.g., FIG. 2, 230/240/245). Carbohydrate rich products may include a dry biocrude product suitable as a fuel feedstock or a carbohydrate-rich meal suitable as a human or animal feed supplement (e.g., *Lemna* meal).

A first solid and/or solid mixture may be processed (e.g., drying, pelletization), in some embodiments, to generate at least one of a dry biocrude and a carbohydrate-rich meal. According to some embodiments, processing a first solid and/or solid mixture involves drying and/or pelletization.

A process for generating a carbohydrate-rich product (e.g., dry biocrude and/or carbohydrate-rich) meal may be varied depending upon the specific characteristics desired, including, for example, moisture content, particle size, protein content, fat content, fiber content, ash content, shelf-life, pellet size, texture, or any combination thereof.

In some embodiments, a first solid and/or a solid mixture may be dried to reduce a moisture content of a resulting carbohydrate-rich product (e.g., dry biocrude and/or carbohydrate-rich meal). A drying procedure, in some embodiments, may be performed in conjunction with (e.g., prior to, following) other processing of a first solid and/or a solid mixture, such that an end product is a carbohydrate-rich product with a reduced moisture content. A drying procedure may be performed, in some embodiments, using a dryer mechanism including, for example, a spray dryer, double drum dryer, flash dryer, evaporator, or any combination thereof.

In some embodiments, an inlet temperature of a dryer mechanism (e.g., a temperature at an entrance to a dryer)

may be above or above 25° C., or above 50° C., or above 75° C., or above 100° C., or above 125° C., or above 150° C., or above 175° C., or above 200° C., or above 225° C., or above 250° C., or above 275° C., or above 300° C., or above 325° C., or above 350° C., or above 375° C., or above 400° C., or above 425° C., or above 450° C., or above 475° C., or above 500° C. An inlet temperature may be from about 25° C. to about 50° C., or from about 50° C. to about 75° C., or from about 75° C. to about 100° C., or from about 100° C. to about 125° C., or from about 125° C. to about 150° C., or from about 150° C. to about 175° C., or from about 175° C. to about 200° C., or from about 200° C. to about 225° C., or from about 225° C. to about 250° C., or from about 250° C. to about 275° C., or from about 275° C. to about 300° C., or from about 300° C. to about 325° C., or from about 325° C. to about 350° C., or from about 350° C. to about 375° C., or from about 375° C. to about 400° C., or from about 400° C. to about 425° C., or from about 425° C. to about 450° C., or from about 450° C. to about 475° C., or from about 475° C. to about 500° C., or above 500° C., in some embodiments. An inlet temperature, according to some embodiments, may be from about 50° C. to about 100° C., or from about 100° C. to about 150° C., or from about 150° C. to about 200° C., or from about 200° C. to about 250° C., or from about 250° C. to about 300° C., or from about 300° C. to about 350° C., or from about 350° C. to about 400° C., or from about 400° C. to about 450° C., or from about 450° C. to about 500° C., or above 500° C.

According to some embodiments, an outlet temperature of a dryer mechanism (e.g., a temperature at an exit from a dryer) may be below about 300° C., or below about 275° C., or below about 250° C., or below about 225° C., or below about 200° C., or below about 175° C., or below about 150° C., or below about 125° C., or below about 100° C., or below about 75° C., or below about 50° C., or below about 25° C. An outlet temperature, in some embodiments, may be from about 300° C. to about 275° C., or from about 275° C. to about 250° C., or from about 250° C. to about 225° C., or from about 225° C. to about 200° C., or from about 200° C. to about 175° C., or from about 175° C. to about 150° C., or from about 150° C. to about 125° C., or from about 125° C. to about 100° C., or from about 100° C. to about 75° C., or from about 75° C. to about 50° C., or from about 50° C. to about 25° C., or below about 25° C. In some embodiments, an outlet temperature may be from about 300° C. to about 250° C., or from about 250° C. to about 200° C., or from about 200° C. to about 150° C., or from about 150° C. to about 100° C., from about 100° C. to about 50° C., or from about 50° C. to about 25° C., or below about 25° C.

A volume of a first solid and/or a solid mixture may be mixed with a volume of a carbohydrate-rich product (e.g., dry biocrude and/or carbohydrate-rich meal) prior to drying, in some embodiments. This process, known as back-mixing, may be employed when, for example, a moisture content of a first solid and/or a solid mixture exceeds a level that a dryer mechanism is capable of accepting. By back-mixing a carbohydrate-rich product with a first solid and/or a solid mixture, a total moisture content may be kept within specifications of a dryer mechanism, thereby reducing operational costs (e.g., wear and tear on equipment).

A moisture content of a carbohydrate-rich product (e.g., dry biocrude and/or carbohydrate-rich meal) may be below about 90%, or below about 80%, or below about 70%, or below about 60%, or below about 50%, or below about 40%, or below about 30%, or below about 20%, or below about 10%, or below about 5%, or below about 1% by weight of a product, in some embodiments.

According to some embodiments a first solid and/or a solid mixture may be pelletized (e.g., steam pelletization). Pelletization may be performed before or after a drying procedure, in some embodiments.

Lutein Rich Products

According to some embodiments, the present disclosure relates to processes for a production of lutein rich products from a harvested microcrop (e.g., a photosynthetic aquatic species, an aquatic plant species, Lemna, algal species) according to specific example embodiments of the disclosure. Lutein rich products may include a dry biocrude product (e.g., suitable as a fuel feedstock), or a soluble protein concentrate (e.g., suitable as a human or an animal feed supplement), or a dry protein concentrate (e.g., suitable as a human or an animal feed supplement). A dry biocrude may be used as fuel feedstock (e.g., power plant, refinery, coker) for combustion, co-combustion with other hydrocarbon-based fuels (e.g., coal), and feedstock for biofuel conversion and/or fermentation. Whereas a soluble protein product, a dry protein concentrate, or any combination thereof may be suitable may be used as a feed or feed supplement for animal (e.g., fish, swine, cattle) or human consumption. A lutein rich product may also be used in an animal bedding and/or litter.

In some embodiments, the present disclosure relates to processes, methods, and systems for a production of lutein rich products, a soluble protein, or a dry protein concentrate.

A soluble protein product or a dry protein concentrate, according to some embodiments, may comprise a lutein concentration of at least 100 mg/kg or at least 150 mg/kg, or at least 200 mg/kg, or at least 250 mg/kg, or at least 300 mg/kg, or at least 350 mg/kg, or at least 400 mg/kg, or at least 450 mg/kg, or at least 500 mg/kg, or at least 550 mg/kg, or at least 600 mg/kg, or at least 650 mg/kg, or at least 700 mg/kg, or at least 750 mg/kg. In some embodiments, a soluble protein product or a dry protein concentrate may comprise a lutein concentration of at least about 500 mg/kg, or at least about at least about 550 mg/kg, or at least about 560 mg/kg, or at least about 570 mg/kg, or at least about 580 mg/kg, at least about 585 mg/kg, at least about 590 mg/kg, at least about 595 mg/kg, at least about 600 mg/kg, at least about 605 mg/kg, at least about 610 mg/kg, at least about 615 mg/kg, at least about 620 mg/kg, at least about 625 mg/kg, and at least about 630 mg/kg, or at least about 640 mg/kg, or at least about 650 mg/kg, or at least about 660 mg, or at least about 670 mg/kg, or at least about 680 mg/kg, or at least about 690 mg/kg, or at least about 700 mg/kg.

Carbohydrate Rich Products

The present disclosure, in some embodiments, relates to processes for production of carbohydrate rich products (e.g., dry biocrude, carbohydrate-rich meal) from a harvested microcrop (e.g., aquatic plant species, Lemna, algal species) according to specific example embodiments of the disclosure. Carbohydrate rich products may include a dry biocrude product suitable as a fuel feedstock or a carbohydrate-rich meal suitable as an animal feed supplement. A dry biocrude has many potential uses including: fuel feedstock (e.g., power plant, refinery, coker) for combustion; co-combustion with other hydrocarbon-based fuels (e.g., coal); and feedstock for biofuel conversion and/or fermentation. A carbohydrate meal (e.g., Lemna meal) may be used as a feed or feed supplement for animal (e.g., fish, swine, cattle) or human consumption.

A carbohydrate-rich product (e.g., dry biocrude and/or carbohydrate-rich meal) may have a protein content lower than about 50 wt. %, or lower than about 40 wt. %, or lower than about 30 wt. %, or lower than about 25 wt. %, or lower than about 20 wt. %, or lower than about 15 wt. %, or lower than about 14 wt. %, or lower than about 13 wt. %, or lower than about 12 wt. %, or lower than about 11 wt. %, or lower than about 10 wt. %, or lower than about 5 wt. % by weight of a product. In some embodiments, a carbohydrate-rich product (e.g., dry biocrude and/or carbohydrate-rich meal) may have a protein content from about 1 wt. % to about 10 wt. %, or from about 10 wt. % to about 20 wt. %, or from about 20 wt. % to about 30 wt. %, or from about 30 wt. % to about 40 wt. %, or from about 40 wt. % to about 50 wt. % by weight of a product. In some embodiments, a carbohydrate-rich product (e.g., dry biocrude and/or carbohydrate-rich meal) may have a protein content from about 1 wt. % to about 50 wt. %, or from about 5 wt. % to about 40 wt. %, or from about 5 wt. % to about 30 wt. %, or from about 5 wt. % to about 20 wt. %, or from about 5 wt. % to about 15 wt. %, or from about 5 wt. % to about 10 wt. %, or from about 10 wt. % to about 50 wt. %, or from about 10 wt. % to about 40 wt. %, or from about 10 wt. % to about 30 wt. %, or from about 10 wt. % to about 20 wt. %, or from about 10 wt. % to about 15 wt. % by weight of a product. A carbohydrate-rich product may be further processed to meet a desired protein content (e.g., higher or lower concentration, a desired amino acid composition).

In some embodiments a carbohydrate-rich product (e.g., dry biocrude and/or carbohydrate-rich meal) may have a fiber content lower than about 70%, or lower than about 60%, or lower than about 50 wt. %, or lower than about 40 wt. %, or lower than about 30 wt. %, or lower than about 20 wt. %, or lower than about 15 wt. %, or lower than about 10 wt. % by weight of a product. A carbohydrate-rich product, in some embodiments, may have a fiber content from about 1 wt. % to about 10 wt. %, or from about 10 wt. % to about 20 wt. %, or from about 15 wt. % to about 25 wt. %, or from about 20 wt. % to about 30 wt. %, or from about 25 wt. % to about 35 wt. %, or from about 30 wt. % to about 40 wt. %, or from about 35 wt. % to about 45 wt. %, or from about 40 wt. % to about 50 wt. %, or from about 45 wt. % to about 55 wt. %, or from about 50 wt. % to about 60 wt. %, or from about 55 wt. % to about 65 wt. % by weight of a product. A carbohydrate-rich product (e.g., dry biocrude and/or carbohydrate-rich meal) may have a fiber content from about 5 wt. % to about 65 wt. %, or from about 5 wt. % to about 60 wt. %, or from about 5 wt. % to about 55 wt. %, or from about 5 wt. % to about 50 wt. %, or from about 5 wt. % to about 40 wt. %, or from about 10 wt. % to about 65 wt. %, or from about 10 wt. % to about 55 wt. %, or from about 10 wt. % to about 50 wt. %, or from about 10 wt. % to about 45 wt. %, or from about 10 wt. % to about 40 wt. %, or from about 20 wt. % to about 65 wt. %, or from about 20 wt. % to about 60 wt. %, or from about 20 wt. % to about 55 wt. %, or from about 20 wt. % to about 50 wt. %, or from about 20 wt. % to about 45 wt. %, or from about 20 wt. % to about 40 wt. %, or from about 30 wt. % to about 65 wt. %, or from about 30 wt. % to about 60 wt. %, or from about 30 wt. % to about 55 wt. %, or from about 30 wt. % to about 50 wt. %, or from about 30 wt. % to about 45 wt. %, or from about 30 wt. % to about 40 wt. %, or from about 40 wt. % to about 65 wt. %, or from about 40 wt. % to about 60 wt. %, or from about 40 wt. % to about 55 wt. %, or from about 40 wt. % to about 50 wt. %, or from about 40 wt. % to about 45 wt. % by weight of a product, according to some embodiments. According to some embodiments, a carbohydrate-rich product may be further processed to meet a desired fiber content (e.g., higher or lower concentration, a desired fiber composition).

A carbohydrate-rich product (e.g., dry biocrude and/or carbohydrate-rich meal) may have, in some embodiments, an ash content lower than 50 wt. %, or lower than about 40 wt. %, or lower than about 30 wt. %, or lower than about 25 wt. %, or lower than about 20 wt. %, or lower than about 15 wt. %, or lower than about 10 wt. %, or lower than about 5 wt. % by weight of a product. In some embodiments, a carbohydrate-rich product (e.g., dry biocrude and/or carbohydrate-rich meal) may have an ash content from about 1 wt. % to about 10 wt. %, or from about 10 wt. % to about 20 wt. %, or from about 20 wt. % to about 30 wt. %, or from about 30 wt. % to about 40 wt. %, or from about 40 wt. % to about 50 wt. % by weight of a product. A carbohydrate-rich product (e.g., dry biocrude and/or carbohydrate-rich meal) may have an ash content from about 1 wt. % to about 50 wt. %, or from about 2 wt. % to about 40 wt. %, or from about 3 wt. % to about 30 wt. %, or from about 3 wt. % to about 20 wt. %, or from about 3 wt. % to about 15 wt. %, or from about 3 wt. % to about 10 wt. %, or from about 5 wt. % to about 10 wt. %, or from about 5 wt. % to about 15 wt. %, or from about 5 wt. % to about 20 wt. % by weight of a product, according to some embodiments. A carbohydrate-rich product may be further processed to meet a desired ash content (e.g., higher or lower concentration, a desired ash composition).

In some embodiments, a carbohydrate-rich product (e.g., dry biocrude and/or carbohydrate-rich meal) may have a fat content lower than about 50 wt. %, or lower than about 40 wt. %, or lower than about 30 wt. %, or lower than about 25 wt. %, or lower than about 20 wt. %, or lower than about 15 wt. %, or lower than about 10 wt. %, or lower than about 5 wt. % by weight of a product. A carbohydrate-rich product (e.g., dry biocrude and/or carbohydrate-rich meal) may have a fat content from about 1 wt. % to about 10 wt. %, or from about 5 wt. % to about 10 wt. %, or from about 10 wt. % to about 20 wt. %, or from about 20 wt. % to about 30 wt. %, or from about 30 wt. % to about 40 wt. %, or from about 40 wt. % to about 50 wt. % by weight of a product. According to some embodiments, a carbohydrate-rich product (e.g., dry biocrude and/or carbohydrate-rich meal) may have a fat content from about 1 wt. % to about 50 wt. %, or from about 1 wt. % to about 40 wt. %, or from about 1 wt. % to about 30 wt. %, or from about 1 wt. % to about 20 wt. %, or from about 1 wt. % to about 15 wt. %, or from about 1 wt. % to about 10 wt. %, or from about 1 wt. % to about 5 wt. %, or from about 2 wt. % to about 40 wt. %, or from about 2 wt. % to about 30 wt. %, or from about 2 wt. % to about 20 wt. %, or from about 2 wt. % to about 15 wt. %, or from about 2 wt. % to about 10 wt. %, or from about 2 wt. % to about 5 wt. %, or from about 3 wt. % to about 30 wt. %, or from about 3 wt. % to about 20 wt. %, or from about 3 wt. % to about 15 wt. %, or from about 3 wt. % to about 10 wt. %, or from about 3 wt. % to about 5 wt. %, or from about 5 wt. % to about 10 wt. %, or from about 5 wt. % to about 15 wt. %, or from about 5 wt. % to about 20 wt. % by weight of a product. A carbohydrate-rich product may be further processed to meet a desired fat content (e.g., higher or lower concentration, a desired fat composition).

A carbohydrate-rich product (e.g., dry biocrude and/or carbohydrate-rich meal) may have, according to some embodiments, a carbohydrate content higher than about 30 wt. %, or higher than about 40 wt. %, or higher than about 50 wt. %, or higher than about 60 wt. %, or higher than about 65 wt. %, or higher than about 70 wt. %, or higher than about 75 wt. %, or higher than about 80 wt. %, or higher than about 85 wt. % by weight of a dry bio-crude. In some embodiments, a carbohydrate-rich product (e.g., dry biocrude and/ or carbohydrate-rich meal) may have a carbohydrate content from about 30 wt. % to about 90 wt. %, or from about 40 wt. % to about 90 wt. %, or from about 50 wt. % to about 90 wt. %, or from about 60 wt. % to about 90 wt. %, or from about 70 wt. % to about 90 wt. %, or from about 80 wt. % to about 90 wt. %, or from about 30 wt. % to about 85 wt. %, or from about 40 wt. % to about 85 wt. %, or from about 50 wt. % to about 85 wt. %, or from about 60 wt. % to about 85 wt. %, or from about 70 wt. % to about 85 wt. %, or from about 30 wt. % to about 80 wt. %, or from about 40 wt. % to about 80 wt. %, or from about 50 wt. % to about 80 wt. %, or from about 60 wt. % to about 80 wt. %, or from about 70 wt. % to about 80 wt. % by weight of a product. A carbohydrate-rich product may be further processed to meet a desired carbohydrate content (e.g., higher or lower concentration, a desired carbohydrate composition).

According to some embodiments, a carbohydrate-rich product (e.g., dry biocrude and/or carbohydrate-rich meal) may have a negligible amount of volatile matter. A carbohydrate-rich product may have a volatile matter content lower than about 1 wt. %, or lower than about 2 wt. %, or lower than about 5 wt. %, or lower than about 10 wt. %, or lower than about 15 wt. %, or lower than about 20 wt. % by weight of a product, in some embodiments. A carbohydrate-rich product may have, in some embodiments, a volatile matter content from about 1 wt. % to about 5 wt. %, or from about 1 wt. % to about 10 wt. %, or from about 1 wt. % to about 15 wt. %, or from about 1 wt. % to about 20 wt. %, from about 2 wt. % to about 10 wt. %, or from about 2 wt. % to about 15 wt. %, or from about 2 wt. % to about 20 wt. %, from about 5 wt. % to about 10 wt. %, or from about 5 wt. % to about 15 wt. %, or from about 5 wt. % to about 20 wt. % by weight of a product.

A carbohydrate-rich product (e.g., dry biocrude and/or carbohydrate-rich meal) may have, in some embodiments, an energy content higher than about 3 MJ/kg, or higher than about 5 MJ/kg, or higher than about 8 MJ/kg, or higher than about 10 MJ/kg, or higher than about 12 MJ/kg, or higher than about 15 MJ/kg, or higher than about 50 MJ/kg, or higher than about 20 MJ/kg. A dry bio-crude may be further processed to meet a desired energy content (e.g., a higher or lower energy content, a desired energy content).

For example, a carbohydrate-rich product (e.g., dry biocrude and/or carbohydrate-rich meal) produced by a process described herein may include the contents summarized in Table 3.

TABLE 3

Example Contents of Dry Biocrude and/or Carbohydrate-Rich Meal

|  | Product A | Product B | Product C |
|---|---|---|---|
| Wt. % Solids | ≥~90 | ≥~88 to ~92 | ≥~90 |
| % Moisture | ≤~10 | ≤~8-~12 | ≤~10 |
| % Protein | ≤~20 | from ~10 to ~20 | ≤~14 |
| % Fat | from ~5 to ~10 | from ~5 to ~20 | ≤~5 |
| % Ash | ≤~15 | from ~1 to ~20 | ≤~12 |
| % Carbohydrate | ≥~50 | from ~60 to ~90 | ≥~65 to ~70 |
| % Fiber | ≥~50 | ≥~40 | ≥~40 to ~60 |
| Energy (MJ/kg) | ≥~10 | ≥~10 | ≥~10 |

Component Ratios

According to some embodiments, the present disclosure relates to compositions comprising soluble microcrop protein. For example, a composition comprising soluble microcrop proteins, may comprise two or more of the following components: protein, lutein, fats, carbohydrates, polyphenols, and fiber, wherein each component may be present at a concentration disclosed herein, examples of which are provided in Table 4 and Table 5. A soluble microcrop protein composition, for example, may include two or more such components at a desirable ratio to each other. A desirable ratio may be selected from any disclosed concentration. Using Table 4 to illustrate, a ratio of protein to fat may be about 30:0.2 or about 30:2 or about 30:20, about 60:0.2 or about 60:2 or about 60:20, or about 90:0.2 or about 90:2 or about 90:20. A ratio of any other component to protein may be derived from Table 4 in the same manner. Using Table 5 to illustrate, a ratio of carbohydrate to fat may be about 1:0.2, or about 1:2, or about 1:20, about 10:0.2, or about 10:2, or about 10:20, about 50:0.2, or about 50:2, or about 50:20. A ratio of any other component to protein may be derived from Table 5 in the same manner.

According to some embodiments, in a composition comprising a soluble microcrop protein, a ratio of such protein to such polyphenol may be greater than the ratio of such protein to such polyphenol in the living, intact microcrop (e.g., *Lemna*), from which such soluble microcrop protein is derived. For example, the protein to polyphenol ratio may be about 50:1, about 25:1, about 10:1, about 5:1, about 4:1, about 3:1, about 2:1, and about 1.5:1.

TABLE 4

Examples of Concentrations

| Protein | 0.2, 2, 20 | Fats |
| 30, 60, 90 | 0.01, 0.05, 0.1 | Lutein |
|  | 1, 10, 50 | Carbohydrates |
|  | 1, 20, 70 | Fiber |
|  | 0.05, 0.5, 2 | Polyphenols |

TABLE 5

Examples of Concentrations

| Carbohydrates | 0.2, 2, 20 | Fats |
| 1, 10, 50 | 0.01, | Lutein |
|  | 0.05, 0.1 |  |
|  | 30, 60, 90 | Proteins |
|  | 1, 20, 70 | Fiber |
|  | 0.05, 0.5, 2 | Polyphenols |

Heat Exchange

According to some embodiments, thermal energy exchange mechanisms (e.g., heat exchanger) may decrease an overall energy input required for a production of concentrated proteins and/or carbohydrate-rich products from a microcrop (e.g., *Lemna*). In some embodiments, a chilled stream (e.g., recipient stream) may be directed to flow in proximity to a donor stream having thermal energy such that the chilled stream may absorb at least some of a donor stream thermal energy. A recipient stream, according to some embodiments, may be directed to flow in proximity to a donor stream having thermal energy such that the recipient stream absorbs at least some of the donor stream thermal energy.

In some embodiments, a recipient stream may be at least one of a lysed biomass (e.g., first portion, second portion), a juice fraction (e.g., first portion, second portion), a first juice (e.g., first portion, second portion), a first soluble protein fraction (e.g., first portion, second portion), a first reject stream, a second soluble protein fraction (e.g., first portion, second portion), a second reject stream, and a permeate. A recipient stream may be a chilled stream, in some embodiments. According to some embodiments at least one of a lysed biomass (e.g., first portion, second portion), a juice fraction (e.g., first portion, second portion), a first juice (e.g., first portion, second portion), a first soluble protein fraction (e.g., first portion, second portion), a first reject stream, a second soluble protein fraction (e.g., first portion, second portion), a second reject stream, and a permeate may be chilled to form a chilled stream. A recipient stream (e.g., a chilled stream) may have a temperature below room temperature (e.g., about 12° C.) at a time of use. In some embodiments, a recipient stream (e.g., a chilled stream) may have a temperature below about 30° C., or below about 20° C., or below about 15° C., or below about 10° C., or below about 5° C., or below about 2° C., or below about 1° C., or below about 0° C. at a time of use. A recipient stream (e.g., a chilled stream) may have a temperature between about 0° C. and about 10° C., or between about 5° C. and about 15° C., or between about 10° C. and about 20° C., or 15° C. and about 25° C., or between about 20° C. and about 30° C. at a time of use, in some embodiments. In some embodiments, a recipient stream (e.g., a chilled stream) may have a temperature of about 12° C. According to some embodiments, a recipient stream (e.g., a chilled stream) may have a temperature that is lower than a donor stream.

A donor stream, in some embodiments, may comprise at least one of a lysed biomass (e.g., first portion, second portion), a juice fraction (e.g., first portion, second portion), or a first juice (e.g., first portion, second portion). According to some embodiments, a donor stream may have a temperature that is higher than a recipient stream. In some embodiments, a donor stream may have a temperature above room temperature (e.g., about 50° C.). In some embodiments, a donor stream may have a temperature above about 20° C., or above about 25° C., or above about 30° C., or above about 35° C., or above about 40° C., or above about 45° C., or above about 50° C., or above about 55° C., or above about 60° C., or above about 65° C., or above about 70° C., or above about 75° C., or above about 80° C., or above about 85° C., or above about 90° C., or above about 95° C., or above about 100° C. at a time of use. A donor stream may have a temperature between about 40° C. and about 50° C., or between about 45° C. and about 55° C., or between about 50° C. and about 60° C. at a time of use, in some embodiments. According to some embodiments, a donor stream may have a temperature between about 75° C. and about 80° C., or between about 80° C. and about 85° C., or between about 85° C. and about 90° C., or between about 90° C. and about 95° C., or between about 95° C. and about 100° C. In some embodiments, a donor stream may have a temperature between about 50° C. and about 80° C., or between about 55° C. and about 85° C., or between about 60° C. and about 90° C., or between about 65° C. and about 95° C., or between about 70° C. and about 100° C.

In some embodiments, a thermal energy may be generated by one or more processes during a production of concentrated proteins and/or carbohydrate-rich products from a microcrop (e.g., *Lemna*). For example, a thermal energy may be generated by (1) drying a concentrated protein, (2) drying a carbohydrate-rich product (e.g., dry biocrude and/or carbohydrate-rich meal), and/or (3) chilling at least one of a lysed biomass (e.g., first portion, second portion), a juice fraction (e.g., first portion, second portion), a first juice (e.g., first portion, second portion), a first soluble protein fraction (e.g., first portion, second portion), a first reject stream, a second soluble protein fraction (e.g., first portion, second portion), a second reject stream, and a permeate to generate a chilled stream. According to some embodiments, a thermal energy may be generated in thermal communication with a heat exchanger. For example, chilling at least one of a juice fraction (e.g., first portion, second portion), a first juice (e.g., first portion, second portion), a first soluble protein fraction (e.g., first portion, second portion), a second soluble protein fraction (e.g., first portion, second portion) may be performed in thermal communication with a heat exchanger. Heating at least one of a wash solution, a first reject stream, a second reject stream, and a permeate may be performed in thermal communication with a heat exchanger, in some embodiments. In some embodiments, drying a concentrated protein and/or drying a carbohydrate-rich product may be performed in thermal communication with a heat exchanger.

FIG. 1

FIG. 1 is a schematic diagram illustrating a process 100 for growing, harvesting, and separating a microcrop (e.g., aquatic plant species, *Lemna, algal* species) for a production of protein concentrate and/or carbohydrate rich products according to a specific example embodiment of the disclosure. A microcrop (e.g., *Lemna*) may be cultivated in a bioreactor system 105, harvested 110, and separated 125 to form a juice fraction 126 and a solid fraction 127. In some embodiments, a juice fraction may be processed to produce one or more protein concentrate products and/or a solid fraction may be processed to produce one or more carbohydrate rich products. Protein concentrate products may include products suitable for animal feed and/or human consumption. Carbohydrate rich products may include a dry biocrude suitable as a fuel feedstock or a carbohydrate-rich meal suitable as a feed or supplement for animal and/or human consumption. A process 100 may be performed indoors, outdoors, and any combination thereof based, for example, on the specific environmental characteristics of the location(s).

As shown in FIG. 1, a microcrop may be cultivated in a bioreactor system 105 (e.g., open bioreactor, closed bioreactor). A bioreactor system may contain a growth medium (e.g., water, a nutrient composition). In some embodiments, a bioreactor system, in some embodiments, may be configured to collect rainfall and/or to intake water from a source of recycled or ground water (e.g., storm water, recycled water) or any other suitable source. A bioreactor system may be configured, in some embodiments, to insert additional nutrients (e.g., nitrogen, phosphorus, potassium) or gases (e.g., oxygen; carbon dioxide) at desired time indicators or in response to sensor readings. In some embodiments, a bioreactor system may comprise a monitoring system. A bioreactor system, in some embodiments, may monitor and adjust a thickness and distribution of a microcrop mat. For example, when a microcrop reaches a desired thickness or distribution a bioreactor system may initiate harvest procedures.

As shown in FIG. 1, at specified times (e.g., based on environmental conditions) or after a microcrop develops desired characteristics (e.g., mat thickness; mat distribution; maturation), a microcrop may be harvested 110 (e g, manual, automated) from a bioreactor system, forming a biomass 111. An automated skimmer system, in some embodiments, may collect a microcrop from a bioreactor system and transfer a harvested microcrop (e.g., via a pumping system) onto an inclined vibrating screen to separate a biomass from growth medium and debris. In some embodiments a microcrop may be harvested by vacuum skimming the microcrop from a bioreactor system through a stationary screen filter. A microcrop may be harvested manually, according to some embodiments. A biomass slurry, including a harvested microcrop (e.g., *Lemna*) and a growth medium (e.g., water), may be conveyed to an inclined screen, which may optionally vibrate, where a biomass (e.g., microcrop) may be separated from the growth medium.

During harvesting 110, a separated growth medium may be recycled 112 back into a bioreactor system or to an additional storage container (e.g., container or pond), according to some embodiments. In some embodiments, at least about 40% (v/v), or at least about 50% (v/v), or at least about 60% (v/v), or at least about 70% (v/v), or at least about 80% (v/v), or at least about 90% (v/v), or at least about 95% (v/v) of a growth medium (e.g., water) separated from a biomass may be recycled for future use.

As shown in FIG. 1, a biomass 111 may go through a wash procedure 115 (e.g., submerging, spraying, slurry) to remove debris, contaminants, microorganisms, and/or toxins. In some embodiments a wash procedure may be performed by exposing (e.g., submerging, spraying) at least about one surface of a biomass to a wash solution (e.g., water, growth medium, antimicrobial solution). A wash solution (e.g., water, ozonated water), in some embodiments, may be combined with a biomass to form a slurry. According to some embodiments, a wash solution may comprise by volume at least about 10%, at least about 20%, at least about 30%, at least about 40%, at least about 50%, at least about 60%, at least about 70%, at least about 80%, or at least about 90% recycled from another stage of process 100 (e.g., recycled wash solution 116, a reject stream from filtration stages (FIG. 2A, 252)). In some embodiments, a second wash solution (e.g., water, ozonated water, recycled wash solution 116) may be applied to a biomass. A third wash solution (e.g., water, ozonated water, recycled wash solution) may be applied to a biomass, in some embodiments. In some embodiments a first wash solution may be or may comprise a reject stream from a filtration process (e.g., FIG. 2A, 252), a second wash solution may be or may comprise water, and a third wash solution may be or may comprise ozonated water. Some or all of a wash solution (e.g., a first, second, and/or third wash solution), in some embodiments, may be separated from a biomass (e.g., using an inclined screen or vibratory screen).

In some embodiments, some or all of a wash solution, second wash solution, and/or third wash solution may be collected and reused/recycled 116/117. By volume, at least about 40%, or at least about 50%, or at least about 60%, or at least about 70%, or at least about 80%, or at least about 90%, or at least about 95% of a wash solution, second wash solution, and/or third wash solution (e.g., water) separated from a biomass may be recycled for future use (e.g., recycled wash solution 116, used as growth medium in a bioreactor system 117), according to some embodiments.

As shown in FIG. 1, a biomass, either washed or unwashed, may be lysed 120 (e.g., pressing, tearing, ultrasonic treatment). A lysing process may be achieved using, for example, a shear mill, a ball mill, colloid mill, knife mill, hammer mill, grinding mill, puree machine, filter press, or any combination thereof.

A lysed biomass 121 may be separated 125, as shown in FIG. 1, to form a juice fraction 126 and a solid fraction 127. Separating 125 a lysed biomass 121 or biomass may involve pressing (e.g., belt press), centrifugation (e.g., decanter centrifuge), filtration, pressurized filtration, or any combination thereof. Interchangeable unit operations for separating a lysed biomass and/or biomass include, for example, a decanter centrifuge, a belt press, a fan press, a rotary press, a screw press, a filter press, a finisher press, or any combination thereof. In some embodiments, a juice fraction 126 may undergo a processing step for the selective removal of at least one polyphenol (a).

FIGS. 2A and 2B

FIG. 2A and FIG. 2B illustrate separate embodiments for processing a microcrop (e.g. *Lemna*), for a production of protein concentrate and/or carbohydrate rich products. In some embodiments a microcrop may be harvested (e.g., FIG. 1, 110) forming a biomass (e.g., FIG. 1, 111).

Washing a Biomass

A biomass may be washed 215 prior to processing, according to some embodiments. A wash procedure may remove debris, contaminants, nutrients, microorganisms, and/or toxins. A wash solution, in some embodiments, may be combined with a biomass to form a slurry. According to some embodiments, a wash solution (e.g., a first, second, and/or third wash solution) may have a temperature below room temperature (e.g., about 12° C.). A wash solution, in some embodiments, may have a temperature above room temperature (e.g., 50° C.). In some embodiments, a wash solution may comprise any desired portion of recycled fluid. For example, a wash solution may comprise at least about 10% (v/v), at least about 20% (v/v), at least about 30% (v/v), at least about 40% (v/v), at least about 50% (v/v), at least about 60% (v/v), at least about 70% (v/v), at least about 80% (v/v), or at least about 90% (v/v) recycled from another stage of a process (e.g., recycled wash solution 216, a reject stream from filtration (e.g., FIG. 2A, 252)). In some embodiments, a second wash solution (e.g., water, ozonated water, recycled wash solution FIG. 1, 116) may be applied to a biomass.

A third wash solution (e.g., water, ozonated water, recycled wash solution) may be applied to a biomass, in some embodiments. In some embodiments a first wash solution may be a reject stream from a filtration process (e.g., FIG. 2A, 252), a second wash solution may be water, and a third wash solution may be ozonated water. Some or all of a wash solution (e.g., a first wash solution, second wash solution, and/or third wash solution) may be separated, in some embodiments, from a biomass (e.g., using an inclined screen or vibratory screen).

Some or all of a wash solution, second wash solution, and/or third wash solution may be collected and/or reused, according to some embodiments. At least about 40%, or at least about 50%, or at least about 60%, or at least about 70%, or at least about 80%, or at least about 90%, or at least about 95% of a wash solution and/or second wash solution separated from a biomass may be recycled for future use.

Lysing a Washed or Unwashed Biomass

As shown in FIG. 2A and FIG. 2B, a washed biomass may be lysed 220 to form a lysed biomass 221. In some embodiments, a biomass (e.g., unwashed) may be lysed to form a lysed biomass 221. According to some embodiments, lysing may be achieved using a combination of mechanical (e.g., milling), chemical (e.g., pH adjustment), and/or ultrasonic (e.g., sonication) methods. A lysing process may be achieved using, for example, a shear mill, a ball mill, a colloid mill, a knife mill, a hammer mill, shear mill, a grinding mill, a puree machine, a filter press, or any combination thereof.

In some embodiments, lysing may be performed at temperatures below room temperature. A lying fluid (e.g., water, recycled water, reverse osmosis water) may be added to a biomass or microcrop before or during lysing, according to some embodiments. For example, at least about 10%, at least about 20%, at least about 30%, at least about 40%, at least about 50%, at least about 60%, at least about 70%, at least about 80%, or at least about 90% of lysing fluid may be water generated as a result of reverse osmosis/nanofiltration of a filtration product (e.g., FIG. 3A, 362). In some embodiments a lysing fluid may be at a temperature below room temperature (e.g., about 12° C.).

Separating a Biomass

As shown in FIG. 2A and FIG. 2B, a lysed biomass 221 may be separated 225 to generate a juice fraction 226 and a solid fraction 227. In some embodiments, a biomass (e.g., *Lemna*), a washed biomass, a lysed biomass 221, or any combination thereof may be separated to generate a juice fraction and a solid fraction. A juice fraction 226 may include a protein-rich liquid and/or at least some solid particles (e.g., carbohydrates, fiber).

Separating 225 a lysed biomass 221 may involve pressing (e.g., belt press), centrifugation, filtration, pressurized filtration, or any combination thereof. Interchangeable unit operations for separating 225 a biomass (e.g., harvested microcrop), washed biomass, and/or lysed biomass include, for example, a decanter centrifuge, a belt press, a fan press, a rotary press, a screw press, a filter press, a finisher press, or any combination thereof.

Separating 225 may be performed at any desired temperature. Separating 225 may be performed at temperatures below room temperature (e.g., 12° C.), for example, to decrease proteolytic activity. In some embodiments, separating may be performed at a temperature below about 40° C., below about 30° C., or below about 20° C., or below about 15° C., or below about 10° C., or below about 15° C., or below about 10° C., or below about 5° C., or below about 2° C., or below about 1° C., or below about 0° C. Separating 225 may be performed, for example, at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C.

Separating a Solid Fraction

As shown in FIG. 2A and FIG. 2B, a solid fraction 227 may be further separated 230 to extract additional juice, forming a second juice 232 and a first solid 231. A second juice may include a protein-rich liquid and/or at least some solid particles (e.g., carbohydrates, fiber).

Separating a solid fraction to form a second juice and a first solid may involve pressing (e.g., belt press), centrifugation, filtration, pressurized filtration, or any combination thereof. Interchangeable unit operations for separating a solid fraction include, for example, a decanter centrifuge, a belt press, a fan press, a rotary press, a screw press, a filter press, a finisher press, or any combination thereof.

In some embodiments, as shown in FIG. 2A and FIG. 2B for example, other solid portions (e.g., a first cake 242, a second cake 247) which are collected at other stages in the process (e.g., separation of a juice fraction yields a first cake) may be combined with a first solid to form a solid mixture and the solid mixture may be further processed.

In some embodiments, a moisture content of a solid fraction and/or solid mixture is less than about 90%, or less than about 80%, or less than about 70%, or less than about 60%, or less than about 50%, or less than about 40%, or less than about 30%, or less than about 20%, or less than about 10% by weight.

Separating a Juice Fraction

As shown in FIG. 2A and FIG. 2B, a juice fraction 226 may be separated 240 to generate a first juice 241 and a first cake 242. A first juice may include a soluble protein. Separating 240 a juice fraction, in some embodiments, may involve centrifugation, filtration, pressurized filtration, or any combination thereof. Several different interchangeable unit operations may be used to separate a juice fraction including, for example, a high-speed disc stack centrifuge, a circular vibratory separator, a linear/inclined motion shaker, a decanter centrifuge, a filter press, pressurized filtration mechanisms, microfiltration, vacuum filtration, or any combination thereof.

Separating 240 may be performed, according to some embodiments, at temperatures below room temperature, for example, to decrease proteolytic activity. In some embodiments separating may be performed at a temperature below about 40° C., or below about 30° C., or below about 20° C., or below about 15° C., or below about 10° C., or below about 15° C., or below about 10° C., or below about 5° C., or below about 2° C., or below about 1° C., or below about 0° C. Separating may be performed at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C., in some embodiments.

Separating a First Cake and/or a Second Juice

As shown in FIG. 2A and FIG. 2B, a first cake 242 and a second juice 232 may be combined and further separated to form a third juice 246 and a second cake 247. In some embodiments, a first cake and a second juice may be independently subjected to further separation. Separating a first cake, a second juice, or any combination thereof may involve centrifugation, filtration, pressurized filtration, or any combination thereof. Several different interchangeable unit operations may be used to separate including, for example, a high-speed disc stack centrifuge, a circular vibratory separator, a linear/inclined motion shaker, a decanter centrifuge, a filter press, pressurized filtration mechanisms, microfiltration, vacuum filtration, or any combination thereof.

Separating may be performed, according to some embodiments, at temperatures below room temperature, for example, to decrease proteolytic activity. In some embodiments separating may be performed at a temperature below about 40° C., or below about 30° C., or below about 20° C., or below about 15° C., or below about 10° C., or below about 15° C., or below about 10° C., or below about 5° C., or below about 2° C., or below about 1° C., or below about 0° C. Separating may be performed at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C., in some embodiments.

As shown in FIG. 2A and FIG. 2B, in some embodiments a third juice 246 may be combined with a first juice 241 prior to further processing. A second cake 247 may be combined with a first solid 231 to form a solid mixture, in some embodiments, prior to further processing.

Filtering a First Juice, a Third Juice, or any Combination Thereof

As shown in FIG. 2A and FIG. 2B, a first juice 241, a third juice 246, or any combination thereof may be filtered to generate a soluble protein 251 and a reject stream 252. Filtration 250 may involve microfiltration, ultrafiltration, nanofiltration, or reverse osmosis filtration.

Suitable filter sizes for microfiltration may include, in some embodiments, ≤about 10 µm, or ≤about 5 µm, or ≤about 3 µm, or ≤about 2 µm, or ≤about 1 µm, or ≤about 0.5

µm, or ≤about 0.4 µm, or ≤about 0.3 µm, or ≤about 0.2 µm, or ≤about 0.1 µm. As shown in FIG. 2B, in some embodiments, a first juice, a third juice, or any combination thereof may be filtered 250 using microfiltration to generate a soluble protein 251 in a permeate and a reject stream product 253 in a retentate.

Ultrafiltration may involve membrane filtration using pressure, concentration gradients, or a combination thereof. Suitable nominal molecular weight cut-offs (NMWCO) for ultrafiltration may be, in some embodiments, at most in some embodiments, at most about 100 kDa, or at most about 90 kDa, or at most about 80 kDa, or at most about 70 kDa, or at most about 60 kDa, or at most about 55 kDa, or at most about 50 kDa, or at most about 45 kDa, or at most about 40 kDa, or at most about 30 kDa, or at most about 20 kDa, or at most about 15 kDa, or at most about 14 kDa, or at most about 13 kDa, or at most about 12 kDa, or at most about 11 kDa, or at most about 10 kDa, or at most about 9 kDa, or at most about 8 kDa, or at most about 7 kDa, or at most about 6 kDa, or at most about 5 kDa, or at most about 4 kDa, or at most about 3 kDa, or at most about 2 kDa, or at most about 1 kDa. In some embodiments, suitable NMWCO cut-offs for ultrafiltration may be in a range of at most about 1 kDa to at most about 10 kDa, at most about 2 kDa to at most about 10 kDa, at most about 3 kDa to at most about 10 kDa, at most about 3 kDa to at most about 15 kDa, or at most about 3 kDa to at most about 20 kDa, or at most about 3 kDa to at most about 60 kDa, or at most about 3 kDa to at most about 55 kDa, or at most about 10 kDa to at most about 55 kDa. A first juice 241, a third juice 246, or any combination thereof may be filtered 250 using ultrafiltration to generate a soluble protein 251 and a reject stream 252, according to some embodiments. A soluble protein may be in a retentate, as shown in FIG. 2A, or a permeate, as shown in FIG. 2B, depending upon molecular weight cut-offs for ultrafiltration. When reject stream 252 is a permeate of ultrafiltration (e.g., FIG. 2A) it may be recycled to a bioreactor system for cultivation of a microcrop (e.g., FIG. 1, 105).

In some embodiments, suitable filter sizes for nanofiltration may include ≤about 0.01 µm, or ≤about 0.009 µm, or ≤about 0.008 µm or ≤about 0.007 µm or ≤about 0.006 µm or ≤about 0.005 µm or ≤about 0.004 µm or ≤about 0.003 µm or ≤about 0.002 µm or ≤about 0.001 µm. According to some embodiments, suitable filter sizes for reverse osmosis filtration may include ≤about 0.001 µm, ≤about 0.0009 µm, ≤about 0.0008 µm, ≤about 0.0007 µm, ≤about 0.0006 µm, ≤about 0.0005≤about 0.0004 µm, ≤about 0.0003 µm, ≤about 0.0002 µm or ≤about 0.0001 µm. As shown in FIG. 2B, in some embodiments, a first juice, a third juice, or any combination thereof may be filtered 250 using nanofiltration or reverse osmosis filtration to generate a soluble protein 251 in a retentate and a permeate 252 of nanofiltered water or reverse osmosis water, respectively. In some embodiments reject stream 252 may be a permeate of nanofiltration or reverse osmosis filtration and may be recycled to a bioreactor system for cultivation of a microcrop (e.g., FIG. 1, 105).

Buffers, protease inhibitors, anti-microbial agents, chelators (e.g., EDTA), reducing agents, or any combination thereof may be added, in some embodiments, to a soluble protein 251. A soluble protein may be chilled and/or stored at a temperature below about 30° C., or below about 25° C., or below about 20° C., or below about 15° C., or below about 10° C., or below about 5° C., or below about 2° C., or below about 1° C., or below about 0° C., or below −2° C., or below −5° C., or below −10° C., in some embodiments. Chilling and/or storing a soluble protein at reduced temperatures may reduce degradation and/or improve protein recovery efficiency.

Reducing a Moisture Content of a Soluble Protein

In some embodiments a process may be used to reduce a moisture content of a soluble protein 251. In some embodiments, an evaporation process may be used to reduce a moisture content of soluble protein. In some embodiments, a moisture content of soluble protein 251 may be reduced by nanofiltration or reverse osmosis filtration. In some embodiments, a moisture content of soluble protein 251 may be reduced using nanofiltration with the soluble protein 251 in a retentate. A moisture content of soluble protein 251, in some embodiments, may be reduced using reverse osmosis filtration with the soluble protein 251 in a retentate. A permeate of nanofiltration or reverse osmosis filtration may be recycled (e.g., dilution fluid for lysis; wash solution), according to some embodiments.

Drying a Soluble Protein

A soluble protein 251 may be dried 255 to generate a dry protein concentrate, according to some embodiments. A drying procedure, in some embodiments, may reduce a moisture content of a soluble protein to a desired level (e.g., higher or lower moisture content, a desired moisture content). A moisture content of a dry protein concentrate, in some embodiments, may be, for example, below about 90%, or below about 80%, or below about 70%, or below about 60%, or below about 50%, or below about 40%, or below about 30%, or below about 20%, or below about 10%, or below about 5%, or below about 1% by weight of the dry protein concentrate. In some embodiments, a protein concentration of a dry protein concentrate may be from about 30% to about 95%, or from about 40% to about 90%, or from about 50% to about 85%, or from about 60% to about 80%, or from about 70% to about 75% by weight of the dry protein concentrate. A drying procedure may be performed using a mechanism including, for example, a spray dryer, double drum dryer, flash dryer, an evaporator, or any combination thereof.

Processing a First Solid and/or Solid Mixture

A first solid and/or solid mixture may be further processed to generate one or more carbohydrate-rich products. As described previously, a solid mixture may include one or more of a first solid 231, a first cake 242, a second cake 247, or any combination thereof that remain after one or more separation processes 230/240/245. Carbohydrate rich products may include a dry biocrude product suitable as a fuel feedstock or a carbohydrate-rich meal suitable as a human or animal feed supplement (e.g., *Lemna* meal).

A first solid and/or solid mixture may be processed (e.g., drying, pelletization), in some embodiments, to generate at least one of a dry biocrude and a carbohydrate-rich meal. According to some embodiments, processing a first solid and/or solid mixture involves drying and/or pelletization.

A process for generating a carbohydrate-rich product (e.g., dry biocrude and/or carbohydrate-rich) meal may be varied depending upon characteristics desired, including, for example, moisture content, particle size, protein content, fat content, fiber content, ash content, shelf-life, pellet size, texture, or any combination thereof.

In some embodiments, a first solid and/or a solid mixture may be dried to reduce a moisture content of a resulting carbohydrate-rich product (e.g., dry biocrude and/or carbohydrate-rich meal). A drying procedure, in some embodiments, may be performed in conjunction with (e.g., prior to, following) other processing of a first solid and/or a solid mixture, such that an end product is a carbohydrate-rich product with a reduced moisture content. A drying procedure may be performed, in some embodiments, using a dryer mechanism including, for example, a spray dryer, double drum dryer, flash dryer, evaporator, or any combination thereof.

A moisture content of a carbohydrate-rich product (e.g., dry biocrude and/or carbohydrate-rich meal) may be below about 90%, or below about 80%, or below about 70%, or below about 60%, or below about 50%, or below about 40%, or below about 30%, or below about 20%, or below about 10%, or below about 5%, or below about 1% by weight of the product, in some embodiments.

Polyphenol Removal

In some embodiments, a juice fraction 226, a first juice 241, a second juice 232, a third juice 246, and/or a soluble protein 251 may undergo a processing step for the selective removal of at least one polyphenol (a).

Solvent Wash

In some embodiments, a soluble protein 251 may undergo a solvent wash (b). Solvent washing (b) may also follow drying 255.

FIGS. 3A and 3B

FIG. 3A and FIG. 3B illustrate an embodiment for processing a microcrop (e.g., *Lemna*) for production of protein concentrate and/or carbohydrate rich products. A microcrop may be harvested (e.g., FIG. 1, 110) forming a biomass (e.g., FIG. 1, 111).

Washing a Biomass

As shown in FIG. 3A and FIG. 3B, a biomass may be washed 315 prior to processing, according to some embodiments. A wash procedure may remove debris, contaminants, nutrients, microorganisms, and/or toxins. A wash solution, in some embodiments, may be combined with a biomass to form a slurry. According to some embodiments, a wash solution (e.g., a first, second, and/or third wash solution) may have a temperature below room temperature (e.g., about 12° C.). A wash solution, in some embodiments, may have a temperature above room temperature (e.g., 50° C.). In some embodiments, a wash solution may comprise any desired portion of recycled fluid. For example, a wash solution may comprise at least about 10% (v/v), at least about 20% (v/v), at least about 30% (v/v), at least about 40% (v/v), at least about 50% (v/v), at least about 60% (v/v), at least about 70% (v/v), at least about 80% (v/v), or at least about 90% (v/v) recycled from another stage of the process (e.g., recycled wash solution 316, a first reject stream from filtration (e.g., FIG. 3A, 352), a second reject stream from filtrations (e.g., FIG. 3A, 357)). In some embodiments, a second wash solution (e.g., water, ozonated water, recycled wash solution FIG. 1, 316) may be applied to a biomass. A third wash solution (e.g., water, ozonated water, recycled wash solution) may be applied to a biomass, in some embodiments. In some embodiments a first wash solution may be a reject stream from a filtration process (e.g., FIG. 3A, 352, 357), a second wash solution may be water, and a third wash solution may be ozonated water. Some or all of a wash solution (e.g., a first wash solution, second wash solution, and/or third wash solution) may be separated, in some embodiments, from a biomass (e.g., using an inclined screen or vibratory screen).

Some or all of a wash solution, second wash solution, and/or third wash solution may be collected and/or reused, according to some embodiments. At least about 40%, or at least about 50%, or at least about 60%, or at least about 70%, or at least about 80%, or at least about 90%, or at least about 95% of a wash solution and/or second wash solution separated from a biomass may be recycled for future use.

Lysing a Washed or Unwashed Biomass

As shown in FIG. 3A and FIG. 3B, a washed biomass may be lysed 320 to form a lysed biomass 321. In some embodiments, a biomass (e.g., unwashed) may be lysed to form a lysed biomass 321. According to some embodiments, lysing may be achieved using a combination of mechanical (e.g., milling), chemical (e.g., pH adjustment), and/or ultrasonic (e.g., sonication) methods. A lysing process may be achieved using, for example, a shear mill, a ball mill, a colloid mill, a knife mill, a hammer mill, a grinding mill, a puree machine, a filter press, or any combination thereof.

In some embodiments, lysing may be performed at temperatures below room temperature. A lying fluid (e.g., water, recycled water, reverse osmosis water) may be added to a biomass or microcrop before or during lysing, according to some embodiments. As shown in FIG. 3A and FIG. 3B, a permeate 362 from reverse osmosis/nan-filtration of a second soluble protein may be recycled as a lysing fluid. For example, at least about 10%, at least about 20%, at least about 30%, at least about 40%, at least about 50%, at least about 60%, at least about 70%, at least about 80%, or at least about 90% of lysing fluid may be water generated as a result of reverse osmosis/nanofiltration of a filtration product (e.g., FIG. 3A, 362). In some embodiments a lysing fluid may be at a temperature below room temperature (e.g., about 12° C.). A lysing fluid may be at a temperature above room temperature (e.g., 50° C.).

Separating a Biomass

As shown in FIG. 3A and FIG. 3B, a lysed biomass 321 may be separated 325 to generate a juice fraction 326 and a solid fraction 327. In some embodiments, a biomass (e.g., *Lemna*), a washed biomass, a lysed biomass 321, or any combination thereof may be separated to generate a juice fraction and a solid fraction. A juice fraction 326 may include a protein-rich liquid and/or at least some solid particles (e.g., carbohydrates, fiber).

Separating 325 a lysed biomass 321 may involve pressing (e.g., belt press), centrifugation, filtration, pressurized filtration, or any combination thereof. Interchangeable unit operations for separating 325 a biomass (e.g., harvested microcrop), washed biomass, and/or lysed biomass include, for example, a decanter centrifuge, a belt press, a fan press, a rotary press, a screw press, a filter press, a finisher press, or any combination thereof.

Separating 325 may be performed at any desired temperature. Separating 325 may be performed at temperatures below room temperature (e.g., 12° C.), for example, to decrease proteolytic activity. In some embodiments, separating may be performed at a temperature below about 40° C., below about 30° C., or below about 20° C., or below about 15° C., or below about 10° C., or below about 15° C., or below about 10° C., or below about 5° C., or below about 2° C., or below about 1° C., or below about 0° C. Separating 325 may be performed, for example, at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C.

Separating a Solid Fraction

As shown in FIG. 3, a solid fraction 327 may be further separated 330 to extract additional juice, forming a second juice 332 and a first solid 331. A second juice may include a protein-rich liquid and/or at least some solid particles (e.g., carbohydrates, fiber).

Separating a solid fraction to form a second juice and a first solid may involve pressing (e.g., belt press), centrifugation, filtration, pressurized filtration, or any combination thereof. Interchangeable unit operations for separating a solid fraction include, for example, a decanter centrifuge, a belt press, a fan press, a rotary press, a screw press, a filter press, a finisher press, or any combination thereof.

In some embodiments, as shown in FIG. 3 for example, other solid fractions (e.g., a first cake 342, a second cake 347) which are collected at other stages in a process (e.g., separation of a juice fraction yields a first cake) may be combined with a first solid to form a solid mixture and the solid mixture may be further processed.

In some embodiments, a moisture content of a solid fraction and/or solid mixture is less than about 90%, or less than about 80%, or less than about 70%, or less than about 60%, or less than about 50%, or less than about 40%, or less than about 30%, or less than about 20%, or less than about 10% by weight.

Separating a Juice Fraction

As shown in FIG. 3A and FIG. 3B, a juice fraction 326 may be separated to generate a first juice 341 and a first cake 342. A first juice may include a soluble protein. Separating a juice fraction, in some embodiments, may involve centrifugation, filtration, pressurized filtration, or any combination thereof. Several different interchangeable unit operations may be used to separate a juice fraction including, for example, a high-speed disc stack centrifuge, a circular vibratory separator, a linear/inclined motion shaker, a decanter centrifuge, a filter press, pressurized filtration mechanisms, microfiltration, vacuum filtration, or any combination thereof.

Separating may be performed, according to some embodiments, at temperatures below room temperature, for example, to decrease proteolytic activity. In some embodiments separating may be performed at a temperature below about 40° C., or below about 30° C., or below about 20° C., or below about 15° C., or below about 10° C., or below about 15° C., or below about 10° C., or below about 5° C., or below about 2° C., or below about 1° C., or below about 0° C. Separating may be performed at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C., in some embodiments.

Separating a First Cake and/or a Second Juice

As shown in FIG. 3A and FIG. 3B, a first cake 342 and a second juice 332 may be combined and further separated to form a third juice 346 and a second cake 347. In some embodiments, a first cake and a second juice may be independently subjected to further separation. Separating a first cake, a second juice, or any combination thereof may involve centrifugation, filtration, pressurized filtration, or any combination thereof. Several different interchangeable unit operations may be used to separate including, for example, a high-speed disc stack centrifuge, a circular vibratory separator, a linear/inclined motion shaker, a decanter centrifuge, a filter press, pressurized filtration mechanisms, microfiltration, vacuum filtration, or any combination thereof.

Separating may be performed, according to some embodiments, at temperatures below room temperature, for example, to decrease proteolytic activity. In some embodiments separating may be performed at a temperature below about 40° C., or below about 30° C., or below about 20° C., or below about 15° C., or below about 10° C., or below about 15° C., or below about 10° C., or below about 5° C., or below about 2° C., or below about 1° C., or below about 0° C. Separating may be performed at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C., in some embodiments.

As shown in FIG. 3A and FIG. 3B, in some embodiments a third juice 346 may be combined with a first juice 341 prior to further processing. A second cake 347 may be combined with a first solid 331 to form a solid mixture, in some embodiments, prior to further processing.

Filtering a First Juice, a Third Juice, or any Combination Thereof

As shown in FIG. 3A and FIG. 3B, a first juice 341, a third juice 346, or any combination thereof may be filtered to generate a first soluble protein 351 and a first reject stream 352. Filtration 350 may involve microfiltration, ultrafiltration, nanofiltration, or reverse osmosis filtration.

Suitable filter sizes for microfiltration may include, in some embodiments, ≤about 10 μm, or ≤about 5 μm, or ≤about 3 μm, or ≤about 2 μm, or ≤about 1 μm, or ≤about 0.5 μm, or ≤about 0.4 μm, or ≤about 0.3 μm, or ≤about 0.2 μm, or ≤about 0.1 μm. As shown in FIG. 3B, in some embodiments, a first juice, a third juice, or any combination thereof may be filtered 350 using microfiltration to generate a first soluble protein 351 in a permeate and a reject stream product 353 in a retentate.

Ultrafiltration may involve membrane filtration using pressure, concentration gradients, or a combination thereof. Suitable NMWCOs for ultrafiltration may be, in some embodiments, at most in some embodiments, at most about 100 kDa, or at most about 90 kDa, or at most about 80 kDa, or at most about 70 kDa, or at most about 60 kDa, or at most about 55 kDa, or at most about 50 kDa, or at most about 45 kDa, or at most about 40 kDa, or at most about 30 kDa, or at most about 20 kDa, or at most about 15 kDa, or at most about 14 kDa, or at most about 13 kDa, or at most about 12 kDa, or at most about 11 kDa, or at most about 10 kDa, or at most about 9 kDa, or at most about 8 kDa, or at most about 7 kDa, or at most about 6 kDa, or at most about 5 kDa, or at most about 4 kDa, or at most about 3 kDa, or at most about 2 kDa, or at most about 1 kDa. In some embodiments, suitable NMWCO cut-offs for ultrafiltration may be in a range of at most about 1 kDa to at most about 10 kDa, at most about 2 kDa to at most about 10 kDa, at most about 3 kDa to at most about 10 kDa, at most about 3 kDa to at most about 15 kDa, or at most about 3 kDa to at most about 20 kDa, or at most about 3 kDa to at most about 60 kDa, or at most about 3 kDa to at most about 55 kDa, or at most about 10 kDa to at most about 55 kDa.

A first juice 341, a third juice 346, or any combination thereof may be filtered 350 using ultrafiltration to generate a first soluble protein 351 and a reject stream 352, according to some embodiments. A first soluble protein may be in a retentate, as shown in FIG. 3A, or a permeate, as shown in FIG. 3B, depending upon the molecular weight cut-offs for ultrafiltration. When first reject stream 352 is a permeate of ultrafiltration (e.g., FIG. 3A) it may be recycled to a bioreactor system for cultivation of a microcrop (e.g., FIG. 1, 105).

In some embodiments, suitable filter sizes for nanofiltration may include ≤about 0.01 μm or ≤about 0.009 μm or ≤about 0.008 μm or ≤about 0.007 μm or ≤about 0.006 μm or ≤about 0.005 μm or ≤about 0.004 μm or ≤about 0.003 μm or ≤about 0.002 μm or ≤about 0.001 μm. According to some embodiments, suitable filter sizes for reverse osmosis filtration may include ≤about 0.001 μm, ≤about 0.0009 μm, ≤about 0.0008 μm, ≤about 0.0007 μm, ≤about 0.0006 μm, ≤about 0.0005≤about 0.0004≤about 0.0003 μm, ≤about 0.0002 μm or ≤about 0.0001 μm. As shown in FIG. 3B, in some embodiments, a first juice, a third juice, or any combination thereof may be filtered 350 using nanofiltration or reverse osmosis filtration to generate a first soluble protein 351 in a retentate and a permeate 352 of nanofiltered water or reverse osmosis water, respectively. In some embodiments first reject stream 352 may be a permeate of nanofiltration or reverse osmosis filtration and may be recycled to a bioreactor system for cultivation of a microcrop (e.g., FIG. 1, 105).

Buffers, protease inhibitors, anti-microbial agents, chelators (e.g., EDTA), reducing agents, or any combination thereof may be added, in some embodiments, to a soluble protein 351. A soluble protein may be chilled and/or stored at a temperature below about 30° C., or below about 25° C., or below about 20° C., or below about 15° C., or below about 10° C., or below about 5° C., or below about 2° C., or below about 1° C., or below about 0° C., or below −2° C., or below −5° C., or below −10° C., in some embodiments. Chilling and/or storing a soluble protein at reduced temperatures may reduce degradation and/or improve protein recovery efficiency.

Filtering a First Soluble Protein

As shown in FIG. 3A and FIG. 3B, first soluble protein 351 may be filtered 355 to generate and second soluble protein 356 and a second reject stream 357. Filtration 355 may involve microfiltration, ultrafiltration, nanofiltration, or reverse osmosis filtration.

Suitable filter sizes for microfiltration may include, in some embodiments, ≤about 10 μm or ≤about 5 μm, or ≤about 3 μm, or ≤about 2 μm, or ≤about 1 μm, or ≤about 0.5 μm or ≤about 0.4 μm or ≤about 0.3 μm or ≤about 0.2 μm or ≤about 0.1 μm. In some embodiments, a first soluble protein may be filtered 355 using microfiltration to generate a second soluble protein 356 in a permeate and a reject stream product in a retentate.

Ultrafiltration may involve membrane filtration using pressure, concentration gradients, or a combination thereof. Suitable NMWCOs for ultrafiltration may be, in some embodiments, at most in some embodiments, at most about 100 kDa, or at most about 90 kDa, or at most about 80 kDa, or at most about 70 kDa, or at most about 60 kDa, or at most about 55 kDa, or at most about 50 kDa, or at most about 45 kDa, or at most about 40 kDa, or at most about 30 kDa, or at most about 20 kDa, or at most about 15 kDa, or at most about 14 kDa, or at most about 13 kDa, or at most about 12 kDa, or at most about 11 kDa, or at most about 10 kDa, or at most about 9 kDa, or at most about 8 kDa, or at most about 7 kDa, or at most about 6 kDa, or at most about 5 kDa, or at most about 4 kDa, or at most about 3 kDa, or at most about 2 kDa, or at most about 1 kDa. In some embodiments, suitable NMWCO cut-offs for ultrafiltration may be in a range of at most about 1 kDa to at most about 10 kDa, at most about 2 kDa to at most about 10 kDa, at most about 3 kDa to at most about 10 kDa, at most about 3 kDa to at most about 15 kDa, or at most about 3 kDa to at most about 20 kDa, or at most about 3 kDa to at most about 60 kDa, or at most about 3 kDa to at most about 55 kDa, or at most about 10 kDa to at most about 55 kDa.

A first soluble protein may be filtered 355 using ultrafiltration to generate a second soluble protein 355 and a reject stream 357, according to some embodiments. A second soluble protein may be in a retentate, as shown in FIG. 3A and FIG. 3B, or a permeate (not shown) depending upon the molecular weight cut-offs for ultrafiltration. According to some embodiments, diafiltration may be used in conjunction with ultrafiltration and/or nanofiltration, by an addition of water to a first soluble protein 351 or a second soluble protein 356. In some embodiments, using diafiltration in conjunction with ultrafiltration and/or nanofiltration by an addition of water to a first soluble protein 351, a second soluble protein 356, or a combination thereof may further eliminate permeable solutes from a first soluble protein 351, a second soluble protein 356, or a combination thereof. Eliminating permeable solutes from a first soluble protein 351, a second soluble protein 356, or a combination thereof may increase a protein purity of a first soluble protein 351, a second soluble protein 356, or a combination thereof.

When second reject stream 357 is a permeate of ultrafiltration (e.g., FIG. 3A) it may be recycled to a bioreactor system for cultivation of a microcrop (e.g., FIG. 1, 105).

In some embodiments, suitable filter sizes for nanofiltration may include ≤about 0.01 μm or ≤about 0.009 μm or ≤about 0.008 μm or ≤about 0.007 μm or ≤about 0.006 μm or ≤about 0.005 μm or ≤about 0.004 μm or ≤about 0.003 μm or ≤about 0.002 μm or ≤about 0.001 μm. According to some embodiments, suitable filter sizes for reverse osmosis filtration may include ≤about 0.001 μm, ≤about 0.0009 μm, ≤about 0.0008 μm, ≤about 0.0007 μm, ≤about 0.0006 μm, ≤about 0.0005≤about 0.0004≤about 0.0003 μm, ≤about 0.0002 μm or ≤about 0.0001 μm. As shown in FIG. 3A and FIG. 3B, in some embodiments, a first soluble protein may be filtered 355 using nanofiltration or reverse osmosis filtration to generate a second soluble protein 356 in a retentate and a permeate 357 of nanofiltered water or reverse osmosis water, respectively. In some embodiments second reject stream 357 may be a permeate of nanofiltration or reverse osmosis filtration and may be recycled to a bioreactor system for cultivation of a microcrop (e.g., FIG. 1, 105).

In some embodiments buffers, protease inhibitors, anti-microbial agents, chelators (e.g., EDTA), reducing agents, or any combination thereof may be added to a second soluble protein 356. A second soluble protein may be chilled and/or stored at a temperature below about 30° C., or below about 25° C., or below about 20° C., or below about 15° C., or below about 10° C., or below about 5° C., or below about 2° C., or below about 1° C., or below about 0° C., or below −2° C., or below −5° C., or below −10° C. Chilling and/or storing a second soluble protein at reduced temperatures may reduce degradation and/or improve protein recovery efficiency.

Reducing a Moisture Content of a First Soluble Protein and/or Second Soluble Protein In some embodiments a process may be used to reduce a moisture content of a first soluble protein 351 and/or a second soluble protein 356.

In some embodiments an evaporation process may be used to reduce a moisture content of a first soluble protein 351 or a second soluble protein 356 and generate a concentrated protein 361. Reducing a moisture content of a first soluble protein 351 or a second soluble protein 356 may reduce capital and operational expenditures, for example, by reducing an energy needed to dry a concentrated protein 361. Evaporation may be performed by, for example, a thermal (evaporative) means such as: a rising film evaporator, a falling film evaporator, a natural circulation evaporator (vertical or horizontal), an agitated-film evaporator, a multiple-effect evaporator, by vacuum evaporation, or any combination thereof.

As shown in FIG. 3, a moisture content of a first soluble protein 351 or a second soluble protein 356 may be reduced, in some embodiments, by nanofiltration or reverse osmosis filtration. In some embodiments, a moisture content of a first soluble protein 351 or a second soluble protein 356 may be reduced using nanofiltration with the first soluble protein 351 or the second soluble protein 356, respectively, in a retentate. A moisture content of a first soluble protein 351 or a second soluble protein 356, in some embodiments, may be reduced using reverse osmosis filtration with the first soluble protein 351 or the second soluble protein 356, respectively in a retentate. A permeate 362 of nanofiltration or reverse osmosis filtration may be recycled (e.g., dilution fluid for lysis; wash solution), according to some embodiments. In some embodiments, reverse osmosis filtration and/or nanofiltration may reduce a concentration of undesirable dissolved compounds (e.g., salts, calcium ions) in a resulting concentrated protein 361.

Drying a Soluble Protein

A concentrated protein 361 may be dried 365 to generate a dry protein concentrate, according to some embodiments. A drying procedure, in some embodiments, may reduce a moisture content of a concentrated protein 361 to a desired level (e.g., higher or lower moisture content, a desired moisture content). A moisture content of a dry protein concentrate, in some embodiments, may be, for example, below about 90%, or below about 80%, or below about 70%, or below about 60%, or below about 50%, or below about 40%, or below about 30%, or below about 20%, or below about 10%, or below about 5%, or below about 1% by weight of a dry protein concentrate. In some embodiments, a protein concentration of a dry protein concentrate may be from about 30% to about 95%, or from about 40% to about 90%, or from about 50% to about 85%, or from about 60% to about 80%, or from about 70% to about 75% by weight of a dry protein concentrate. A drying procedure may be performed using a mechanism including, for example, a spray dryer, double drum dryer, flash dryer, an evaporator, or any combination thereof.

Processing a First Solid and/or Solid Mixture

A first solid and/or solid mixture may be further processed to generate one or more carbohydrate-rich products. As described previously, a solid mixture may include one or more of a first solid 331, a first cake 342, a second cake 347, or any combination thereof that remain after one or more separation processes 330/340/345. Carbohydrate rich products may include a dry biocrude product suitable as a fuel feedstock or a carbohydrate-rich meal suitable as a human or animal feed supplement (e.g., *Lemna* meal).

A first solid and/or solid mixture may be processed (e.g., drying, pelletization), in some embodiments, to generate at least one of a dry biocrude and a carbohydrate-rich meal. According to some embodiments, processing a first solid and/or solid mixture involves drying and/or pelletization.

A process for generating a carbohydrate-rich product (e.g., dry biocrude and/or carbohydrate-rich) meal may be varied depending upon the specific characteristics desired, including, for example, moisture content, particle size, protein content, fat content, fiber content, ash content, shelf-life, pellet size, texture, or any combination thereof.

In some embodiments, a first solid and/or a solid mixture may be dried to reduce a moisture content of a resulting carbohydrate-rich product (e.g., dry biocrude and/or carbohydrate-rich meal). A drying procedure, in some embodiments, may be performed in conjunction with (e.g., prior to, following) other processing of a first solid and/or a solid mixture, such that an end product is a carbohydrate-rich product with a reduced moisture content. A drying procedure may be performed, in some embodiments, using a dryer mechanism including, for example, a spray dryer, double drum dryer, flash dryer, evaporator, or any combination thereof.

A moisture content of a carbohydrate-rich product (e.g., dry biocrude and/or carbohydrate-rich meal) may be below about 90%, or below about 80%, or below about 70%, or below about 60%, or below about 50%, or below about 40%, or below about 30%, or below about 20%, or below about 10%, or below about 5%, or below about 1% by weight of the product, in some embodiments.

Polyphenol Removal

In some embodiments, a juice fraction 326, a first juice 341, a second juice 332, a third juice 346, a first soluble protein 351, a second soluble protein 356, and/or a concentrated protein 361 may undergo a processing step for the selective removal of at least one polyphenol (a).

Solvent Wash

In some embodiments, a first soluble protein 351, a second soluble protein 356, and/or a concentrated protein 361 may undergo a solvent wash (b). Solvent washing (b) may also follow drying 365.

FIG. 4

FIG. 4 is a flow diagram illustrating a process for continuously producing a protein concentrate and/or carbohydrate rich products from a biomass according to a specific example embodiment of the disclosure. In some embodiments a process for growing, harvesting, and separating a microcrop (e.g., aquatic plant species, *Lemna, algal* species) may be multiple cycles or a continuous process for a production of protein concentrate (e.g., soluble protein, dry protein concentrate) and/or carbohydrate rich products such that byproducts of an earlier cycle of the process may be recycled into one or more subsequent cycles of the process. Recycling of one or more by-products may reduce an overall water requirement for a process. In some embodiments, a process may be configured to minimize a net energy input required (i.e., energy conservation).

A microcrop may be harvested (e.g., FIG. 1, 110) forming a biomass (e.g., FIG. 1, 111).

Washing a Biomass

As shown in FIG. 4, a biomass may be washed 415 prior to processing, according to some embodiments. A wash procedure may remove debris, contaminants, nutrients, microorganisms, and/or toxins. A wash solution, in some embodiments, may be combined with a biomass to form a slurry. According to some embodiments, a wash solution (e.g., a first, second, and/or third wash solution) may have a temperature below room temperature (e.g., about 12° C.). A wash solution, in some embodiments, may have a temperature above room temperature (e.g., 50° C.). In some embodiments, a wash solution may comprise any desired portion of recycled fluid. For example, a wash solution may comprise at least about 10% (v/v), at least about 20% (v/v), at least about 30% (v/v), at least about 40% (v/v), at least about 50% (v/v), at least about 60% (v/v), at least about 70% (v/v), at least about 80% (v/v), or at least about 90% (v/v) recycled from another stage of a process (e.g., recycled wash solution 416, a first reject stream from filtration (e.g., FIG. 3A, 352), a second reject stream from filtrations (e.g., FIG. 4, 457)).

According to some embodiments, a wash solution recycled, at least in part, from another stage of a process (e.g., recycled wash solution 416, a first reject stream from filtration (e.g., FIG. 3A, 352), a second reject stream from filtrations (e.g., FIG. 4, 457)) may have a temperature below room temperature (e.g., about 12° C.) as a result of chilling of an earlier product in a process (e.g., chilling a first juice, chilling a first soluble protein, chilling a second soluble protein). A wash solution recycled, at least in part, from another stage of a process (e.g., recycled wash solution 416, a first reject stream from filtration (e.g., FIG. 3A, 352), a second reject stream from filtrations (e.g., FIG. 4, 457)) may have a temperature above room temperature (e.g., about 50° C.) as a result of a heat exchange mechanism. For example, a heat exchange mechanism may be configured to use released energy from a drying process 335 to heat a first reject stream from filtration (e.g., FIG. 3A, 352), a second reject stream from filtrations (e.g., FIG. 4, 457)). Such recycling may be configured to reduce an energy input requirement of a process (e.g., chilled recycled fluids cool a process they are added to; heat exchanger reduces energy requirement to heat a first reject stream).

In some embodiments, a second wash solution (e.g., water, ozonated water, recycled wash solution FIG. 4, 416) may be applied to a biomass. A third wash solution (e.g., water, ozonated water, recycled wash solution) may be applied to a biomass, in some embodiments. In some embodiments a first wash solution may be a reject stream from a filtration process (e.g., FIG. 3A, 352; FIG. 4, 457), a second wash solution may be water, and a third wash solution may be ozonated water. Some or all of a wash solution (e.g., a first wash solution, second wash solution, and/or third wash solution) may be separated, in some embodiments, from a biomass (e.g., using an inclined screen or vibratory screen).

Some or all of a wash solution, second wash solution, and/or third wash solution may be collected and/or reused, according to some embodiments. At least about 40%, or at least about 50%, or at least about 60%, or at least about 70%, or at least about 80%, or at least about 90%, or at least about 95% of a wash solution and/or second wash solution separated from a biomass may be recycled for future use.

Lysing a Washed or Unwashed Biomass

As shown in FIG. 4, a washed biomass may be lysed 420 to form a lysed biomass 421. In some embodiments, a biomass (e.g., unwashed) may be lysed to form a lysed biomass. According to some embodiments, lysing may be achieved using a combination of mechanical (e.g., milling), chemical (e.g., pH adjustment), and/or ultrasonic (e.g., sonication) methods. A lysing process may be achieved using, for example, a shear mill, a ball mill, a colloid mill, a knife mill, a hammer mill, a grinding mill, a puree machine, a filter press, or any combination thereof.

In some embodiments, lysing may be performed at temperatures below room temperature. A lying fluid (e.g., water, recycled water, reverse osmosis water) may be added to a biomass or microcrop before or during lysing, according to some embodiments. As shown in FIG. 4, a permeate 462 from reverse osmosis/nanofiltration of a second soluble protein may be recycled as a lysing fluid. For example, at least about 10%, at least about 20%, at least about 30%, at least about 40%, at least about 50%, at least about 60%, at least about 70%, at least about 80%, or at least about 90% of lysing fluid may be water generated as a result of reverse osmosis/nanofiltration of a filtration product (e.g., FIG. 4, 462). In some embodiments a lysing fluid may be at a temperature below room temperature (e.g., about 12° C.). A lysing fluid may be at a temperature above room temperature (e.g., 50° C.). According to some embodiments, a lysing fluid recycled, at least in part, from another stage of a process (e.g., FIG. 4, 462) may have a temperature below room temperature (e.g., about 12° C.) as a result of chilling of an earlier product in the process (e.g., chilling a first juice, chilling a first soluble protein, chilling a second soluble protein). A lysing fluid recycled, at least in part, from another stage of a process (e.g., FIG. 4, 462) may have a temperature above room temperature (e.g., about 50° C.) as a result of a heat exchange mechanism. For example, a heat exchange mechanism may be configured to use released energy from a drying process 335 to heat a permeate (e.g., FIG. 4, 462) resulting from a reverse osmosis or nanofiltration process (e.g., FIG. 4, 460).

Separating a Biomass

As shown in FIG. 4, a lysed biomass may be separated 425 to generate a juice fraction 426 and a solid fraction 427. In some embodiments, a biomass (e.g., *Lemna*), a washed biomass, a lysed biomass, or any combination thereof may be separated to generate a juice fraction and a solid fraction. A juice fraction 426 may include a protein-rich liquid and/or at least some solid particles (e.g., carbohydrates, fiber).

Separating 425 a lysed biomass may involve pressing (e.g., belt press), centrifugation, filtration, pressurized filtration, or any combination thereof. Interchangeable unit operations for separating 425 a biomass (e.g., harvested microcrop), washed biomass, and/or lysed biomass include, for example, a decanter centrifuge, a belt press, a fan press, a rotary press, a screw press, a filter press, a finisher press, or any combination thereof.

Separating 425 may be performed at any desired temperature. Separating 425 may be performed at temperatures below room temperature (e.g., 12° C.), for example, to decrease proteolytic activity. In some embodiments, separating may be performed at a temperature below about 40° C., below about 30° C., or below about 20° C., or below about 15° C., or below about 10° C., or below about 15° C., or below about 10° C., or below about 5° C., or below about 2° C., or below about 1° C., or below about 0° C. Separating 425 may be performed, for example, at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C.

Separating a Solid Fraction

As shown in FIG. 4, a solid fraction 427 may be further separated 430 to extract additional juice, forming a second juice 432 and a first solid 431. A second juice may include a protein-rich liquid and/or at least some solid particles (e.g., carbohydrates, fiber).

Separating a solid fraction to form a second juice and a first solid may involve pressing (e.g., belt press), centrifugation, filtration, pressurized filtration, or any combination thereof. Interchangeable unit operations for separating a solid fraction include, for example, a decanter centrifuge, a belt press, a fan press, a rotary press, a screw press, a filter press, a finisher press, or any combination thereof.

As shown in FIG. 4, according to some embodiments, one or more of a first cake (e.g., FIG. 4, 442) and a second cake (e.g., FIG. 4, 447) that are collected in an earlier cycle may be combined with a solid fraction from a subsequent cycle prior to separation (e.g., FIG. 4, 430) of the solid fraction.

In some embodiments, a moisture content of a solid fraction and/or solid mixture is less than about 90%, or less than about 80%, or less than about 70%, or less than about 60%, or less than about 50%, or less than about 40%, or less than about 30%, or less than about 20%, or less than about 10% by weight.

Separating a Juice Fraction

As shown in FIG. 4, a juice fraction 426 may be separated 440 to generate a first juice 441 and a first cake 442. A first juice may include a soluble protein. Separating a juice fraction, in some embodiments, may involve centrifugation, filtration, pressurized filtration, or any combination thereof. Several different interchangeable unit operations may be used to separate a juice fraction including, for example, a high-speed disc stack centrifuge, a circular vibratory separator, a linear/inclined motion shaker, a decanter centrifuge, a filter press, pressurized filtration mechanisms, microfiltration, vacuum filtration, or any combination thereof.

Separating may be performed, according to some embodiments, at temperatures below room temperature, for example, to decrease proteolytic activity. In some embodiments separating may be performed at a temperature below about 40° C., or below about 30° C., or below about 20° C., or below about 15° C., or below about 10° C., or below about 15° C., or below about 10° C., or below about 5° C., or below about 2° C., or below about 1° C., or below about 0° C. Separating may be performed at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C., in some embodiments.

Separating a First Cake and/or a Second Juice

As shown in FIG. 4, a first cake 442 and a second juice 432 may be combined and further separated to form a third juice 446 and a second cake 447. In some embodiments, a first cake and a second juice may be independently subjected to further separation. Separating a first cake, a second juice, or any combination thereof may involve centrifugation, filtration, pressurized filtration, or any combination thereof. Several different interchangeable unit operations may be used to separate including, for example, a high-speed disc stack centrifuge, a circular vibratory separator, a linear/inclined motion shaker, a decanter centrifuge, a filter press, pressurized filtration mechanisms, microfiltration, vacuum filtration, or any combination thereof.

Separating may be performed, according to some embodiments, at temperatures below room temperature, for example, to decrease proteolytic activity. In some embodiments separating may be performed at a temperature below about 40° C., or below about 30° C., or below about 20° C., or below about 15° C., or below about 10° C., or below about 15° C., or below about 10° C., or below about 5° C., or below about 2° C., or below about 1° C., or below about 0° C. Separating may be performed at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C., in some embodiments.

As shown in FIG. 4, according to some embodiments, a third juice collected in an earlier cycle may be combined with a juice fraction from a subsequent cycle prior to further processing. In some embodiments a third juice may be combined with a first juice prior to further processing (e.g., FIG. 3A). A second cake may be combined with a first solid to form a solid mixture, in some embodiments, prior to further processing (e.g., FIG. 3A).

Filtering a First Juice, a Third Juice, or any Combination Thereof

As shown in FIG. 4, a first juice 441 may be filtered 450 to generate a first soluble protein 451 and a first reject stream 452. In some embodiments, a first juice, a third juice, or any combination thereof may be filtered to generate a first soluble protein and a first reject stream (e.g., FIG. 3A). Filtration 450 may involve microfiltration, ultrafiltration, nanofiltration, or reverse osmosis filtration.

Suitable filter sizes for microfiltration may include, in some embodiments, ≤about 10 µm, or ≤about 5 µm, or ≤about 3 µm, or ≤about 2 µm, or ≤about 1 µm, or ≤about 0.5 µm, or ≤about 0.4 µm, or ≤about 0.3 µm, or ≤about 0.2 µm, or ≤about 0.1 µm. As shown in FIG. 4, a first juice, a third juice, or any combination thereof may be filtered 450 using microfiltration to generate a first soluble protein 451 in a permeate and a reject stream product 453 in a retentate first reject stream 452.

Ultrafiltration may involve membrane filtration using pressure, concentration gradients, or a combination thereof. Suitable NMWCOs for ultrafiltration may be, in some embodiments, at most about 100 kDa, or at most about 90 kDa, or at most about 80 kDa, or at most about 70 kDa, or at most about 60 kDa, or at most about 55 kDa, or at most about 50 kDa, or at most about 45 kDa, or at most about 40 kDa, or at most about 30 kDa, or at most about 20 kDa, or at most about 15 kDa, or at most about 14 kDa, or at most about 13 kDa, or at most about 12 kDa, or at most about 11 kDa, or at most about 10 kDa, or at most about 9 kDa, or at most about 8 kDa, or at most about 7 kDa, or at most about 6 kDa, or at most about 5 kDa, or at most about 4 kDa, or at most about 3 kDa, or at most about 2 kDa, or at most about 1 kDa. In some embodiments, suitable NMWCO cut-offs for ultrafiltration may be in a range of at most about 1 kDa to at most about 10 kDa, at most about 2 kDa to at most about 10 kDa, at most about 3 kDa to at most about 10 kDa, at most about 3 kDa to at most about 15 kDa, or at most about 3 kDa to at most about 20 kDa, or at most about 3 kDa to at most about 60 kDa, or at most about 3 kDa to at most about 55 kDa, or at most about 10 kDa to at most about 55 kDa.

A first juice 441, a third juice 446, or any combination thereof may be filtered 450 using ultrafiltration to generate a first soluble protein 451 and a reject stream 452, according to some embodiments. A first soluble protein may be in a retentate (e.g., FIG. 3A) or a permeate, as shown in FIG. 4, depending upon the molecular weight cut-offs for ultrafiltration. When first reject stream 452 is a permeate of ultrafiltration (e.g., FIG. 3A) it may be recycled to a bioreactor system for cultivation of a microcrop (e.g., FIG. 1, 105).

In some embodiments, suitable filter sizes for nanofiltration may include ≤about 0.01 µm or ≤about 0.009 µm or ≤about 0.008 µm or ≤about 0.007 µm or ≤about 0.006 µm or ≤about 0.005 µm or ≤about 0.004 µm or ≤about 0.003 µm or ≤about 0.002 µm or ≤about 0.001 µm. According to some embodiments, suitable filter sizes for reverse osmosis filtration may include ≤about 0.001 µm, ≤about 0.0009 µm, ≤about 0.0008 µm, ≤about 0.0007 µm, ≤about 0.0006 µm, ≤about 0.0005≤about 0.0004≤about 0.0003 µm, ≤about 0.0002 µm or ≤about 0.0001 µm. In some embodiments, a first juice, a third juice, or any combination thereof may be filtered 450 using nanofiltration or reverse osmosis filtration to generate a first soluble protein (e.g., FIG. 3A, 351) in a retentate and a permeate (e.g., FIG. 3A, 352) of nanofiltered water or reverse osmosis water, respectively. In some embodiments a first reject stream (e.g., FIG. 3A, 352) may be a permeate of nanofiltration or reverse osmosis filtration and may be recycled to a bioreactor system for cultivation of a microcrop (e.g., FIG. 1, 105).

Buffers, protease inhibitors, anti-microbial agents, chelators (e.g., EDTA), reducing agents, or any combination thereof may be added, in some embodiments, to a soluble protein 451. A soluble protein may be chilled and/or stored at a temperature below about 30° C., or below about 25° C., or below about 20° C., or below about 15° C., or below about 10° C., or below about 5° C., or below about 2° C., or below about 1° C., or below about 0° C., or below −2° C., or below −5° C., or below −10° C., in some embodiments. Chilling and/or storing a soluble protein at reduced temperatures may reduce degradation and/or improve protein recovery efficiency.

Filtering a First Soluble Protein

As shown in FIG. 4, first soluble protein 451 may be filtered 455 to generate and second soluble protein 456 and a second reject stream 457. Filtration 455 may involve microfiltration, ultrafiltration, nanofiltration, or reverse osmosis filtration.

Suitable filter sizes for microfiltration may include, in some embodiments, ≤about 10 μm or ≤about 5 μm, or ≤about 3 μm, or ≤about 2 μm, or ≤about 1 μm, or ≤about 0.5 μm or ≤about 0.4 μm or ≤about 0.3 μm or ≤about 0.2 μm or ≤about 0.1 μm. In some embodiments, a first soluble protein may be filtered 455 using microfiltration to generate a second soluble protein in a permeate (not shown) and a reject stream product in a retentate.

Ultrafiltration may involve membrane filtration using pressure, concentration gradients, or a combination thereof. Suitable NMWCOs for ultrafiltration may be, in some embodiments, at most about 100 kDa, or at most about 90 kDa, or at most about 80 kDa, or at most about 70 kDa, or at most about 60 kDa, or at most about 55 kDa, or at most about 50 kDa, or at most about 45 kDa, or at most about 40 kDa, or at most about 30 kDa, or at most about 20 kDa, or at most about 15 kDa, or at most about 14 kDa, or at most about 13 kDa, or at most about 12 kDa, or at most about 11 kDa, or at most about 10 kDa, or at most about 9 kDa, or at most about 8 kDa, or at most about 7 kDa, or at most about 6 kDa, or at most about 5 kDa, or at most about 4 kDa, or at most about 3 kDa, or at most about 2 kDa, or at most about 1 kDa. In some embodiments, suitable NMWCO cut-offs for ultrafiltration may be in a range of at most about 1 kDa to at most about 10 kDa, at most about 2 kDa to at most about 10 kDa, at most about 3 kDa to at most about 10 kDa, at most about 3 kDa to at most about 15 kDa, or at most about 3 kDa to at most about 20 kDa, or at most about 3 kDa to at most about 60 kDa, or at most about 3 kDa to at most about 55 kDa, or at most about 10 kDa to at most about 55 kDa. A first soluble protein may be filtered 455 using ultrafiltration to generate a second soluble protein 455 and a reject stream 357, according to some embodiments. A second soluble protein may be in a retentate, as shown in FIG. 4, or a permeate (not shown) depending upon the molecular weight cut-offs for ultrafiltration. When second reject stream 457 is a permeate of ultrafiltration, as shown in FIG. 4, it may be recycled to a bioreactor system for cultivation of a microcrop (e.g., FIG. 1, 105).

In some embodiments, suitable filter sizes for nanofiltration may include ≤about 0.01 μm or ≤about 0.009 μm or ≤about 0.008 μm or ≤about 0.007 μm or ≤about 0.006 μm or ≤about 0.005 μm or ≤about 0.004 μm or ≤about 0.003 μm or ≤about 0.002 μm or ≤about 0.001 μm. According to some embodiments, suitable filter sizes for reverse osmosis filtration may include ≤about 0.001 μm, ≤about 0.0009 μm, ≤about 0.0008 μm, ≤about 0.0007 μm, ≤about 0.0006 μm, ≤about 0.0005 μm, ≤about 0.0004 μm, ≤about 0.0003 μm, ≤about 0.0002 μm, or ≤about 0.0001 μm. As shown in FIG. 4, in some embodiments, a first soluble protein may be filtered 455 using nanofiltration or reverse osmosis filtration to generate a second soluble protein 456 in a retentate and a permeate 457 of nanofiltered water or reverse osmosis water, respectively. In some embodiments second reject stream 457 may be a permeate of nanofiltration or reverse osmosis filtration and may be recycled to a bioreactor system for cultivation of a microcrop (e.g., FIG. 1, 105).

In some embodiments buffers, protease inhibitors, antimicrobial agents, chelators (e.g., EDTA), reducing agents, or any combination thereof may be added to a second soluble protein 456. A second soluble protein may be chilled and/or stored at a temperature below about 30° C., or below about 25° C., or below about 20° C., or below about 15° C., or below about 10° C., or below about 5° C., or below about 2° C., or below about 1° C., or below about 0° C., or below −2° C., or below −5° C., or below −10° C. Chilling and/or storing the second soluble protein at reduced temperatures may reduce degradation and/or improve protein recovery efficiency.

Reducing a Moisture Content of a First Soluble Protein and/or Second Soluble Protein In some embodiments a process may be used to reduce a moisture content of a first soluble protein 451 and/or a second soluble protein 456 (e.g., dewatering).

In some embodiments an evaporation process may be used to reduce a moisture content of a first soluble protein 451 or a second soluble protein 456 and generate a concentrated protein 461. Reducing a moisture content of a first soluble protein 451 or a second soluble protein 456 may reduce capital and operational expenditures, for example, by reducing an energy needed to dry a concentrated protein 461. Evaporation may be performed by, for example, a thermal (evaporative) means such as: a rising film evaporator, a falling film evaporator, a natural circulation evaporator (vertical or horizontal), an agitated-film evaporator, a multiple-effect evaporator, by vacuum evaporation, or any combination thereof.

As shown in FIG. 4, a moisture content of a first soluble protein 451 or a second soluble protein 456 may be reduced, in some embodiments, by nanofiltration or reverse osmosis filtration. In some embodiments, a moisture content of a first soluble protein 451 or a second soluble protein 456 may be reduced using nanofiltration with the first soluble protein 451 or a second soluble protein 456, respectively, in a retentate. A moisture content of a first soluble protein 451 or a second soluble protein 456, in some embodiments, may be reduced using reverse osmosis filtration with the first soluble protein 451 or a second soluble protein 456, respectively in a retentate. A permeate 462 of nanofiltration or reverse osmosis filtration may be recycled (e.g., dilution fluid for lysis; wash solution), according to some embodiments. In some embodiments, reverse osmosis filtration and/or nanofiltration may reduce a concentration of undesirable dissolved compounds (e.g., salts, calcium ions) in a resulting concentrated protein 461.

Drying a Soluble Protein

A concentrated protein 461 may be dried 465 to generate a dry protein concentrate, according to some embodiments. A drying procedure, in some embodiments, may reduce a moisture content of a concentrated protein 461 to a desired level (e.g., higher or lower moisture content, a desired moisture content). A moisture content of a dry protein concentrate, in some embodiments, may be, for example, below about 90%, or below about 80%, or below about 70%, or below about 60%, or below about 50%, or below about 40%, or below about 30%, or below about 20%, or below about 10%, or below about 5%, or below about 1% by weight of the dry protein concentrate. In some embodiments, a protein concentration of a dry protein concentrate may be from about 30% to about 95%, or from about 40% to about 90%, or from about 50% to about 85%, or from about 60% to about 80%, or from about 70% to about 75% by weight of the dry protein concentrate. A drying procedure may be performed using a mechanism including, for example, a spray dryer, double drum dryer, flash dryer, an evaporator, or any combination thereof.

Processing a First Solid and/or Solid Mixture

A first solid and/or solid mixture may be further processed to generate one or more carbohydrate-rich products. As described previously, a solid mixture may include one or more of a first solid 431, a first cake 442, a second cake 447, or any combination thereof that remain after one or more separation processes 430/440/445. Carbohydrate rich products may include a dry biocrude product suitable as a fuel feedstock or a carbohydrate-rich meal suitable as a human or animal feed supplement (e.g., *Lemna* meal).

A first solid and/or solid mixture may be processed (e.g., drying, pelletization), in some embodiments, to generate at least one of a dry biocrude and a carbohydrate-rich meal. According to some embodiments, processing a first solid and/or solid mixture involves drying and/or pelletization.

A process for generating a carbohydrate-rich product (e.g., dry biocrude and/or carbohydrate-rich) meal may be varied depending upon the specific characteristics desired, including, for example, moisture content, particle size, protein content, fat content, fiber content, ash content, shelf-life, pellet size, texture, or any combination thereof.

In some embodiments, a first solid and/or a solid mixture may be dried to reduce a moisture content of a resulting carbohydrate-rich product (e.g., dry biocrude and/or carbohydrate-rich meal). A drying procedure, in some embodiments, may be performed in conjunction with (e.g., prior to, following) other processing of a first solid and/or a solid mixture, such that an end product is a carbohydrate-rich product with a reduced moisture content. A drying procedure may be performed, in some embodiments, using a dryer mechanism including, for example, a spray dryer, double drum dryer, flash dryer, evaporator, or any combination thereof.

A moisture content of a carbohydrate-rich product (e.g., dry biocrude and/or carbohydrate-rich meal) may be below about 90%, or below about 80%, or below about 70%, or below about 60%, or below about 50%, or below about 40%, or below about 30%, or below about 20%, or below about 10%, or below about 5%, or below about 1% by weight of a product, in some embodiments.

Polyphenol Removal

In some embodiments, a juice fraction 426, a first juice 441, a second juice 432, a third juice 446, a first soluble protein 451, a second soluble protein 456, and/or a concentrated protein 461 may undergo a processing step for the selective removal of at least one polyphenol (a).

Solvent Wash

In some embodiments, a first soluble protein 451, a second soluble protein 456, and/or a concentrated protein 461 may undergo a solvent wash (b). Solvent washing (b) may also follow drying 465.

Systems of Extracting Proteins and Carbohydrate-rich Products from Photosynthetic Aquatic Species Embodiments of the disclosure also provide systems of extracting proteins and carbohydrate rich products from photosynthetic aquatic species. Such systems may include, for example: a lysing unit (e.g., 220/320/420) for lysing a biomass (e.g., washed, unwashed) to generate a lysed biomass; a first separating unit (e.g., 225/325/425) for separating a lysed biomass to generate a juice fraction and a solid fraction; a second separating unit (e.g., 240/340/440) for forming a first juice and a first cake; a third separating unit (e.g., 230/330/430) for forming a first solid and a second juice; a fourth separating unit (e.g., 245/345/445) for forming a second cake and a third juice; a protein concentration unit (e.g., 250/350/355/450/455) for forming: a soluble protein and a reject stream, or for forming a first soluble protein and a first reject stream, or for forming a second soluble protein and second reject stream; a dewatering unit (e.g., 360/460) for forming a concentrated protein and a permeate; a protein drying unit (e.g., 255/365/465) for drying a soluble protein product to generate a dry protein concentrate; and a carbohydrate drying unit (e.g., 235/335/435) for drying a first solid or solid mixture to generate at least one carbohydrate-rich product (e.g., dry bio-crude, carbohydrate-rich meal). Summarized in Table 6 are apparatuses that can be included in the units described above.

TABLE 6

| Example Apparatuses | |
|---|---|
| Lysing Unit (e.g., 220/320) | Shear Mill, Ball Mill, Colloid Mill, Knife Mill, Hammer Mill, Grinding Mill, Puree Machine, Filter Press |
| First Separating Unit (e.g., 225/325) | Decanter Centrifuge, Belt Press, Fan Press, Rotary Press, Screw Press, Filter Press, Finisher Press |
| Second Separating Unit (e.g., 240/340) | High-speed Disc Stack Centrifuge, Circular Vibratory Separator, Linear/inclined Motion Shaker, Decanter Centrifuge, Filter Press, Pressurized Filtration Mechanisms, Microfiltration Module, Vacuum Filtration Apparatus |
| Third Separating Unit (e.g., 230/330) | Belt Press, Fan Press, Rotary Press, Screw Press, Filter Press, Finisher Press, Decanter Centrifuge |
| Fourth Separating Unit (e.g., 245/345) | High-speed Disc Stack Centrifuge, Circular Vibratory Separator, Linear/inclined Motion Shaker, Decanter Centrifuge, Filter Press, Pressurized Filtration Mechanisms, Microfiltration, Vacuum Filtration Apparatus |
| Protein Concentration Unit (e.g., 250/350/355) | Microfiltration Module, Ultrafiltration Module, Nanofiltration Module, Reverse Osmosis Filtration Module *Any of the above modules may be configured as single or multistage crossflow membrane filtration systems. |
| Dewatering Unit | Rising Film Evaporator, Falling Film Evaporator, Natural Circulation Evaporator (vertical or horizontal), Agitated- Film Evaporator, Multiple-effect Evaporator, Vacuum Evaporation Apparatus, Nano-filtration Module, Reverse Osmosis Filtration Module |
| Protein Drying Unit | Spray dryer, Drum dryer, Flash dryer |
| Carbohydrate Drying Unit | Spray dryer, Drum dryer, Flash dryer |

EXAMPLES

A soluable microcrop composition was subjected to a polyphenol reduction process in accordance with the disclosure. Table 7 below summarizes analyses perform on the starting material and product. As shown, polyphenol content was reduced by 50% without substantial loss of protein (i.e., 95% recovery relative to the starting material).

TABLE 7

| Wet Stream Analysis | | | |
|---|---|---|---|
| Control Protein Content | 4.4 | mg/ml | |
| | 4400 | mg/l | |
| Protein Recovery | 95% | | >95% |
| Treated Protein Content | 4180 | mg/l | |
| Control Polyphenol Content | 769.1 | mg/l | |
| Polyphenol reduction | 50% | | Range 45-55% |
| Treated Polyphenol Content | 384.55 | mg/l | |

It is understood that the listed apparatuses for each unit are for illustration purposes only, and this is not intended to limit the scope of the application. A specific combination of these or other apparatuses or units can be configured in such a system for the intended use based on the teachings in the application.

Persons skilled in the art may make various changes in the shape, size, number, separation characteristic, and/or arrangement of parts without departing from the scope of the instant disclosure. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure. Where desired, some embodiments of the disclosure may be practiced to the exclusion of other embodiments.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value +/− about 10%, depicted value +/− about 50%, depicted value +/− about 100%) and/or a range endpoint. With respect to the former, a value of 50 depicted in an example, table, and/or drawing may form the basis of a range of, for example, about 45 to about 55, about 25 to about 100, and/or about 0 to about 100. Concentrations and/or ratios, where provided, may refer to a specific example of the relevant component (e.g., a specific protein, a specific carbohydrate, a specific fat, a specific polyphenol) or the total concentration of the relevant component (e.g., total protein, total carbohydrate, total fat, total polyphenol).

These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

What is claimed is:

1. A system for recovering a highly soluble protein product from a biomass comprising a microcrop, the system comprising:
a lysing unit configured to lyse a first portion of the biomass to form a first portion of lysed biomass;
a first separating unit configured to separate the first portion of lysed biomass to generate a first portion of a juice fraction and a first portion of a solid fraction;
a second separating unit configured to separate the first portion of the juice fraction to generate a first portion of a first juice and a first portion of a first cake;
a first filtration unit configured to filter the first portion of the first juice to generate a first portion of a soluble protein and a first reject stream, wherein the filtration unit is a microfiltration module and the first reject stream is a retentate;
a second filtration unit configured to filter the first portion of the soluble protein to generate a first portion of a second soluble protein and a second reject stream, wherein the second filtration unit is selected from an ultrafiltration module, a diafiltration module, and a nanofiltration module;
a dewatering unit configured to concentrate the first portion of the second soluble protein to generate a first portion of a concentrated soluble protein, wherein the dewatering unit is selected from a reverse osmosis filtration module and a nanofiltration module; and
a drying unit, configured to dry the first portion of the concentrated soluble protein to generate a first portion of a dry protein concentrate having a protein concentration of at least about 50% by weight and a solubility value (% water soluble nitrogen) of at least 50%.

2. The system of claim 1 further comprising a third separating unit configured to separate the first portion of the solid fraction to generate a first portion of a first solid and a first portion of a second juice.

3. The system of claim 2 further comprising:
a fourth separating unit configured to separate at least one of the first portion of the first cake and the first portion of the second juice to generate a first portion of a second cake and a first portion of a third juice;
a second lysing unit, configured to lyse a second portion of the biomass to form a second portion of a lysed biomass;
a fifth separating unit, configured to separate the second portion of lysed biomass to generate a second portion of the juice fraction and a second portion of the solid fraction;
a sixth separating unit, configured to separate the second portion of the juice fraction to generate a second portion of the first juice and a second portion of the first cake, wherein:
the first portion of the third juice and the second portion of the juice fraction are combined prior to separating the second portion of the juice fraction.

4. The system of claim 2 further comprising:
a fourth separating unit, configured to separate at least one of (1) the first portion of the first cake and (2) the first portion of the second juice, to generate a first portion of a third juice and a first portion of a second cake;
a first combining unit, configured to combine at least one of the first portion of the first solid, the first portion of the first cake, and the first portion of the second cake; and
a processing unit, configured to process the first portion of the solid mixture to generate a carbohydrate-rich product, wherein the carbohydrate-rich product comprises at least one of a dry biocrude and a carbohydrate-rich meal.

5. A system for treating a biomass comprising a microcrop to produce a product comprising soluble microcrop protein, the system comprising:
a first lysing unit configured to lyse a first portion of a biomass to form a first portion of a lysed biomass;
a first separating unit configured to separate the first portion of the lysed biomass to generate a first portion of a juice fraction and a first portion of a solid fraction;
a second separating unit configured to separate the first portion of the juice fraction to generate a first portion of a first juice and a first portion of a first cake, wherein the first portion of the first juice comprises the soluble microcrop protein;
a first filtration unit, comprising a microfiltration module, configured to microfilter the first portion of the first juice to generate a first portion of a first soluble protein and a first reject stream, wherein the first reject stream is a retentate and the microfiltration module comprises a filter having a filter size of 0.5 µm; and
a second filtration unit configured to filter the first portion of the first soluble protein to generate a first portion of a second soluble protein and a second reject stream, the second filtration unit comprising at least one of an ultrafiltration module, a diafiltration module, and a nanofiltration module.

6. The system of claim 5 further comprising a dewatering module, configured to concentrate the first portion of the second soluble protein to generate a first portion of a concentrated soluble protein and a permeate, wherein the dewatering module comprises at least one of a reverse osmosis filtering unit and a nanofiltration unit.

7. The system of claim 3 further comprising a first washing unit, configured to wash the first portion of the biomass with a first wash solution or to wash the second portion of the biomass with the first wash solution or to wash the first and second portions of the biomass with the first wash solution.

8. The system of claim 7, further comprising:
a second washing unit, configured to wash the first portion of the biomass with a second wash solution or to wash the second portion of the biomass with the second wash solution or to wash the first and second portions of the biomass the second wash solution; and
a third washing unit, configured to wash the first portion of the biomass with a third wash solution or to wash the second portion of the biomass with the third wash solution or to wash the first and second portions of the biomass the third wash solution, wherein:
the first wash solution, the second wash solution, and the third wash solution are independently selected from the reject stream, water, or an ozonated solution.

9. The system of claim 1, wherein the ultrafiltration module comprises a filter having a nominal molecular weight cut-off of up to about 10 kDa.

10. The system of claim 1, wherein the microfiltration module comprises an ultrafiltration filter comprising a filter having a nominal molecular weight cut-off of about 3 kDa.

11. The system of claim 1, wherein the microcrop comprises *Lemna*.

12. The system of claim 1, further comprising a washing unit, configured to wash the highly soluble protein product with at least one solvent, the at least one solvent comprising methanol, ethanol, acetone, hexane, dichloromethane, ethyl acetate, propanol, isopropanol, glycerol, and any combination thereof.

13. The system of claim 1 further comprising a reducing unit, configured to subject the highly soluble protein product to a polyphenol reduction process to generate a product having a reduced concentration of at least one polyphenol.

14. The system of claim 6, further comprising a first drying unit, configured to dry the portion of the concentrated soluble protein to generate a first portion of a dry protein concentrate.

15. The system of claim 5, wherein the ultrafiltration module comprises a filter having a nominal molecular cut-off weight of up to about 10 kDa.

16. The system of claim 14, further comprising:
a third separating unit, configured to separate the first portion of the solid fraction to generate a first portion of a first solid and a first portion of a second juice; and
a processing unit, configured to process the first portion of the first solid to generate a carbohydrate-rich product, wherein the carbohydrate-rich product comprises a dry biocrude or a carbohydrate-rich meal.

17. The system of claim 16, further comprising:
a fourth separating unit, configured to separate at least one of (1) the first portion of the first cake, and (2) the first portion of the second juice, to generate a first portion of a third juice and a first portion of a second cake;
a second lysing unit, configured to lyse a second portion of the biomass to form a second portion of lysed biomass;
a fifth separating unit, configured to separate the second portion of the lysed biomass to generate a second portion of the juice fraction and a second portion of the solid fraction;
a sixth separating unit, configured to separate the second portion of the juice fraction to generate a second portion of the first juice and a second portion of the first cake;
a third filtering unit comprising a microfiltration module, configured to microfilter the second portion of the first juice to generate a second portion of the first soluble protein and the first reject stream; and
a fourth filtration unit, configured to filter the second portion of the first soluble protein to generate a second portion of the second soluble protein and the second reject stream, wherein the first portion of the third juice and the second portion of the juice fraction are combined prior to separating the second portion of the juice fraction.

18. The system of claim 14, further comprising:
a fourth separating unit, configured to separate at least one of (1) the first portion of the first cake and (2) the first portion of the second juice, to generate a first portion of a third juice and a first portion of a second cake;
a combining unit, configured to combine at least one of the first portion of the first solid, the first portion of the first cake, and the first portion of the second cake, to generate a first portion of a solid mixture; and
a second processing unit, configured to process the first portion of the solid mixture to generate a carbohydrate-rich product, wherein the carbohydrate-rich product comprises a dry biocrude or a carbohydrate-rich meal.

19. The system of claim 17, further comprising:
a first wash unit, configured to wash the first portion of biomass with a first wash solution or to wash the second portion of the biomass with the first wash solution or to wash the first and second portions of the biomass with the first wash solution.

20. The system of claim 19, further comprising:
a second wash unit, configured to wash the first portion of biomass with a second wash solution or to wash the second portion of the biomass with the second wash solution or to wash the first and second portions of the biomass with the second wash solution; and
a third wash unit, configured to wash the first portion of biomass with a third wash solution or to wash the second portion of the biomass with the third wash solution or to wash the first and second portions of the biomass with the third wash solution, wherein:
the first wash solution, the second wash solution, and the third wash solution are independently selected from the reject stream, water, and an ozonated solution.

21. The system of claim 6, further comprising:
a chilling unit, configured to chill at least of the first portion of lysed biomass, the first portion of the juice fraction, the first portion of the first juice, the first portion of the first soluble protein, the first reject stream, the first portion of the second soluble protein fraction, the second reject stream, and the permeate, to form a chilled stream.

22. The system of claim 21, wherein the chilling unit is configured to lower the temperature of at least of the first portion of lysed biomass, the first portion of the juice fraction, the first portion of the first juice, the first portion of the first soluble protein, the first reject stream, the first portion of the second soluble protein fraction, the second reject stream, and the permeate, to about 12 degrees Celsius.

23. The system of claim 21, further comprising:
a directing unit, configured to direct the chilled stream to flow in proximity to a donor stream having thermal energy such that the chilled stream absorbs at least some of the donor stream thermal energy, wherein the donor stream comprises at least one of the first portion of the lysed biomass, the first portion of the juice fraction, and the first portion of the first juice.

24. The system of claim 21, further comprising:
a directing unit, configured to direct a thermal energy from at least one of the drying the concentrated protein and the chilling the flow in proximity to a recipient stream such that the recipient stream absorbs at least some of the thermal energy to form a heated stream, wherein the recipient stream comprises at least one of the first portion of the lysed biomass, the first portion of the juice fraction, the first portion of the first juice, the first portion of the first soluble protein fraction, the first reject stream, the first portion of the second soluble protein fraction, the second reject stream, and the permeate.

* * * * *